United States Patent
Zhang et al.

(10) Patent No.: US 10,723,701 B2
(45) Date of Patent: Jul. 28, 2020

(54) QUINOLYL-SUBSTITUTED CARBOXYLIC ACID COMPOUND OR PHARMACEUTICALLY ACCEPTABLE SALT THEREOF, PHARMACEUTICAL COMPOSITION OF THE SAME, AND USE OF THE SAME

(71) Applicant: BEIJING KONRUNS PHARMACEUTICAL CO., LTD., Beijing (CN)

(72) Inventors: Zhiqiang Zhang, Beijing (CN); Xijuan Wang, Beijing (CN); Xuehui Zhang, Beijing (CN); Junxia Qiu, Beijing (CN); Jiehe Yang, Beijing (CN); Xiaokai Zhang, Beijing (CN); Peng Yao, Beijing (CN)

(73) Assignee: BEIJING KONRUNS PHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 16/343,271

(22) PCT Filed: Sep. 29, 2017

(86) PCT No.: PCT/CN2017/104518
§ 371 (c)(1),
(2) Date: Apr. 18, 2019

(87) PCT Pub. No.: WO2018/072614
PCT Pub. Date: Apr. 26, 2018

(65) Prior Publication Data
US 2019/0256470 A1    Aug. 22, 2019

(30) Foreign Application Priority Data
Oct. 18, 2016    (CN) .......................... 2016 1 0909448

(51) Int. Cl.
| | | |
|---|---|---|
| *C07D 215/00* | (2006.01) |
| *C07D 215/233* | (2006.01) |
| *A61P 35/00* | (2006.01) |
| *A61K 31/4709* | (2006.01) |
| *A61P 1/16* | (2006.01) |
| *A61P 37/02* | (2006.01) |
| *C07D 401/12* | (2006.01) |
| *A61P 25/00* | (2006.01) |
| *A61P 27/02* | (2006.01) |
| *A61K 31/47* | (2006.01) |
| *A61P 9/00* | (2006.01) |
| *A61P 3/10* | (2006.01) |
| *A61P 17/06* | (2006.01) |

(52) U.S. Cl.
CPC .......... *C07D 215/233* (2013.01); *A61K 31/47* (2013.01); *A61K 31/4709* (2013.01); *A61P 1/16* (2018.01); *A61P 3/10* (2018.01); *A61P 9/00* (2018.01); *A61P 17/06* (2018.01); *A61P 25/00* (2018.01); *A61P 27/02* (2018.01); *A61P 35/00* (2018.01); *A61P 37/02* (2018.01); *C07D 401/12* (2013.01)

(58) Field of Classification Search
CPC .................................................... C07D 215/00
USPC ......................................................... 546/153
See application file for complete search history.

(56) References Cited

U.S. PATENT DOCUMENTS

| | | | |
|---|---|---|---|
| 7,037,925 B2 | 5/2006 | Larsson et al. | |
| 8,933,230 B2 | 1/2015 | Yun et al. | |
| 9,186,318 B2 * | 11/2015 | Yun ...................... | C07D 401/12 |

(Continued)

FOREIGN PATENT DOCUMENTS

| | | |
|---|---|---|
| CN | 1507434 A | 6/2004 |
| CN | 102408411 B | 10/2014 |
| EP | 2 769 976 A1 | 8/2014 |

(Continued)

OTHER PUBLICATIONS

PCT International Search Report dated Dec. 26, 2017, Application No. PCT/CN2017/104518, 4 Pages.

(Continued)

*Primary Examiner* — Niloofar Rahmani
(74) *Attorney, Agent, or Firm* — Brooks Kushman P.C.

(57) ABSTRACT

The present application provides a quinolyl-substituted carboxylic acid compound as shown in formula (I) or a pharmaceutically acceptable salt thereof, as well as a method for preparing the compound, a use of the compound, and a formulation containing the quinolyl-substituted carboxylic acid compound or the pharmaceutically acceptable salt thereof. This type of compounds are inhibitors for AXL and/or VEGFR2 protein kinase, and can be used to treat diseases caused by abnormality of the two protein kinases, such as, tumor, etc.

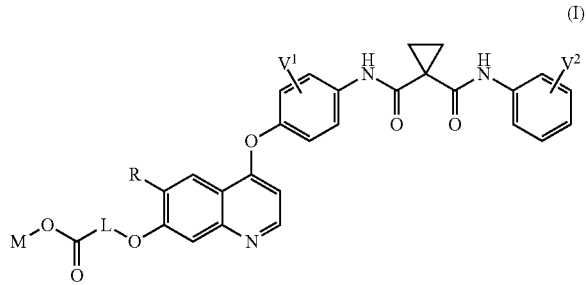

(I)

8 Claims, No Drawings

(56) References Cited

U.S. PATENT DOCUMENTS

2014/0221425 A1    8/2014  Yun et al.

FOREIGN PATENT DOCUMENTS

WO    2005/030140 A2    4/2005
WO    2012/100459 A1    8/2012

OTHER PUBLICATIONS

Ballatore, C. et al., Carboxylic Acid (Bio)Isosteres in Drug Design, ChemMedChem, Jan. 29, 2013, vol. 8, No. 3, pp. 385-395 Section Hydroxamic Acids.
Singapore Search Report and Written Opinion, dated Jan. 21, 2020, Application No. 11201903463P, 6 Pages.
Paola Clapetti and Bruno Giethien—Camille Georges Wermuth: Chapter 15 "Molecular Variations Based on Isosteric Replacements", Jan. 1, 2008, The Practice of Medicinal Chemistry (Third Edition), pp. 290-342.
Extended European Search Report dated Mar. 25, 2020, Application No. 17862141.3, Applicant Beijing Konruns Pharmaceutical Co., Ltd., 7 Pages.

\* cited by examiner

QUINOLYL-SUBSTITUTED CARBOXYLIC ACID COMPOUND OR PHARMACEUTICALLY ACCEPTABLE SALT THEREOF, PHARMACEUTICAL COMPOSITION OF THE SAME, AND USE OF THE SAME

CROSS-REFERENCE TO RELATED APPLICATIONS

This application is the U.S. national phase of PCT Application No. PCT/CN2017/104518 filed on Sep. 29, 2017, which claims priority to Chinese Patent Application No. 201610909448.4 filed on Oct. 18, 2016, which are incorporated herein by reference in their entireties.

TECHNICAL FIELD

The present application relates to the field of organic chemistry and medicinal chemistry, and specifically, to a quinolyl-substituted carboxylic acid compound or a pharmaceutically acceptable salt thereof, a method for manufacturing the quinolyl-substituted carboxylic acid compound or the pharmaceutically acceptable salt thereof, a pharmaceutical composition containing the compound, and a use of the pharmaceutical composition.

BACKGROUND

Protein kinases are a class of phosphotransferases that transfer γ-phosphate group of ATP to specific amino acid residues of a substrate to phosphorylate proteins, so as to exert their physiological and biochemical functions. The protein kinases are an important class of kinases. They play a major role in signal transduction in two aspects: one aspect is to regulate activity of proteins through phosphorylation; the other is to amplify the signal cascade through phosphorylation of proteins, so as to initiate a cellular response.

Abnormal protein kinase activity is not only closely related to abnormity in a certain link of a series of signal transduction pathways inside and outside cells, such as proliferation, apoptosis, and metastasis of tumors, etc., but also is a major reason for a series of other human diseases involving inflammation or proliferative response, such as rheumatoid arthritis, cardiovascular diseases and diseases of nervous system, asthma, psoriasis and the like. More than 400 human diseases are known to be directly or indirectly related to protein kinases, which makes protein kinases become another pivotal class of medicine targets following G-protein coupled receptors.

The protein kinase family consists of more than 500 members and is generally classified into two types, protein tyrosine kinases (PTKs) and serine-threonine kinases. According to the position of the kinase in the cell, the protein kinase family also can be classified into receptor kinases and non-receptor kinases (also known as intracellular kinases). The receptor kinases are generally tyrosine kinases, also referred to as receptor tyrosine kinases (RTKs). The receptor kinases are composed of extracellular, transmembrane, and intracytoplasmic portions, and a catalytically active portion of the kinases is located in the intracytoplasmic portion. Most serine-threonine kinases are located in cells and belong to the non-receptor kinases or cytosolic kinases.

Typical representatives of the RTK family are growth factor receptors, which has at least 19 subfamilies. Several major subfamilies are described as follow:

(a) HER family tyrosine receptor kinases, including epithelial growth factor receptor (EGFR), HER2, HER3 and HER4. The EGFR is a target of several synthesized small molecule medicines, such as Tarceva®, Tykerb® and monoclonal antibody Erbitux®, for the treatment of non-small cell lung cancer.

(b) A family consisting of insulin receptor (IR), insulin-like growth factor I receptor (IGF-1R), and insulin receptor-related receptor (IRR), in which the IGF-1R is a recognized anti-cancer target. However, the IGF-1R is too similar to IR, and especially the intracellular kinase portion of the IGF-1R has an amino acid sequence that is 100% identical to that of IR, so that an inhibition of IGF-1R activity is usually accompanied with an inhibition of IR activity. There is evidence proving that IR is also an effective anti-cancer target. However, it is necessary to find a balance between benefits and safety risks when using IR inhibitors for anti-cancer due to their risk of elevating blood glucose.

(c) A family of platelet-derived growth factor receptors (PDGFRs), including PDGFR-α, PDGFR-β, CSF1R, c-KIT, and c-fms. c-KIT is also a molecular target of a leukemia therapeutic medicine Gleevec® for the treatment of gastrointestinal stromal tumors.

(d) A family of vascular endothelial growth factor receptors (VEGFRs), including Fms-like tyrosine kinase 1 (FLT1) (or VEGFR1), KDR (or VEGFR-2), and FLT4 (or VEGFR3). The members of this subfamily are molecular targets of Sutent® and Naxavar®.

(e) A family of fibroblast growth factor receptors (FGFRs), including FGFR1, FGFR2, FGFR3 and FGFR4 and seven ligands FGF1, FGF2, FGF3, FGF4, FGF5, FGF6 and FGF7. The members of this subfamily are molecular targets of medicines that are still in clinical trials.

(f) MET family, including c-Met, also known as human hepatocyte growth factor receptor or hHGFR, and RON. c-Met plays a pivotal role in the growth and metastasis of initial tumors. The medicines targeting on c-Met are still in clinical trials.

(g) RET family, RET is a receptor for members of GDNF family, including RET51, RET43 and RET9 isoforms. The medicines targeting on RET are still in clinical trials.

(h) Eph family, which is the largest family of tyrosine receptor kinases, consisting of 16 receptors (EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6) and 9 ligands (EFNA1, EFNA2, EFNA3, EFNA4, EFNA5, EFNB1, EFNB2, EFNB3). These members play an important role in the growth of animals, and some members play a role in the development of tumor.

AXL, also known as UFO/ARK/Tyro, is another important tyrosine receptor kinase, whose ligand is the vitamin K-dependent growth promoting factor GAS6. The first discovery of AXL was as a transforming gene for chronic myeloid leukemia (CML). An overexpression of AXL can be found in metastatic colon cancer, thyroid cancer, breast cancer, prostate cancer, and melanoma. Inhibition of AXL activity can inhibit the growth, spreading and metastasis of tumor.

Non-receptor kinases do not have the extracellular portion and the transmembrane portion, i.e., the entire kinase is located in the cytoplasm. At least 24 non-receptor kinases are now known and can be divided into 11 subfamilies: Src, Frk, Btk, CsK, Abl, Zap70, Fes, Fps, Fak, Jak and AcK subfamilies. The Src subfamily is the largest, including Src, Yes, Fyn, Lyn, Lck, Blk, Hck, Fgr, AUR1, AUR2, and Yrk kinases. For more detailed information, see Neet, K.; Hunter, T. *Genes to Cells* 1996, 1, 147-169 and the literature cited therein. Although there are several non-receptor kinases of tyrosine kinase, most non-receptor kinases belong to the serine-threonine kinases. Several members are molecular targets for the leukemia therapeutic medicines such as Gleevec® and Sprycel®.

As described above, receptor kinases and non-receptor kinases serving as anti-tumor targets have been well demonstrated in clinical and practical applications and multiple anti-tumor medicines have been approved for market and the treatment of patients. In addition to tumor therapy, inhibition of abnormality of receptor kinases and non-receptor kinases can also be used to treat diseases including, but not limited to, psoriasis, cirrhosis, diabetes, diseases involving angiogenesis, diseases involving restenosis, eye diseases, age-related macular degeneration, rheumatoid arthritis and other inflammations, immune system diseases such as autoimmune diseases, cardiovascular diseases such as atherosclerosis, kidney diseases, and the like. Therefore, it is essential to continue to develop inhibitors of these kinases.

SUMMARY

One purpose of the present application is to provide a quinolyl-substituted carboxylic acid compound having protein kinase inhibitory activity, or a pharmaceutically acceptable salt thereof, and a method for preparing the quinolyl-substituted carboxylic acid compound or the pharmaceutically acceptable salt thereof.

Another purpose of the present application is to provide a use of the quinolyl-substituted carboxylic acid compound or the pharmaceutically acceptable salt thereof for preparing a medicament for treating a disease caused by abnormality of a protein kinase.

Yet another purpose of the present application is to provide a pharmaceutical composition comprising the above quinolyl-substituted carboxylic acid compound or the pharmaceutically acceptable salt thereof, applicable in treating a disease caused by abnormality of a protein kinase.

The technical solutions adopted in the present application are introduced as follow:

A quinolyl-substituted carboxylic acid compound as shown in formula (I) or a pharmaceutically acceptable salt thereof,

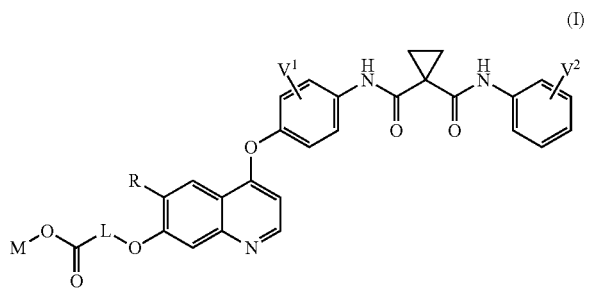

(I)

in which $V^1$ and $V^2$ are each independently selected from hydrogen, deuterium, halogen, $C_{1-6}$ alkyl and $C_{1-6}$ alkoxy;

R is hydrogen, $C_{1-12}$ alkyl, or $C_{1-12}$ alkoxy, and hydrogen of R is selectively substituted by $G^1$;

L is $C_{1-12}$ alkylene, and hydrogen of L is selectively substituted by $G^2$;

M is selected from:

(a) hydrogen, deuterium, $C_{2-12}$ alkyl, $C_{3-12}$ cycloalkyl, $C_{6-12}$ aryl, $C_{5-12}$ heteroaryl, and $C_{3-12}$ heteroalicyclic group, wherein hydrogen of M is selectively substituted by $G^3$; or (b) monovalent, divalent, trivalent, and tetravalent metal ions, preferably monovalent and divalent metal ions, and more preferably lithium ion, sodium ion, potassium ion, rubidium ion, cesium ion, magnesium ion, calcium ion, strontium ion, and barium ion; or (c) ammonium ion and an organic amine being protonated, the organic amine comprising, but not limited to, aliphatic amines substituted with $C_{1-12}$ alkyl, $C_{3-12}$ cycloalkyl, or $C_{3-12}$ heteroalicyclic group, the aliphatic amines being selectively substituted with one or more halogens or hydroxyls;

where $G^1$, $G^2$ and $G^3$ are each independently selected from hydrogen, deuterium, —CN, —CF$_3$, —CO$_2$H, halogen, $C_{1-12}$ alkyl, $C_{3-12}$ cycloalkyl, $C_{2-12}$ alkenyl, $C_{2-12}$ alkynyl, $C_{6-12}$ aryl, $C_{5-12}$ heteroaryl, $C_{3-12}$ heteroalicyclic group, $R^1O$—, $R^1R^2N$—, $R^1S(=O)_m$—, $R^1R^2NS(=O)_m$—, $R^3C(=O)$—, $R^1R^2NC(=O)$—, $R^1C(=O)$—, $R^3C(=O)O$—, $R^1R^2NC(=O)O$—, $R^3C(=O)NR^1$—, $R^1R^2NC(=O)NR^4$—, $R^1OC(=O)NR^4$—, $R^1S(=O)_mNR^4$—, $R^1R^2NS(=O)_mNR^4$—, $R^1R^2NC(=NR^5)NR^4$—, $R^1R^2NC(=CHNO_2)NR^4$—, $R^1R^2NC(=N-CN)NR^4$—, $R^1R^2NC(=NR^5)$—, $R^1S(=O)(=NR^5)NR^4$—, and $R^1R^2NS(=O)(=NR^5)$—;

$R^1$, $R^2$, $R^3$, $R^4$ and $R^5$ are each independently selected from hydrogen, deuterium, $C_{1-12}$ alkyl, $C_{2-12}$ alkenyl, $C_{2-12}$ alkynyl, $C_{3-12}$ cycloalkyl, $C_{6-12}$ aryl, $C_{5-12}$ heteroaryl, and $C_{3-12}$ heteroalicyclic group; $R^1$ and $R^2$, when being bonded to a same nitrogen atom, form a $C_{3-12}$ heteroalicyclic ring together with the nitrogen atom, wherein the $C_{3-12}$ heteroalicyclic ring selectively contains a hetero atom of O, N, and $S(=O)_m$; hydrogen of $R^1$, $R^2$, $R^3$, $R^4$ and $R^5$ is selectively substituted by halogen, CN, $C_{1-12}$ alkyl or $C_{3-12}$ cycloalkyl; and m is from 0 to 2.

Preferably, in the structure as shown in formula (I) according to the present application:

$V^1$ and $V^2$ are each independently selected from hydrogen, deuterium, halogen, $C_{1-6}$ alkyl and $C_{1-6}$ alkoxy;

R is hydrogen, $C_{1-12}$ alkyl, or $C_{1-12}$ alkoxy;

L is $C_{1-12}$ alkylene;

M is selected from:

(a) hydrogen, deuterium, and $C_{2-12}$ alkyl; or (b) lithium ion, sodium ion, potassium ion, rubidium ion, cesium ion, magnesium ion, calcium ion, strontium ion, and barium ion; or (c) ammonium ion and an organic amine being protonated, wherein the organic amine comprises aliphatic amines substituted with $C_{1-12}$ alkyl, $C_{3-12}$ cycloalkyl, or $C_{3-12}$ heteroalicyclic group, the aliphatic amines being selectively substituted with one or more halogens or hydroxyls.

Preferably, in the structure as shown in formula (I) according to the present application:

$V^1$ and $V^2$ are each independently selected from hydrogen, deuterium, and halogen; and more preferably, $V^1$ and $V^2$ are identical and are hydrogen, deuterium, or halogen, and $V^1$ and $V^2$ are located in the 2-position and the 4-position of the six-membered rings substituted with them, respectively.

Preferably, in the structure as shown in formula (I) according to the present application, $V^1$ and $V^2$ are each independently selected from hydrogen, deuterium, and halogen, R is $C_{1-12}$ alkoxy, and L is $C_{1-12}$ alkylene.

Preferably, in the structure as shown in formula (I) according to the present application, $V^1$ and $V^2$ are each independently selected from hydrogen and halogen; R is methoxy, ethoxy, n-propoxy, or isopropoxy; and L is $C_{1-6}$ alkylene.

In addition, in any case mentioned above:

In the quinolyl-substituted carboxylic acid compound as shown in formula (I) or the pharmaceutically acceptable salt thereof according to the present application, M is selected from hydrogen, deuterium, and $C_{2-6}$ alkyl; or In the quinolyl-substituted carboxylic acid compound as shown in formula (I) or the pharmaceutically acceptable salt thereof according to the present application, M is selected from lithium ion, sodium ion, potassium ion, magnesium ion, and calcium ion; or In the quinolyl-substituted carboxylic acid compound as shown in formula (I) or the pharmaceutically acceptable salt thereof according to the present application, M is selected from ammonium ion, protonated methylamine, protonated ethylamine, protonated n-propylamine, protonated isopropylamine, protonated n-butylamine, protonated isobutylamine, protonated sec-butylamine, protonated tert-butylamine, protonated dimethylamine, protonated diethylamine, protonated di-n-propylamine, protonated diisopropylamine, protonated di-n-butylamine, protonated diisobutyl amine, protonated di-sec-butylamine, protonated di-tert-butylamine, protonated trimethylamine, protonated triethylamine, protonated tri-n-propylamine, protonated triisopropyl amine, protonated tri-n-butylamine, protonated triisobutylamine, protonated tri-sec-butylamine, protonated tri-tert-butylamine, protonated diisopropylethylamine, and 2-amino-2-(hydroxymethyl)propane-1,3-diol.

Specifically, with respect to the quinolyl-substituted carboxylic acid compound as shown in formula (I) or the pharmaceutically acceptable salt thereof according to the present application, the compound is selected from:

2-[[4-[2-fluoro-4-[[1-[(3-chlorophenyl)carbamoyl]cyclopropanecarbonyl]amino]phenoxy]-6-methoxy-7-quinolyl]oxy]acetic acid;

lithium 2-[[4-[2-fluoro-4-[[1-[(3-chlorophenyl)carbamoyl]cyclopropanecarbonyl]amino]phenoxy]-6-methoxy-7-quinolyl]oxy]acetate;

sodium 2-[[4-[2-fluoro-4-[[1-[(3-chlorophenyl)carbamoyl]cyclopropanecarbonyl]amino]phenoxy]-6-methoxy-7-quinolyl]oxy]acetate;

potassium 2-[[4-[2-fluoro-4-[[1-[(3-chlorophenyl)carbamoyl]cyclopropanecarbonyl]amino]phenoxy]-6-methoxy-7-quinolyl]oxy]acetate;

magnesium 2-[[4-[2-fluoro-4-[[1-[(3-chlorophenyl)carbamoyl]cyclopropanecarbonyl]amino]phenoxy]-6-methoxy-7-quinolyl]oxy]acetate;

calcium 2-[[4-[2-fluoro-4-[[1-[(3-chlorophenyl)carbamoyl]cyclopropanecarbonyl]amino]phenoxy]-6-methoxy-7-quinolyl]oxy]acetate;

ammonium 2-[[4-[2-fluoro-4-[[1-[(3-chlorophenyl)carbamoyl]cyclopropanecarbonyl]amino]phenoxy]-6-methoxy-7-quinolyl]oxy]acetate;

triethylammonium 2-[[4-[2-fluoro-4-[[1-[(3-chlorophenyl)carbamoyl]cyclopropanecarbonyl]amino]phenoxy]-6-methoxy-7-quinolyl]oxy]acetate;

1,3-dihydroxy-2-(hydroxymethyl)propan-2-ammonium 2-[[4-[2-fluoro-4-[[1-[(3-chlorophenyl)carbamoyl]cyclopropanecarbonyl]amino]phenoxy]-6-methoxy-7-quinolyl]oxy]acetate;

3-[[4-[2-fluoro-4-[[1-[(3-chlorophenyl)carbamoyl]cyclopropanecarbonyl]amino]phenoxy]-6-methoxy-7-quinolyl]oxy]propionic acid;

lithium 3-[[4-[2-fluoro-4-[[1-[(3-chlorophenyl)carbamoyl]cyclopropanecarbonyl]amino]phenoxy]-6-methoxy-7-quinolyl]oxy]propionate;

sodium 3-[[4-[2-fluoro-4-[[1-[(3-chlorophenyl)carbamoyl]cyclopropanecarbonyl]amino]phenoxy]-6-methoxy-7-quinolyl]oxy]propionate;

potassium 3-[[4-[2-fluoro-4-[[1-[(3-chlorophenyl)carbamoyl]cyclopropanecarbonyl]amino]phenoxy]-6-methoxy-7-quinolyl]oxy]propionate;

magnesium 3-[[4-[2-fluoro-4-[[1-[(3-chlorophenyl)carbamoyl]cyclopropanecarbonyl]amino]phenoxy]-6-methoxy-7-quinolyl]oxy]propionate;

calcium 3-[[4-[2-fluoro-4-[[1-[(3-chlorophenyl)carbamoyl]cyclopropanecarbonyl]amino]phenoxy]-6-methoxy-7-quinolyl]oxy]propionate;

ammonium 3-[[4-[2-fluoro-4-[[1-[(3-chlorophenyl)carbamoyl]cyclopropanecarbonyl]amino]phenoxy]-6-methoxy-7-quinolyl]oxy]propionate;

triethylammonium 3-[[4-[2-fluoro-4-[[1-[(3-chlorophenyl)carbamoyl]cyclopropanecarbonyl]amino]phenoxy]-6-methoxy-7-quinolyl]oxy]propionate;

1,3-dihydroxy-2-(hydroxymethyl)propan-2-ammonium 3-[[4-[2-fluoro-4-[[1-[(3-chlorophenyl)carbamoyl]cyclopropanecarbonyl]amino]phenoxy]-6-methoxy-7-quinolyl]oxy]propionate;

4-[[4-[2-fluoro-4-[[1-[(3-chlorophenyl)carbamoyl]cyclopropanecarbonyl]amino]phenoxy]-6-methoxy-7-quinolyl]oxy]butyric acid;

lithium 4-[[4-[2-fluoro-4-[[1-[(3-chlorophenyl)carbamoyl]cyclopropanecarbonyl]amino]phenoxy]-6-methoxy-7-quinolyl]oxy]butyrate;

sodium 4-[[4-[2-fluoro-4-[[1-[(3-chlorophenyl)carbamoyl]cyclopropanecarbonyl]amino]phenoxy]-6-methoxy-7-quinolyl]oxy]butyrate;

potassium 4-[[4-[2-fluoro-4-[[1-[(3-chlorophenyl)carbamoyl]cyclopropanecarbonyl]amino]phenoxy]-6-methoxy-7-quinolyl]oxy]butyrate;

magnesium 4-[[4-[2-fluoro-4-[[1-[(3-chlorophenyl)carbamoyl]cyclopropanecarbonyl]amino]phenoxy]-6-methoxy-7-quinolyl]oxy]butyrate;

calcium 4-[[4-[2-fluoro-4-[[1-[(3-chlorophenyl)carbamoyl]cyclopropanecarbonyl]amino]phenoxy]-6-methoxy-7-quinolyl]oxy]butyrate;

ammonium 4-[[4-[2-fluoro-4-[[1-[(3-chlorophenyl)carbamoyl]cyclopropanecarbonyl]amino]phenoxy]-6-methoxy-7-quinolyl]oxy]butyrate;

triethylammonium 4-[[4-[2-fluoro-4-[[1-[(3-chlorophenyl)carbamoyl]cyclopropanecarbonyl]amino]phenoxy]-6-methoxy-7-quinolyl]oxy]butyrate;

1,3-dihydroxy-2-(hydroxymethyl)propan-2-ammonium 4-[[4-[2-fluoro-4-[[1-[(3-chlorophenyl)carbamoyl]cyclopropanecarbonyl]amino]phenoxy]-6-methoxy-7-quinolyl]oxy]butyrate;

5-[[4-[2-fluoro-4-[[1-[(3-chlorophenyl)carbamoyl]cyclopropanecarbonyl]amino]phenoxy]-6-methoxy-7-quinolyl]oxy]valeric acid;

lithium 5-[[4-[2-fluoro-4-[[1-[(3-chlorophenyl)carbamoyl]cyclopropanecarbonyl]amino]phenoxy]-6-methoxy-7-quinolyl]oxy]valerate;

sodium 5-[[4-[2-fluoro-4-[[1-[(3-chlorophenyl)carbamoyl]cyclopropanecarbonyl]amino]phenoxy]-6-methoxy-7-quinolyl]oxy]valerate;

potassium 5-[[4-[2-fluoro-4-[[1-[(3-chlorophenyl)carbamoyl]cyclopropanecarbonyl]amino]phenoxy]-6-methoxy-7-quinolyl]oxy]valerate;

magnesium 5-[[4-[2-fluoro-4-[[1-[(3-chlorophenyl)carbamoyl]cyclopropanecarbonyl]amino]phenoxy]-6-methoxy-7-quinolyl]oxy]valerate;

calcium 5-[[4-[2-fluoro-4-[[1-[(3-chlorophenyl)carbamoyl]cyclopropanecarbonyl]amino]phenoxy]-6-methoxy-7-quinolyl]oxy]valerate;

ammonium 5-[[4-[2-fluoro-4-[[1-[(3-chlorophenyl)carbamoyl]cyclopropanecarbonyl]amino]phenoxy]-6-methoxy-7-quinolyl]oxy]valerate;

triethylammonium 5-[[4-[2-fluoro-4-[[1-[(3-chlorophenyl)carbamoyl]cyclopropanecarbonyl]amino]phenoxy]-6-methoxy-7-quinolyl]oxy]valerate;

1,3-dihydroxy-2-(hydroxymethyl)propan-2-ammonium 5-[[4-[2-fluoro-4-[[1-[(3-chlorophenyl)carbamoyl]cyclopropanecarbonyl]amino]phenoxy]-6-methoxy-7-quinolyl]oxy]valerate;

6-[[4-[2-fluoro-4-[[1-[(3-chlorophenyl)carbamoyl]cyclopropanecarbonyl]amino]phenoxy]-6-methoxy-7-quinolyl]oxy]caproic acid;

lithium 6-[[4-[2-fluoro-4-[[1-[(3-chlorophenyl)carbamoyl]cyclopropanecarbonyl]amino]phenoxy]-6-methoxy-7-quinolyl]oxy]caproate;

sodium 6-[[4-[2-fluoro-4-[[1-[(3-chlorophenyl)carbamoyl]cyclopropanecarbonyl]amino]phenoxy]-6-methoxy-7-quinolyl]oxy]caproate;

potassium 6-[[4-[2-fluoro-4-[[1-[(3-chlorophenyl)carbamoyl]cyclopropanecarbonyl]amino]phenoxy]-6-methoxy-7-quinolyl]oxy]caproate;

magnesium 6-[[4-[2-fluoro-4-[[1-[(3-chlorophenyl)carbamoyl]cyclopropanecarbonyl]amino]phenoxy]-6-methoxy-7-quinolyl]oxy]caproate;

calcium 6-[[4-[2-fluoro-4-[[1-[(3-chlorophenyl)carbamoyl]cyclopropanecarbonyl]amino]phenoxy]-6-methoxy-7-quinolyl]oxy]caproate;

ammonium 6-[[4-[2-fluoro-4-[[1-[(3-chlorophenyl)carbamoyl]cyclopropanecarbonyl]amino]phenoxy]-6-methoxy-7-quinolyl]oxy]caproate;

triethylammonium 6-[[4-[2-fluoro-4-[[1-[(3-chlorophenyl)carbamoyl]cyclopropanecarbonyl]amino]phenoxy]-6-methoxy-7-quinolyl]oxy]caproate;

1,3-dihydroxy-2-(hydroxymethyl)propan-2-ammonium 6-[[4-[2-fluoro-4-[[1-[(3-chlorophenyl)carbamoyl]cyclopropanecarbonyl]amino]phenoxy]-6-methoxy-7-quinolyl]oxy]caproate;

7-[[4-[2-fluoro-4-[[1-[(3-chlorophenyl)carbamoyl]cyclopropanecarbonyl]amino]phenoxy]-6-methoxy-7-quinolyl]oxy]heptanoic acid;

lithium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

sodium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

potassium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

magnesium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

calcium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

ammonium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

triethylammonium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

1,3-dihydroxy-2-(hydroxymethyl)propan-2-ammonium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

2-[[4-[2-fluoro-4-[[1-[(4-fluorophenyl)carbamoyl]cyclopropanecarbonyl]amino]phenoxy]-6-methoxy-7-quinolyl]oxy]acetic acid;

lithium 2-[[4-[2-fluoro-4-[[1-[(4-fluorophenyl)carbamoyl]cyclopropanecarbonyl]amino]phenoxy]-6-methoxy-7-quinolyl]oxy]acetate;

sodium 2-[[4-[2-fluoro-4-[[1-[(4-fluorophenyl)carbamoyl]cyclopropanecarbonyl]amino]phenoxy]-6-methoxy-7-quinolyl]oxy]acetate;

potassium 2-[[4-[2-fluoro-4-[[1-[(4-fluorophenyl)carbamoyl]cyclopropanecarbonyl]amino]phenoxy]-6-methoxy-7-quinolyl]oxy]acetate;

magnesium 2-[[4-[2-fluoro-4-[[1-[(4-fluorophenyl)carbamoyl]cyclopropanecarbonyl]amino]phenoxy]-6-methoxy-7-quinolyl]oxy]acetate;

calcium 2-[[4-[2-fluoro-4-[[1-[(4-fluorophenyl)carbamoyl]cyclopropanecarbonyl]amino]phenoxy]-6-methoxy-7-quinolyl]oxy]acetate;

ammonium 2-[[4-[2-fluoro-4-[[1-[(4-fluorophenyl)carbamoyl]cyclopropanecarbonyl]amino]phenoxy]-6-methoxy-7-quinolyl]oxy]acetate;

triethylammonium 2-[[4-[2-fluoro-4-[[1-[(4-fluorophenyl)carbamoyl]cyclopropanecarbonyl]amino]phenoxy]-6-methoxy-7-quinolyl]oxy]acetate;

1,3-dihydroxy-2-(hydroxymethyl)propan-2-ammonium 2-[[4-[2-fluoro-4-[[1-[(4-fluorophenyl)carbamoyl]cyclopropanecarbonyl]amino]phenoxy]-6-methoxy-7-quinolyl]oxy]acetate;

3-[[4-[2-fluoro-4-[[1-[(4-fluorophenyl)carbamoyl]cyclopropanecarbonyl]amino]phenoxy]-6-methoxy-7-quinolyl]oxy]propionic acid;

lithium 3-[[4-[2-fluoro-4-[[1-[(4-fluorophenyl)carbamoyl]cyclopropanecarbonyl]amino]phenoxy]-6-methoxy-7-quinolyl]oxy]propionate;

sodium 3-[[4-[2-fluoro-4-[[1-[(4-fluorophenyl)carbamoyl]cyclopropanecarbonyl]amino]phenoxy]-6-methoxy-7-quinolyl]oxy]propionate;

potassium 3-[[4-[2-fluoro-4-[[1-[(4-fluorophenyl)carbamoyl]cyclopropanecarbonyl]amino]phenoxy]-6-methoxy-7-quinolyl]oxy]propionate;

magnesium 3-[[4-[2-fluoro-4-[[1-[(4-fluorophenyl)carbamoyl]cyclopropanecarbonyl]amino]phenoxy]-6-methoxy-7-quinolyl]oxy]propionate;

calcium 3-[[4-[2-fluoro-4-[[1-[(4-fluorophenyl)carbamoyl]cyclopropanecarbonyl]amino]phenoxy]-6-methoxy-7-quinolyl]oxy]propionate;

ammonium 3-[[4-[2-fluoro-4-[[1-[(4-fluorophenyl)carbamoyl]cyclopropanecarbonyl]amino]phenoxy]-6-methoxy-7-quinolyl]oxy]propionate;

triethylammonium 3-[[4-[2-fluoro-4-[[1-[(4-fluorophenyl)carbamoyl]cyclopropanecarbonyl]amino]phenoxy]-6-methoxy-7-quinolyl]oxy]propionate;

1,3-dihydroxy-2-(hydroxymethyl)propan-2-ammonium 3-[[4-[2-fluoro-4-[[1-[(4-fluorophenyl)carbamoyl]cyclopropanecarbonyl]amino]phenoxy]-6-methoxy-7-quinolyl]oxy]propionate;

4-[[4-[2-fluoro-4-[[1-[(4-fluorophenyl)carbamoyl]cyclopropanecarbonyl]amino]phenoxy]-6-methoxy-7-quinolyl]oxy]butyric acid;

lithium 4-[[4-[2-fluoro-4-[[1-[(4-fluorophenyl)carbamoyl]cyclopropanecarbonyl]amino]phenoxy]-6-methoxy-7-quinolyl]oxy]butyrate;

sodium 4-[[4-[2-fluoro-4-[[1-[(4-fluorophenyl)carbamoyl]cyclopropanecarbonyl]amino]phenoxy]-6-methoxy-7-quinolyl]oxy]butyrate;
potassium 4-[[4-[2-fluoro-4-[[1-[(4-fluorophenyl)carbamoyl]cyclopropanecarbonyl]amino]phenoxy]-6-methoxy-7-quinolyl]oxy]butyrate;
magnesium 4-[[4-[2-fluoro-4-[[1-[(4-fluorophenyl)carbamoyl]cyclopropanecarbonyl]amino]phenoxy]-6-methoxy-7-quinolyl]oxy]butyrate;
calcium 4-[[4-[2-fluoro-4-[[1-[(4-fluorophenyl)carbamoyl]cyclopropanecarbonyl]amino]phenoxy]-6-methoxy-7-quinolyl]oxy]butyrate;
ammonium 4-[[4-[2-fluoro-4-[[1-[(4-fluorophenyl)carbamoyl]cyclopropanecarbonyl]amino]phenoxy]-6-methoxy-7-quinolyl]oxy]butyrate;
triethylammonium 4-[[4-[2-fluoro-4-[[1-[(4-fluorophenyl)carbamoyl]cyclopropanecarbonyl]amino]phenoxy]-6-methoxy-7-quinolyl]oxy]butyrate;
1,3-dihydroxy-2-(hydroxymethyl)propan-2-ammonium 4-[[4-[2-fluoro-4-[[1-[(4-fluorophenyl)carbamoyl]cyclopropanecarbonyl]amino]phenoxy]-6-methoxy-7-quinolyl]oxy]butyrate;
5-[[4-[2-fluoro-4-[[1-[(4-fluorophenyl)carbamoyl]cyclopropanecarbonyl]amino]phenoxy]-6-methoxy-7-quinolyl]oxy]valeric acid;
lithium 5-[[4-[2-fluoro-4-[[1-[(4-fluorophenyl)carbamoyl]cyclopropanecarbonyl]amino]phenoxy]-6-methoxy-7-quinolyl]oxy]valerate;
sodium 5-[[4-[2-fluoro-4-[[1-[(4-fluorophenyl)carbamoyl]cyclopropanecarbonyl]amino]phenoxy]6-methoxy-7-quinolyl]oxy]valerate;
potassium 5-[[4-[2-fluoro-4-[[1-[(4-fluorophenyl)carbamoyl]cyclopropanecarbonyl]amino]phenoxy]-6-methoxy-7-quinolyl]oxy]valerate;
magnesium 5-[[4-[2-fluoro-4-[[1-[(4-fluorophenyl)carbamoyl]cyclopropanecarbonyl]amino]phenoxy]-6-methoxy-7-quinolyl]oxy]valerate;
calcium 5-[[4-[2-fluoro-4-[[1-[(4-fluorophenyl)carbamoyl]cyclopropanecarbonyl]amino]phenoxy]-6-methoxy-7-quinolyl]oxy]valerate;
ammonium 5-[[4-[2-fluoro-4-[[1-[(4-fluorophenyl)carbamoyl]cyclopropanecarbonyl]amino]phenoxy]-6-methoxy-7-quinolyl]oxy]valerate;
triethylammonium 5-[[4-[2-fluoro-4-[[1-[(4-fluorophenyl)carbamoyl]cyclopropanecarbonyl]amino]phenoxy]-6-methoxy-7-quinolyl]oxy]valerate;
1,3-dihydroxy-2-(hydroxymethyl)propan-2-ammonium 5-[[4-[2-fluoro-4-[[1-[(4-fluorophenyl)carbamoyl]cyclopropanecarbonyl]amino]phenoxy]-6-methoxy-7-quinolyl]oxy]valerate;
6-[[4-[2-fluoro-4-[[1-[(4-fluorophenyl)carbamoyl]cyclopropanecarbonyl]amino]phenoxy]-6-methoxy-7-quinolyl]oxy]caproic acid;
lithium 6-[[4-[2-fluoro-4-[[1-[(4-fluorophenyl)carbamoyl]cyclopropanecarbonyl]amino]phenoxy]-6-methoxy-7-quinolyl]oxy]caproate;
sodium 6-[[4-[2-fluoro-4-[[1-[(4-fluorophenyl)carbamoyl]cyclopropanecarbonyl]amino]phenoxy]-6-methoxy-7-quinolyl]oxy]caproate;
potassium 6-[[4-[2-fluoro-4-[[1-[(4-fluorophenyl)carbamoyl]cyclopropanecarbonyl]amino]phenoxy]-6-methoxy-7-quinolyl]oxy]caproate;
magnesium 6-[[4-[2-fluoro-4-[[1-[(4-fluorophenyl)carbamoyl]cyclopropanecarbonyl]amino]phenoxy]-6-methoxy-7-quinolyl]oxy]caproate;
calcium 6-[[4-[2-fluoro-4-[[1-[(4-fluorophenyl)carbamoyl]cyclopropanecarbonyl]amino]phenoxy]-6-methoxy-7-quinolyl]oxy]caproate;
ammonium 6-[[4-[2-fluoro-4-[[1-[(4-fluorophenyl)carbamoyl]cyclopropanecarbonyl]amino]phenoxy]-6-methoxy-7-quinolyl]oxy]caproate;
triethylammonium 6-[[4-[2-fluoro-4-[[1-[(4-fluorophenyl)carbamoyl]cyclopropanecarbonyl]amino]phenoxy]-6-methoxy-7-quinolyl]oxy]caproate;
1,3-dihydroxy-2-(hydroxymethyl)propan-2-ammonium 6-[[4-[2-fluoro-4-[[1-[(4-fluorophenyl)carbamoyl]cyclopropanecarbonyl]amino]phenoxy]-6-methoxy-7-quinolyl]oxy]caproate;
7-[[4-[2-fluoro-4-[[1-[(4-fluorophenyl)carbamoyl]cyclopropanecarbonyl]amino]phenoxy]-6-methoxy-7-quinolyl]oxy]heptanoic acid;
lithium 7-[[4-[2-fluoro-4-[[1-[(4-fluorophenyl)carbamoyl]cyclopropanecarbonyl]amino]phenoxy]-6-methoxy-7-quinolyl]oxy]heptanoate;
sodium 7-[[4-[2-fluoro-4-[[1-[(4-fluorophenyl)carbamoyl]cyclopropanecarbonyl]amino]phenoxy]-6-methoxy-7-quinolyl]oxy]heptanoate;
potassium 7-[[4-[2-fluoro-4-[[1-[(4-fluorophenyl)carbamoyl]cyclopropanecarbonyl]amino]phenoxy]-6-methoxy-7-quinolyl]oxy]heptanoate;
magnesium 7-[[4-[2-fluoro-4-[[1-[(4-fluorophenyl)carbamoyl]cyclopropanecarbonyl]amino]phenoxy]-6-methoxy-7-quinolyl]oxy]heptanoate;
calcium 7-[[4-[2-fluoro-4-[[1-[(4-fluorophenyl)carbamoyl]cyclopropanecarbonyl]amino]phenoxy]-6-methoxy-7-quinolyl]oxy]heptanoate;
ammonium 7-[[4-[2-fluoro-4-[[1-[(4-fluorophenyl)carbamoyl]cyclopropanecarbonyl]amino]phenoxy]-6-methoxy-7-quinolyl]oxy]heptanoate;
triethylammonium 7-[[4-[2-fluoro-4-[[1-[(4-fluorophenyl)carbamoyl]cyclopropanecarbonyl]amino]phenoxy]-6-methoxy-7-quinolyl]oxy]heptanoate;
1,3-dihydroxy-2-(hydroxymethyl)propan-2-ammonium 7-[[4-[2-fluoro-4-[[1-[(4-fluorophenyl)carbamoyl]cyclopropanecarbonyl]amino]phenoxy]-6-methoxy-7-quinolyl]oxy]heptanoate;
2-[[4-[2-chloro-[[1-[(4-fluorophenyl)carbamoyl]cyclopropanecarbonyl]amino]phenoxy]-6-methoxy-7-quinolyl]oxy]acetic acid;
lithium 2-[[4-[2-chloro-[[1-[(4-fluorophenyl)carbamoyl]cyclopropanecarbonyl]amino]phenoxy]-6-methoxy-7-quinolyl]oxy]acetate;
sodium 2-[[4-[2-chloro-[[1-[(4-fluorophenyl)carbamoyl]cyclopropanecarbonyl]amino]phenoxy]-6-methoxy-7-quinolyl]oxy]acetate;
potassium 2-[[4-[2-chloro-[[1-[(4-fluorophenyl)carbamoyl]cyclopropanecarbonyl]amino]phenoxy]-6-methoxy-7-quinolyl]oxy]acetate;
magnesium 2-[[4-[2-chloro-[[1-[(4-fluorophenyl)carbamoyl]cyclopropanecarbonyl]amino]phenoxy]-6-methoxy-7-quinolyl]oxy]acetate;
calcium 2-[[4-[2-chloro-[[1-[(4-fluorophenyl)carbamoyl]cyclopropanecarbonyl]amino]phenoxy]-6-methoxy-7-quinolyl]oxy]acetate;
ammonium 2-[[4-[2-chloro-[[1-[(4-fluorophenyl)carbamoyl]cyclopropanecarbonyl]amino]phenoxy]-6-methoxy-7-quinolyl]oxy]acetate;
triethylammonium 2-[[4-[2-chloro-[[1-[(4-fluorophenyl)carbamoyl]cyclopropanecarbonyl]amino]phenoxy]-6-methoxy-7-quinolyl]oxy]acetate;

1,3-dihydroxy-2-(hydroxymethyl)propan-2-ammonium 2-[[4-[2-chloro-[[1-[(4-fluorophenyl)carbamoyl]cyclopropanecarbonyl]amino]phenoxy]-6-methoxy-7-quinolyl]oxy]acetate;
3-[[4-[2-chloro-[[1-[(4-fluorophenyl)carbamoyl]cyclopropanecarbonyl]amino]phenoxy]-6-methoxy-7-quinolyl]oxy]propionic acid;
lithium 3-[[4-[2-chloro-[[1-[(4-fluorophenyl)carbamoyl]cyclopropanecarbonyl]amino]phenoxy]-6-methoxy-7-quinolyl]oxy]propionate;
sodium 3-[[4-[2-chloro-[[1-[(4-fluorophenyl)carbamoyl]cyclopropanecarbonyl]amino]phenoxy]-6-methoxy-7-quinolyl]oxy]propionate;
potassium 3-[[4-[2-chloro-[[1-[(4-fluorophenyl)carbamoyl]cyclopropanecarbonyl]amino]phenoxy]-6-methoxy-7-quinolyl]oxy]propionate;
magnesium 3-[[4-[2-chloro-4-[[1-[(4-fluorophenyl)carbamoyl]cyclopropanecarbonyl]amino]phenoxy]-6-methoxy-7-quinolyl]oxy]propionate;
calcium 3-[[4-[2-chloro-[[1-[(4-fluorophenyl)carbamoyl]cyclopropanecarbonyl]amino]phenoxy]-6-methoxy-7-quinolyl]oxy]propionate;
ammonium 3-[[4-[2-chloro-[[1-[(4-fluorophenyl)carbamoyl]cyclopropanecarbonyl]amino]phenoxy]-6-methoxy-7-quinolyl]oxy]propionate;
triethylammonium 3-[[4-[2-chloro-[[1-[(4-fluorophenyl)carbamoyl]cyclopropanecarbonyl]amino]phenoxy]-6-methoxy-7-quinolyl]oxy]propionate;
1,3-dihydroxy-2-(hydroxymethyl)propan-2-ammonium 3-[[4-[2-chloro-[[1-[(4-fluorophenyl)carbamoyl]cyclopropanecarbonyl]amino]phenoxy]-6-methoxy-7-quinolyl]oxy]propionate;
4-[[4-[2-chloro-[[1-[(4-fluorophenyl)carbamoyl]cyclopropanecarbonyl]amino]phenoxy]-6-methoxy-7-quinolyl]oxy]butyric acid;
lithium 4-[[4-[2-chloro-[[1-[(4-fluorophenyl)carbamoyl]cyclopropanecarbonyl]amino]phenoxy]-6-methoxy-7-quinolyl]oxy]butyrate;
sodium 4-[[4-[2-chloro-[[1-[(4-fluorophenyl)carbamoyl]cyclopropanecarbonyl]amino]phenoxy]-6-methoxy-7-quinolyl]oxy]butyrate;
potassium 4-[[4-[2-chloro-[[1-[(4-fluorophenyl)carbamoyl]cyclopropanecarbonyl]amino]phenoxy]-6-methoxy-7-quinolyl]oxy]butyrate;
magnesium 4-[[4-[2-chloro-[[1-[(4-fluorophenyl)carbamoyl]cyclopropanecarbonyl]amino]phenoxy]-6-methoxy-7-quinolyl]oxy]butyrate;
calcium 4-[[4-[2-chloro-[[1-[(4-fluorophenyl)carbamoyl]cyclopropanecarbonyl]amino]phenoxy]-6-methoxy-7-quinolyl]oxy]butyrate;
ammonium 4-[[4-[2-chloro-[[1-[(4-fluorophenyl)carbamoyl]cyclopropanecarbonyl]amino]phenoxy]-6-methoxy-7-quinolyl]oxy]butyrate;
triethylammonium 4-[[4-[2-chloro-[[1-[(4-fluorophenyl)carbamoyl]cyclopropanecarbonyl]amino]phenoxy]-6-methoxy-7-quinolyl]oxy]butyrate;
1,3-dihydroxy-2-(hydroxymethyl)propan-2-ammonium 4-[[4-[2-chloro-[[1-[(4-fluorophenyl)carbamoyl]cyclopropanecarbonyl]amino]phenoxy]-6-methoxy-7-quinolyl]oxy]butyrate;
5-[[4-[2-chloro-[[1-[(4-fluorophenyl)carbamoyl]cyclopropanecarbonyl]amino]phenoxy]-6-methoxy-7-quinolyl]oxy]valeric acid;
lithium 5-[[4-[2-chloro-[[1-[(4-fluorophenyl)carbamoyl]cyclopropanecarbonyl]amino]phenoxy]-6-methoxy-7-quinolyl]oxy]valerate;
sodium 5-[[4-[2-chloro-[[1-[(4-fluorophenyl)carbamoyl]cyclopropanecarbonyl]amino]phenoxy]-6-methoxy-7-quinolyl]oxy]valerate;
potassium 5-[[4-[2-chloro-[[1-[(4-fluorophenyl)carbamoyl]cyclopropanecarbonyl]amino]phenoxy]-6-methoxy-7-quinolyl]oxy]valerate;
magnesium 5-[[4-[2-chloro-[[1-[(4-fluorophenyl)carbamoyl]cyclopropanecarbonyl]amino]phenoxy]-6-methoxy-7-quinolyl]oxy]valerate;
calcium 5-[[4-[2-chloro-[[1-[(4-fluorophenyl)carbamoyl]cyclopropanecarbonyl]amino]phenoxy]-6-methoxy-7-quinolyl]oxy]valerate;
ammonium 5-[[4-[2-chloro-[[1-[(4-fluorophenyl)carbamoyl]cyclopropanecarbonyl]amino]phenoxy]-6-methoxy-7-quinolyl]oxy]heptanoate;
triethylammonium 5-[[4-[2-chloro-[[1-[(4-fluorophenyl)carbamoyl]cyclopropanecarbonyl]amino]phenoxy]-6-methoxy-7-quinolyl]oxy]valerate;
1,3-dihydroxy-2-(hydroxymethyl)propan-2-ammonium 5-[[4-[2-chloro-[[1-[(4-fluorophenyl)carbamoyl]cyclopropanecarbonyl]amino]phenoxy]-6-methoxy-7-quinolyl]oxy]valerate;
6-[[4-[2-chloro-[[1-[(4-fluorophenyl)carbamoyl]cyclopropanecarbonyl]amino]phenoxy]-6-methoxy-7-quinolyl]oxy]caproic acid;
lithium 6-[[4-[2-chloro-[[1-[(4-fluorophenyl)carbamoyl]cyclopropanecarbonyl]amino]phenoxy]-6-methoxy-7-quinolyl]oxy]caproate;
sodium 6-[[4-[2-chloro-[[1-[(4-fluorophenyl)carbamoyl]cyclopropanecarbonyl]amino]phenoxy]-6-methoxy-7-quinolyl]oxy]caproate;
potassium 6-[[4-[2-chloro-[[1-[(4-fluorophenyl)carbamoyl]cyclopropanecarbonyl]amino]phenoxy]-6-methoxy-7-quinolyl]oxy]caproate;
magnesium 6-[[4-[2-chloro-[[1-[(4-fluorophenyl)carbamoyl]cyclopropanecarbonyl]amino]phenoxy]-6-methoxy-7-quinolyl]oxy]caproate;
calcium 6-[[4-[2-chloro-[[1-[(4-fluorophenyl)carbamoyl]cyclopropanecarbonyl]amino]phenoxy]-6-methoxy-7-quinolyl]oxy]caproate;
ammonium 6-[[4-[2-chloro-[[1-[(4-fluorophenyl)carbamoyl]cyclopropanecarbonyl]amino]phenoxy]-6-methoxy-7-quinolyl]oxy]caproate;
triethylammonium 6-[[4-[2-chloro-[[1-[(4-fluorophenyl)carbamoyl]cyclopropanecarbonyl]amino]phenoxy]-6-methoxy-7-quinolyl]oxy]caproate;
1,3-dihydroxy-2-(hydroxymethyl)propan-2-ammonium 6-[[4-[2-chloro-[[1-[(4-fluorophenyl)carbamoyl]cyclopropanecarbonyl]amino]phenoxy]-6-methoxy-7-quinolyl]oxy]caproate;
7-[[4-[2-chloro-[[1-[(4-fluorophenyl)carbamoyl]cyclopropanecarbonyl]amino]phenoxy]-6-methoxy-7-quinolyl]oxy]heptanoic acid;
lithium 7-[[4-[2-chloro-[[1-[(4-fluorophenyl)carbamoyl]cyclopropanecarbonyl]amino]phenoxy]-6-methoxy-7-quinolyl]oxy]heptanoate;
sodium 7-[[4-[2-chloro-[[1-[(4-fluorophenyl)carbamoyl]cyclopropanecarbonyl]amino]phenoxy]-6-methoxy-7-quinolyl]oxy]heptanoate;
potassium 7-[[4-[2-chloro-[[1-[(4-fluorophenyl)carbamoyl]cyclopropanecarbonyl]amino]phenoxy]-6-methoxy-7-quinolyl]oxy]heptanoate;
magnesium 7-[[4-[2-chloro-[[1-[(4-fluorophenyl)carbamoyl]cyclopropanecarbonyl]amino]phenoxy]-6-methoxy-7-quinolyl]oxy]heptanoate;

calcium 7-[[4-[2-chloro-[[1-[(4-fluorophenyl)carbamoyl]cyclopropanecarbonyl]amino]phenoxy]-6-methoxy-7-quinolyl]oxy]heptanoate;
ammonium 7-[[4-[2-chloro-[[1-[(4-fluorophenyl)carbamoyl]cyclopropanecarbonyl]amino]phenoxy]-6-methoxy-7-quinolyl]oxy]heptanoate;
triethylammonium 7-[[4-[2-chloro-[[1-[(4-fluorophenyl)carbamoyl]cyclopropanecarbonyl]amino]phenoxy]-6-methoxy-7-quinolyl]oxy]heptanoate;
1,3-dihydroxy-2-(hydroxymethyl)propan-2-ammonium 7-[[4-[2-chloro-[[1-[(4-fluorophenyl)carbamoyl]cyclopropanecarbonyl]amino]phenoxy]-6-methoxy-7-quinolyl]oxy]heptanoate;
2-[[4-[2-fluoro-4-[[1-[(4-fluorophenyl)carbamoyl]cyclopropanecarbonyl]amino]phenoxy]-6-ethoxy-7-quinolyl]oxy]acetic acid;
lithium 2-[[4-[2-fluoro-4-[[1-[(4-fluorophenyl)carbamoyl]cyclopropanecarbonyl]amino]phenoxy]-6-ethoxy-7-quinolyl]oxy]acetate;
sodium 2-[[4-[2-fluoro-4-[[1-[(4-fluorophenyl)carbamoyl]cyclopropanecarbonyl]amino]phenoxy]-6-ethoxy-7-quinolyl]oxy]acetate;
potassium 2-[[4-[2-fluoro-4-[[1-[(4-fluorophenyl)carbamoyl]cyclopropanecarbonyl]amino]phenoxy]-6-ethoxy-7-quinolyl]oxy]acetate;
magnesium 2-[[4-[2-fluoro-4-[[1-[(4-fluorophenyl)carbamoyl]cyclopropanecarbonyl]amino]phenoxy]-6-ethoxy-7-quinolyl]oxy]acetate;
calcium 2-[[4-[2-fluoro-4-[[1-[(4-fluorophenyl)carbamoyl]cyclopropanecarbonyl]amino]phenoxy]-6-ethoxy-7-quinolyl]oxy]acetate;
ammonium 2-[[4-[2-fluoro-4-[[1-[(4-fluorophenyl)carbamoyl]cyclopropanecarbonyl]amino]phenoxy]-6-ethoxy-7-quinolyl]oxy]acetate;
triethylammonium 2-[[4-[2-fluoro-4-[[1-[(4-fluorophenyl)carbamoyl]cyclopropanecarbonyl]amino]phenoxy]-6-ethoxy-7-quinolyl]oxy]acetate;
1,3-dihydroxy-2-(hydroxymethyl)propan-2-ammonium 2-[[4-[2-fluoro-4-[[1-[(4-fluorophenyl)carbamoyl]cyclopropanecarbonyl]amino]phenoxy]-6-ethoxy-7-quinolyl]oxy]acetate;
3-[[4-[2-fluoro-4-[[1-[(4-fluorophenyl)carbamoyl]cyclopropanecarbonyl]amino]phenoxy]-6-ethoxy-7-quinolyl]oxy]propionic acid;
lithium 3-[[4-[2-fluoro-4-[[1-[(4-fluorophenyl)carbamoyl]cyclopropanecarbonyl]amino]phenoxy]-6-ethoxy-7-quinolyl]oxy]propionate;
sodium 3-[[4-[2-fluoro-4-[[1-[(4-fluorophenyl)carbamoyl]cyclopropanecarbonyl]amino]phenoxy]-6-ethoxy-7-quinolyl]oxy]propionate;
potassium 3-[[4-[2-fluoro-4-[[1-[(4-fluorophenyl)carbamoyl]cyclopropanecarbonyl]amino]phenoxy]-6-ethoxy-7-quinolyl]oxy]propionate;
magnesium 3-[[4-[2-fluoro-4-[[1-[(4-fluorophenyl)carbamoyl]cyclopropanecarbonyl]amino]phenoxy]-6-ethoxy-7-quinolyl]oxy]propionate;
calcium 3-[[4-[2-fluoro-4-[[1-[(4-fluorophenyl)carbamoyl]cyclopropanecarbonyl]amino]phenoxy]-6-ethoxy-7-quinolyl]oxy]propionate;
ammonium 3-[[4-[2-fluoro-4-[[1-[(4-fluorophenyl)carbamoyl]cyclopropanecarbonyl]amino]phenoxy]-6-ethoxy-7-quinolyl]oxy]propionate;
triethylammonium 3-[[4-[2-fluoro-4-[[1-[(4-fluorophenyl)carbamoyl]cyclopropanecarbonyl]amino]phenoxy]-6-ethoxy-7-quinolyl]oxy]propionate;
1,3-dihydroxy-2-(hydroxymethyl)propan-2-ammonium 3-[[4-[2-fluoro-4-[[1-[(4-fluorophenyl)carbamoyl]cyclopropanecarbonyl]amino]phenoxy]-6-ethoxy-7-quinolyl]oxy]propionate;
4-[[4-[2-fluoro-4-[[1-[(4-fluorophenyl)carbamoyl]cyclopropanecarbonyl]amino]phenoxy]-6-ethoxy-7-quinolyl]oxy]butyric acid;
lithium 4-[[4-[2-fluoro-4-[[1-[(4-fluorophenyl)carbamoyl]cyclopropanecarbonyl]amino]phenoxy]-6-ethoxy-7-quinolyl]oxy]butyrate;
sodium 4-[[4-[2-fluoro-4-[[1-[(4-fluorophenyl)carbamoyl]cyclopropanecarbonyl]amino]phenoxy]-6-methoxy-7-quinolyl]oxy]butyrate;
potassium 4-[[4-[2-fluoro-4-[[1-[(4-fluorophenyl)carbamoyl]cyclopropanecarbonyl]amino]phenoxy]-6-ethoxy-7-quinolyl]oxy]butyrate;
magnesium 4-[[4-[2-fluoro-4-[[1-[(4-fluorophenyl)carbamoyl]cyclopropanecarbonyl]amino]phenoxy]-6-ethoxy-7-quinolyl]oxy]butyrate;
calcium 4-[[4-[2-fluoro-4-[[1-[(4-fluorophenyl)carbamoyl]cyclopropanecarbonyl]amino]phenoxy]-6-ethoxy-7-quinolyl]oxy]butyrate;
ammonium 4-[[4-[2-fluoro-4-[[1-[(4-fluorophenyl)carbamoyl]cyclopropanecarbonyl]amino]phenoxy]-6-ethoxy-7-quinolyl]oxy]butyrate;
triethylammonium 4-[[4-[2-fluoro-4-[[1-[(4-fluorophenyl)carbamoyl]cyclopropanecarbonyl]amino]phenoxy]-6-ethoxy-7-quinolyl]oxy]butyrate;
1,3-dihydroxy-2-(hydroxymethyl)propan-2-ammonium 4-[[4-[2-fluoro-4-[[1-[(4-fluorophenyl)carbamoyl]cyclopropanecarbonyl]amino]phenoxy]-6-ethoxy-7-quinolyl]oxy]butyrate;
5-[[4-[2-fluoro-4-[[1-[(4-fluorophenyl)carbamoyl]cyclopropanecarbonyl]amino]phenoxy]-6-ethoxy-7-quinolyl]oxy]valeric acid;
lithium 5-[[4-[2-fluoro-4-[[1-[(4-fluorophenyl)carbamoyl]cyclopropanecarbonyl]amino]phenoxy]-6-ethoxy-7-quinolyl]oxy]valerate;
sodium 5-[[4-[2-fluoro-4-[[1-[(4-fluorophenyl)carbamoyl]cyclopropanecarbonyl]amino]phenoxy]-6-methoxy-7-quinolyl]oxy]valerate;
potassium 5-[[4-[2-fluoro-4-[[1-[(3-chlorophenyl)carbamoyl]cyclopropanecarbonyl]amino]phenoxy]-6-methoxy-7-quinolyl]oxy]valerate;
magnesium 5-[[4-[2-fluoro-4-[[1-[(4-fluorophenyl)carbamoyl]cyclopropanecarbonyl]amino]phenoxy]-6-ethoxy-7-quinolyl]oxy]valerate;
calcium 5-[[4-[2-fluoro-4-[[1-[(4-fluorophenyl)carbamoyl]cyclopropanecarbonyl]amino]phenoxy]-6-ethoxy-7-quinolyl]oxy]valerate;
ammonium 5-[[4-[2-fluoro-4-[[1-[(4-fluorophenyl)carbamoyl]cyclopropanecarbonyl]amino]phenoxy]-6-ethoxy-7-quinolyl]oxy]valerate;
triethylammonium 5-[[4-[2-fluoro-4-[[1-[(4-fluorophenyl)carbamoyl]cyclopropanecarbonyl]amino]phenoxy]-6-ethoxy-7-quinolyl]oxy]valerate;
1,3-dihydroxy-2-(hydroxymethyl)propan-2-ammonium 5-[[4-[2-fluoro-4-[[1-[(4-fluorophenyl)carbamoyl]cyclopropanecarbonyl]amino]phenoxy]-6-ethoxy-7-quinolyl]oxy]valerate;
6-[[4-[2-fluoro-4-[[1-[(4-fluorophenyl)carbamoyl]cyclopropanecarbonyl]amino]phenoxy]-6-ethoxy-7-quinolyl]oxy]caproic acid;
lithium 6-[[4-[2-fluoro-4-[[1-[(4-fluorophenyl)carbamoyl]cyclopropanecarbonyl]amino]phenoxy]-6-ethoxy-7-quinolyl]oxy]caproate;

sodium 6-[[4-[2-fluoro-4-[[1-[(4-fluorophenyl)carbamoyl]cyclopropanecarbonyl]amino]phenoxy]-6-ethoxy-7-quinolyl]oxy]caproate;
potassium 6-[[4-[2-fluoro-4-[[1-[(4-chlorophenyl)carbamoyl]cyclopropanecarbonyl]amino]phenoxy]-6-ethoxy-7-quinolyl]oxy]caproate;
magnesium 6-[[4-[2-fluoro-4-[[1-[(4-fluorophenyl)carbamoyl]cyclopropanecarbonyl]amino]phenoxy]-6-ethoxy-7-quinolyl]oxy]caproate;
calcium 6-[[4-[2-fluoro-4-[[1-[(4-fluorophenyl)carbamoyl]cyclopropanecarbonyl]amino]phenoxy]-6-ethoxy-7-quinolyl]oxy]caproate;
ammonium 6-[[4-[2-fluoro-4-[[1-[(4-fluorophenyl)carbamoyl]cyclopropanecarbonyl]amino]phenoxy]-6-ethoxy-7-quinolyl]oxy]caproate;
triethylammonium 6-[[4-[2-fluoro-4-[[1-[(4-fluorophenyl)carbamoyl]cyclopropanecarbonyl]amino]phenoxy]-6-ethoxy-7-quinolyl]oxy]caproate;
1,3-dihydroxy-2-(hydroxymethyl)propan-2-ammonium 6-[[4-[2-fluoro-4-[[1-[(4-fluorophenyl)carbamoyl]cyclopropanecarbonyl]amino]phenoxy]-6-ethoxy-7-quinolyl]oxy]caproate;
7-[[4-[2-fluoro-4-[[1-[(4-fluorophenyl)carbamoyl]cyclopropanecarbonyl]amino]phenoxy]-6-ethoxy-7-quinolyl]oxy]heptanoic acid;
lithium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
sodium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
potassium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
magnesium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
calcium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
ammonium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
triethylammonium 7-[[4-[2-fluoro-4-[[1-[(4-fluorophenyl)carbamoyl]cyclopropanecarbonyl]amino]phenoxy]-6-ethoxy-7-quinolyl]oxy]heptanoate; and
1,3-dihydroxy-2-(hydroxymethyl)propan-2-ammonium 7-[[4-[2-fluoro-4-[[1-[(4-fluorophenyl)carbamoyl]cyclopropanecarbonyl]amino]phenoxy]-6-ethoxy-7-quinolyl]oxy]heptanoate.

The present application also protects a racemate or an enantiomer of any quinolyl-substituted carboxylic acid compound or any pharmaceutically acceptable salt thereof as mentioned above.

The present application also protects a method for preparing a quinolyl-substituted carboxylic acid compound or a pharmaceutically acceptable salt thereof. The method includes, but is not limited to, the following steps shown in Scheme 1:

Scheme 1

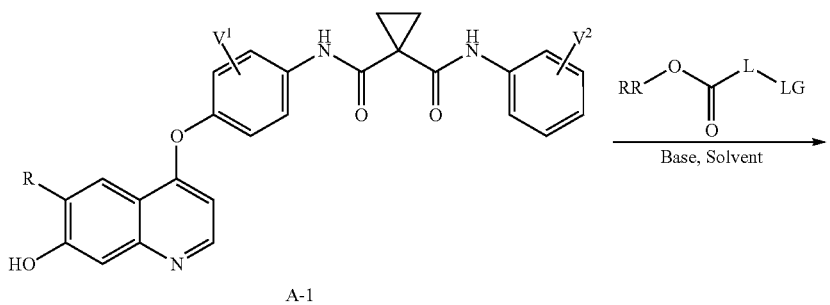

A-1

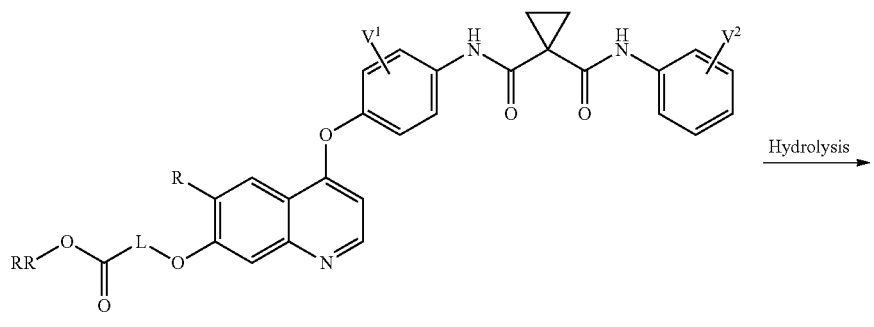

A-2

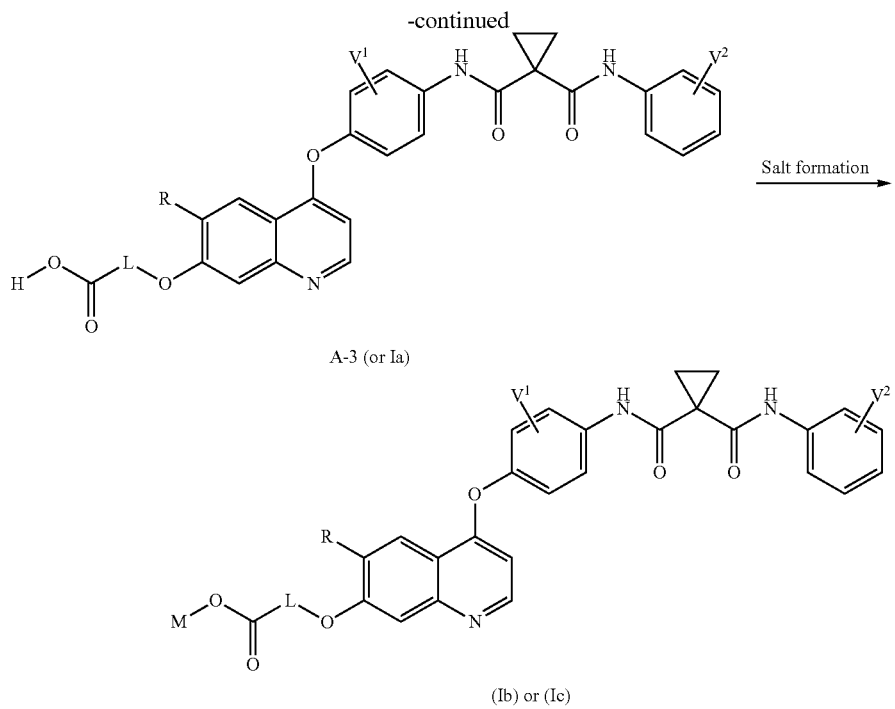

A-3 (or Ia)

(Ib) or (Ic)

in which Compound A-1 can be synthesized according to a method disclosed in WO2013/040801A1; and $V^1$, $V^2$, R, L and M are as defined in the quinolyl-substituted carboxylic acid compound or the pharmaceutically acceptable salt thereof as mentioned above.

For example, $V^1$ and $V^2$ are each independently selected from hydrogen, deuterium, halogen, $C_{1-6}$ alkyl and $C_{1-6}$ alkoxy;

R is hydrogen, $C_{1-12}$ alkyl, or $C_{1-12}$ alkoxy, and hydrogen of R is selectively substituted by $G^1$;

L is $C_{1-12}$ alkylene, and hydrogen of L is selectively substituted by $G^2$;

M is selected from:

(a) hydrogen, deuterium, $C_{2-12}$ alkyl, $C_{3-12}$ cycloalkyl, $C_{6-12}$ aryl, $C_{5-12}$ heteroaryl, and $C_{3-12}$ heteroalicyclic group, wherein hydrogen of M is selectively substituted by $G^3$; or (b) monovalent, divalent, trivalent, and tetravalent metal ions, preferably monovalent and divalent metal ions, and more preferably lithium ion, sodium ion, potassium ion, rubidium ion, cesium ion, magnesium ion, calcium ion, strontium ion, and barium ion, so as to give Compound Ib; or (c) ammonium ion and an organic amine being protonated, so as to give Compound Ic; the organic amine comprising, but not limited to, aliphatic amines substituted with $C_{1-12}$ alkyl, $C_{3-12}$ cycloalkyl, or $C_{3-12}$ heteroalicyclic group, the aliphatic amines being selectively substituted with one or more halogens or hydroxyls;

RR is hydrogen, $C_{1-12}$ alkyl, $C_{3-12}$ cycloalkyl, $C_{6-12}$ aryl, $C_{5-12}$ heteroaryl or $C_{3-12}$ heteroalicyclic group, and hydrogen of RR is selectively substituted by $G^4$;

LG is a common leaving group in organic chemistry, e.g. F, Cl, Br, I, $CH_3SO_3$, $CH_3CH_2SO_3$, $CH_3(CH_2)_2SO_3$, $(CH_3)_2CHSO_3$, tert-$BuSO_3$, $PhSO_3$, o-$CH_3PhSO_3$, m-$CH_3PhSO_3$, p-$CH_3PhSO_3$, o-$O_2NPhSO_3$, m-$O_2NPhSO_3$, p-$O_2NPhSO_3$, or $CF_3SO_3$; and wherein $G^1$, $G^2$, $G^3$, and $G^4$ are each independently selected from hydrogen, deuterium, —CN, —$CF_3$, —$CO_2H$, halogen, $C_{1-12}$ alkyl, $C_{3-12}$ cycloalkyl, $C_{2-12}$ alkenyl, $C_{2-12}$ alkynyl, $C_{6-12}$ aryl, $C_{5-12}$ heteroaryl, $C_{3-12}$ heteroalicyclic group, $R^1O$—, $R^1R^2N$—, $R^1S(=O)_m$—, $R^1R^2NS(=O)_m$—, $R^3C(=O)$—, $R^1R^2NC(=O)$—, $R^1OC(=O)$—, $R^3C(=O)O$—, $R^1R^2NC(=O)O$—, $R^3C(=O)NR^1$—, $R^1R^2NC(=O)NR^4$—, $R^1OC(=O)NR^4$—, $R^1S(=O)_mNR^4$—, $R^1R^2NS(=O)_mNR^4$—, $R^1R^2NC(=NR^5)NR^4$—, $R^1R^2NC(=CHNO_2)NR^4$—, $R^1R^2NC(=N-CN)NR^4$—, $R^1R^2NC(=NR^5)$—, $R^1S(=O)(=NR^5)NR^4$—, and $R^1R^2NS(=O)(=NR^5)$—;

$R^1$, $R^2$, $R^3$, $R^4$ and $R^5$ are each independently selected from hydrogen, deuterium, $C_{1-12}$ alkyl, $C_{2-12}$ alkenyl, $C_{2-12}$ alkynyl, $C_{3-12}$ cycloalkyl, $C_{6-12}$ aryl, $C_{5-12}$ heteroaryl, and $C_{3-12}$ heteroalicyclic group; $R^1$ and $R^2$, when being bonded to a same nitrogen atom, form a $C_{3-12}$ heteroalicyclic ring together with the nitrogen atom, wherein the $C_{3-12}$ heteroalicyclic ring selectively contains a hetero atom of O, N, and $S(=O)_m$; and hydrogen of $R^1$, $R^2$, $R^3$, $R^4$ and $R^5$ is selectively substituted by halogen, CN, $C_{1-12}$ alkyl or $C_{3-12}$ cycloalkyl; and m is from 0 to 2

"Base", "solvent", "hydrolysis" and "salt formation" are defined in "Definition of Terms" section, which does not constitute a limitation on the scope of protection of the preparation process.

The present application also relates to a pharmaceutical composition containing the quinolyl-substituted carboxylic acid compound or the pharmaceutically acceptable salt thereof.

The above pharmaceutical composition further comprises, in addition to the quinolyl-substituted carboxylic acid compound or the pharmaceutically acceptable salt thereof, one or more pharmaceutically acceptable carriers or diluents.

The pharmaceutical composition described above can be in a formulation of an oral preparation, an injection, an anal plug, a nasal inhalant, an eye drop or a skin patch.

A use of the quinolyl-substituted carboxylic acid compound as shown in Formula (I) or the pharmaceutically acceptable salt thereof, or the pharmaceutical composition containing the compound is to treat a disease caused by abnormality of a protein kinase. The kinase can be AXL or/and VEGFR2. The disease is a tumor, including solid tumors and liquid tumors.

The tumor mentioned in the use of the compound or/and the pharmaceutical composition containing the compound according to the present application specifically includes: lung cancer, bone cancer, pancreatic cancer, skin cancer, head and neck cancer, cutaneous or intraocular melanoma, uterine cancer, ovarian cancer, rectal cancer, anal cancer, gastric cancer, colon cancer, breast cancer, fallopian tube cancer, endometrial cancer, cervical cancer, vaginal cancer, vulva cancer, Hodgkin's disease, esophageal cancer, small intestine cancer, endocrine system cancer, thyroid cancer, parathyroid carcinoma, soft tissue sarcoma, urethral carcinoma, penile cancer, prostate cancer, chronic or acute leukemia, bladder cancer, renal or ureteral cancer, kidney cancer, central nervous system (CNS) neoplasm, spinal axis tumor, pituitary adenoma, gastrointestinal stromal tumor, colorectal carcinoma, non-small cell lung cancer, small cell lung cancer, mastocytosis, glioma, lymphoma and combinations thereof.

A medicine for treating a disease caused by abnormality of a protein kinase includes any one or more of the above compounds or a pharmaceutically acceptable salt, solvate, or prodrug thereof; or a racemate or enantiomer of any one or more of the above compounds, or a pharmaceutically acceptable salt, solvate or prodrug of the racemate or the enantiomer.

The medicine according to the present application further includes one or more pharmaceutically acceptable carriers and/or diluents, in addition to the quinolyl-substituted carboxylic acid compound or the pharmaceutically acceptable salt thereof.

The medicine according to the present application is provided in any one of the following forms:
(1) an oral preparation; (2) an injection; (3) an anal plug; (4) a nasal inhalant; (5) an eye drop; or (6) a skin patch.

Through a series of tests, it has been proven that the quinolyl-substituted carboxylic acid compound or the pharmaceutically acceptable salt thereof according to the present application brings the following beneficial effects: (1) it has been found through tests of inhibiting kinase activity that the compound according to the present application has a strong inhibitory effect on AXL and VEGFR2 kinases; (2) it has been found through tumor inhibition tests in animals that the quinolyl-substituted carboxylic acid compound or the pharmaceutically acceptable salt thereof can significantly inhibit tumors without obvious toxicity; (3) the compounds according to the present application can be used in combination with other antitumor medicines to achieve a synergistic or additive effect; and (4) the compounds according to the present application can be used in combination with other tumor therapies such as radiation therapy, interventional therapy, and the like. Therefore, it can be seen that the quinolyl-substituted carboxylic acid compound or the pharmaceutically acceptable salt thereof according to the present application can be used as an effective medicine in treating a disease caused by abnormality of a protein kinase.

Among the diseases caused by abnormal protein kinase activity and treated by the compound according to the present application, the kidney cancer is adrenal carcinoma, renal cell carcinoma, or renal pelvic carcinoma; and the glioma is brain stem glioma, neuroendocrine glioma, or neuroglioma.

In addition to tumors, the diseases caused by abnormal protein kinase activity and treated by the compound according to the present application also can be psoriasis, cirrhosis, diabetes, diseases involving angiogenesis, diseases involving restenosis, eye diseases such as AMD, rheumatoid arthritis and other inflammations, diseases of the immune system such as autoimmune diseases (for example, AIDS, etc.), cardiovascular diseases such as atherosclerosis, kidney disease, epilepsy, neurodegenerative diseases such as Alzheimer's disease, Huntington's disease, Parkinson's disease, etc.

The pharmaceutical composition containing the compound according to the present application is applied to treatment in a disease caused by abnormality of a protein kinase in mammals, such as a human patient.

The compound according to the present application (including a racemate, an enantiomer and other stereoisomers), or its pharmaceutically acceptable salt, hydrate, solvate or prodrug is prepared together with a suitable pharmaceutically acceptable carrier and a commonly used adjuvant in pharmacy through a formulation process, so as to form an administration-suitable pharmaceutical composition.

The medicine containing the compound according to present application can be administered in the following routes: (1) oral administration: for example, tablet, capsule, etc.; (2) injection: for example, intravenous injection, subcutaneous injection, intramuscular injection administration, eyeball injection, intraperitoneal injection, etc.; (3) anal plug administration: for example, suppository, gel, etc.; (4) nasal inhalation administration: for example, spray, aerosol, etc.; (5) eye drop administration; and (6) skin patch administration. A medicine release system can also be used, for example, liposome, sustained release technique, controlled release technique, and the like, where oral administration and injection are preferable, and oral administration is more preferable.

The methods commonly used in the pharmaceutical industry can be adopted to produce the various formulations of the pharmaceutical composition containing the compound according to the present application, for example, mixing, dissolving, granulating, grinding, emulsifying, capsulating, sugar coating, freeze drying, freeze spray, and the like.

The compound according to the present application is contained in the aforementioned pharmaceutical composition in an amount ranging from 0.001% to 100%. The pharmaceutical composition is administered to mammals including human with an effective dosage of 0.1 to 500 mg per kilogram of body weight per day, and optimally 1 to 100 mg per kilogram of body weight per day. Within such effective dosage range, the compound of the present application can exert its pharmacological effects on inhibiting protein kinase activity and treating diseases (e.g., cancer) caused by abnormality of a protein kinase.

The medicine according to the present application is administered in a frequency that varies depending on the compound or the pharmaceutical composition thereof used and the disease to be treated. The pharmaceutical composition according to the present application is usually administered 1-6 times per day, and optimally 1-3 times per day.

The packaging and preservation of the medicine according to the present application are the same as the traditional chemical drugs. For example, the medicine in a solid formulation is directly loaded into a glass, plastic, paper or metal bottle, and a desiccant or the like is preferably placed in the bottle to maintain the medicine quality; the medicine in a liquid formulation is typically placed in a glass, plastic or metal bottle or hose; and the medicine in an aerosol formulation is typically placed in a pressure-resistant metal or plastic container with means such as a pressure reducing valve.

Definition of Terms

The following is a definition of terms involved in the present application. The variable groups used in the present application, such as $R^a$, $R^b$, g, etc., are only applicable to this subsection (i.e., "Definition of Terms").

According to common knowledge of those skilled in the art, chemical reactions are often carried out in a solvent. The solvent commonly used in the preparation of the compound according to the present application includes, but is not limited to, water, methanol, ethanol, isopropanol, n-propanol, n-butanol, isobutanol, tert-butanol, 2-methoxyethanol, 2,2,2-trifluoroethanol, dichloromethane, 1,2-dichloroethane, chloroform, THF, dioxane, DME, ethyl acetate, diethyl ether, methyl tert-butyl ether, hexane, cyclohexane, toluene, acetonitrile, DMF, DMSO, and combinations of two or more of these solvents.

In some steps of the preparation of the compound according to the present application, the reactions are carried out in presence of base. The base includes, but is not limited to, organic bases, such as $MeNH_2$, $Me_2NH$, $Me_3N$, $EtNH_2$, $Et_2NH$, $Et_3N$, $n\text{-}PrNH_2$, $n\text{-}Pr_2NH$, $n\text{-}Pr_3N$, $i\text{-}PrNH_2$, $i\text{-}Pr_2NH$, $i\text{-}Pr_3N$, $n\text{-}BuNH_2$, $n\text{-}Bu_2NH$, $n\text{-}Bu_3N$, $s\text{-}BuNH_2$, $s\text{-}Bu_2NH$, $s\text{-}Bu_3N$, $i\text{-}BuNH_2$, $i\text{-}Bu_2NH$, $i\text{-}Bu_3N$, $t\text{-}BuNH_2$, $t\text{-}Bu_2NH$, $t\text{-}Bu_3N$, $i\text{-}Pr_2NEt$, 2-amino-2-(hydroxymethyl)propane-1,3-diol, cyclopropylamine, dicyclopropylamine, cyclobutylamine, dicyclobutylamine, cyclopentylamine, dicyclopentylamine, cyclohexylamine, dicyclohexylamine, pyridine, DBU, DABCO, tetramethylguanidine, pentamethylguanidine, tetraethylguanidine, pentaethylguanidine, morpholine, 1-methylmorpholine, piperidine, 1-methylpiperidine, 1-ethylpiperidine, piperazine, 1-methylpiperazine, 1-ethylpiperazine, 1,4-dimethylpiperazine, 1,4-diethylpiperazine, pyrrolidine, 1-methylpyrrolidine, 1-ethylpyrrolidine, MeONa, MeOK, MeOLi, EtOLi, EtONa, EtOK, n-PrOLi, n-PrONa, n-PrOK, i-PrOLi, i-PrONa, i-PrOK, n-BuOLi, n-BuONa, n-BuOK, i-BuOLi, i-BuONa, i-BuOK, s-BuOLi, s-BuONa, s-BuOK, t-BuOLi, t-BuONa, t-BuOK, n-BuLi, s-BuLi, t-BuLi, $NaN(SiMe_3)_2$, $LiN(SiMe_3)_2$, $KN(SiMe_3)_2$, etc. The base also includes, but is not limited to, inorganic bases such as ammonia gas, ammonia water, LiOH, NaOH, KOH, RbOH, CsOH, $Cs_2OH$, $Cs_2CO_3$, $Rb_2CO_3$, $Li_2CO_3$, $Na_2CO_3$, $K_2CO_3$, $NaHCO_3$, LiF, NaF, KF, RbF, CsF, $K_3PO_4$, $K_2HPO_4$, $KH_2PO_4$, $Na_3PO_3$, $Na_2HPO_4$, $NaH_2PO_4$, $Li_3PO_3$, $Li_2HPO_4$, $LiH_2PO_4$, NaH, LiH, KH, RbH, CsH, CaO, $Ca(OH)_2$, $Ca_2CO_3$, MgO, $Mg(OH)_2$, $Mg_2CO_3$, etc., and combinations of two or more of the above bases.

In the preparation of the compound according to the present application, some steps require a hydrolysis reaction, which is generally carried out in the presence of a base or an acid. The base is defined as above. The acid includes, but is not limited to, $HCO_2H$, AcOH, TFA (trifluoroacetic acid), HCl (hydrochloric acid), $H_2SO_4$, $HNO_3$, $H_3PO_4$, p-TsOH, $PhSO_3H$, CSA, MsOH, etc., Lewis acids such as $ZnCl_2$, $AlCl_3$, $BF_3 \cdot OEt_2$, and combinations thereof.

In the preparation of the compound according to the present application, some steps require a salt formation reaction, which is a reaction between the carboxylic acid compound A-3 and the above-mentioned base for framing a carboxylate compound Ib or Ic.

The reactions for preparing the compound according to the present application are usually carried out at room temperature, but sometimes the temperature should be lowered to −78° C. or elevated to 200° C. The reactions are usually carried out under the aforementioned solvent and temperature and conventional stirring conditions, but sometimes in a microwave oven. When the adopted base, reagent, or catalyst is sensitive to water or oxygen, the reactions are carried out under an anhydrous and anaerobic condition. In this case, a protic solvent cannot be used.

"Solvate" means a stable substance formed by the compound according to the present application and a common chemical solvent through a covalent bond, a hydrogen bond, an ionic bond, a Van der Waals' force, complexation, inclusion, or the like. The solvent can be methanol, ethanol, propanol, butanol, ethylene glycol, propylene glycol, polyethylene glycol, acetone, acetonitrile, diethyl ether, methyl tert-butyl ether, or the like.

"Hydrate" indicates a solvate in which the solvent is water.

"Prodrug" refers to a converted compound from the compound according to the present application through chemical synthesis or physical manners, where the converted compound, after being administrated to a mammal, is re-converted to the compound according to the present application in the mamma. The "prodrug" method is generally used to overcome the poor or deficient physicochemical properties or medicine-forming properties of the pharmaceutical compound itself.

"Racemate, enantiomer, cis-trans isomer, and other stereoisomers" mean compounds having identical molecular formula or molecular weight, but different in the bonding modes and spatial arrangement between the atoms, also known as isomers or stereoisomers. When these stereoisomers are mirrored with respect to each other, i.e., they look alike, but fails to completely coincide as the left and right hands, these compounds are called enantiomers. The absolute configurations of the enantiomers are usually indicated by (R)- and (S)-, or R- and S-. The specifical rules for determining the absolute configurations of the enantiomers are found in Chapter 4 of "Advanced Organic Chemistry," $4^{th}$ edition (by J. March, John Wiley and Sons, New York, 1992). The (R)- and (S)-enantiomers have opposite rotational effects on polarized light, namely left-handed and right-handed. When the (R)- and (S)-enantiomers are mixed or present in a ratio of 1:1, the mixture has no rotational effect on the polarized light, and the mixture is referred to as a racemate.

The compound according to the present application may also have tautomers, rotamers, cis-trans isomers, and the like, where these concepts can be found in and comprehend with the aids of J. March, "Advanced Organic Chemistry", $4^{th}$ edition. These isomers are also encompassed by the present application as long as they have the identical or similar effects of inhibiting AXL and/or VEGFR2 activity as the compounds according to the present application.

According to the common knowledge in the related art, the compound according to the present application, after being administrated to a mammal (such as a human), is possible to be metabolized to various metabolites by different enzymes in the animal. Provided these metabolites have the similar effects of inhibiting AXL and/or VEGFR2 activity as the compounds according to the present application, these metabolites are also encompassed by the present application.

"Pharmaceutical composition" refers to a preparation produced by mixing one or more compounds according to the present application, its or their pharmaceutically acceptable salt, solvate, hydrate, or prodrug, and other chemical ingredients (e.g., pharmaceutically acceptable carrier or diluent). The purpose of the pharmaceutical composition is to facilitate the administration of the compound to the animal. The above pharmaceutical composition may include, in addition to the pharmaceutically acceptable carrier, an adjuvant commonly used in pharmacy or pharmaceutical science, such as an antibacterial agent, an antifungal agent, an antimicrobial agent, a quality-maintaining agent, a toner, a solubilizer, a thickener, a surfactant, a complexing agent, a protein, an amino acid, fat, sugar, vitamin, mineral, a trace element, a sweetener, a pigment, a flavor or any combination thereof.

"Pharmaceutically acceptable carrier" or "diluent" refers to an inactive ingredient in the pharmaceutical composition, which can be, but is not limited to, calcium carbonate, calcium phosphate, various sugars (e.g., lactose, mannitol, etc.), starch, cyclodextrin, magnesium stearate, cellulose, magnesium carbonate, acrylic acid polymer, methacrylic acid polymer, gel, water, polyethylene glycol, propylene glycol, ethylene glycol, castor oil, hydrogenated castor oil, polyethoxylated hydrogenated castor oil, sesame oil, corn oil, peanut oil, and the like.

"Alkyl" means a straight or branched chain saturated hydrocarbon group having a specified number of carbon atoms. For example, $C_{1-12}$ alkyl means a straight or branched chain group containing at least 1 and up to 12 carbon atoms. The $C_0$ alkyl group represents a covalent single bond. The alkyl group in the present application includes, but is not limited to, methyl, ethyl, propyl, butyl, isopropyl, neopentyl, 2-methyl-1-hexyl, etc. The alkyl group described in the present application is also referred to as an "alkylene group" in some cases, which represents a group of the alkyl group losing one hydrogen atom. One or all of the hydrogen atoms in the alkyl or alkylene group can be substituted by the following groups: cycloalkyl, aryl, heteroaryl, a heteroalicyclic ring group, halogen, amino, hydroxyl, cyano, nitro, carboxyl, sulfhydryl, oxo, alkoxy, aryloxy, alkyl sulfhydryl, aryl sulfhydryl, carbonyl, thiocarbonyl, C-amido, A-amido, O-aminocarbonyloxy, N-aminocarbonyloxy, N-thioaminocarbonyloxy, N-thioaminocarbonyloxy, C-ester group, O-ester group, and —NR$^a$R$^b$, wherein R$^a$ and R$^b$ are respectively selected from hydrogen, alkyl, cycloalkyl, aryl, acetyl, carbonyl, sulfonyl, trifluoromethanesulfonyl, etc., and R$^a$ and R$^b$ together with a nitrogen atom form a five- or six-membered heteroalicyclic ring.

"Cycloalkyl" or "cycloalkane" refers to a monocyclic, dicyclic or polycyclic hydrocarbon group having a specified number of carbon atoms. In the case of a dicyclic or polycyclic hydrocarbon group, the rings can be fused (i.e., two or more rings share two adjacent carbon atoms) or connected together to form a spirane (i.e., two or more rings share one carbon atom). For example, $C_{1-12}$ cycloalkyl refers to a monocyclic, dicyclic or polycyclic hydrocarbon group having at least 1 and up to 12 carbon atoms. $C_0$ cycloalkyl represents a covalent single bond. The cycloalkyl group may contain an unsaturated double or triple bond, but does not have a fully conjugated π electron system. The cycloalkyl group described in the present application also refers to a cycloalkylene group in some cases, i.e., a cycloalkyl group losing one hydrogen atom. The cycloalkyl group according to the present application includes, but is not limited to, cyclopropyl, cyclobutyl, cyclohexyl, cyclopentenyl, cycloheptatrienyl, adamantane, etc. (examples are shown in Table A):

TABLE A

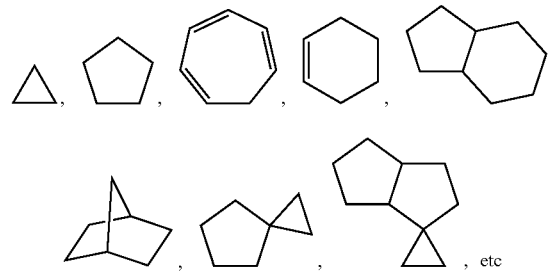

One or all of the hydrogen atoms in the cycloalkyl group or cycloalkane can be substituted by the following groups: alkyl, aryl, heteroaryl, a heteroalicyclic ring, halogen, amino, hydroxyl, cyano, nitro, carboxyl, sulfhydryl, oxo, alkoxy, aryloxy, alkyl sulfhydryl, aryl sulfhydryl, carbonyl, thiocarbonyl, C-amido, TV-amido, O-aminocarbonyloxy, N-aminocarbonyloxy, O-thioaminocarbonyloxy, N-thioaminocarbonyloxy, C-ester group, O-ester group, and —NR$^a$R$^b$, wherein R$^a$ and R$^b$ are respectively selected from hydrogen, alkyl, cycloalkyl, aryl, acetyl, carbonyl, sulfonyl, trifluoromethanesulfonyl, etc., and R$^a$ and R$^b$ together with a nitrogen atom form a five- or six-membered heteroalicyclic ring.

"Heteroalicyclic group" or "heteroalicyclic ring" refers to a monocyclic, bicyclic or polycyclic ring system consisting of 3 to 12 non-hydrogen ring atoms, in which at least one of the ring atoms is a hetero atom selected from O, N, S and P, the remaining ring atoms are carbon atoms. For example, a $C_8$ heteroalicyclic group refers to a monocyclic, bicyclic or polycyclic group consisting of 8 non-hydrogen ring atoms, in which at least one ring atom is selected from O, N, S and P. Such a ring may contain, in addition to single bonds, a double or triple bond, which does not constitute a fully conjugated aromatic structure. The monocyclic, bicyclic or polycyclic system may exist in the form of fused ring, bridged ring or spiro ring. The heteroalicyclic group according to the present application also refers to a subheteroalicyclic group in some cases, i.e., a heteroalicyclic group losing one hydrogen atom. The heteroalicyclic group or heteroalicyclic ring described in the present application includes, but is not limited to, piperidine, morpholine, piperazine, pyrrolidine, indoline, tetrahydropyridine, tetrahydrofuran, tropine, etc. (examples are shown in Table B):

TABLE B

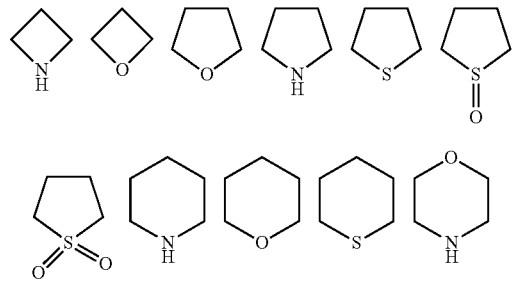

TABLE B-continued

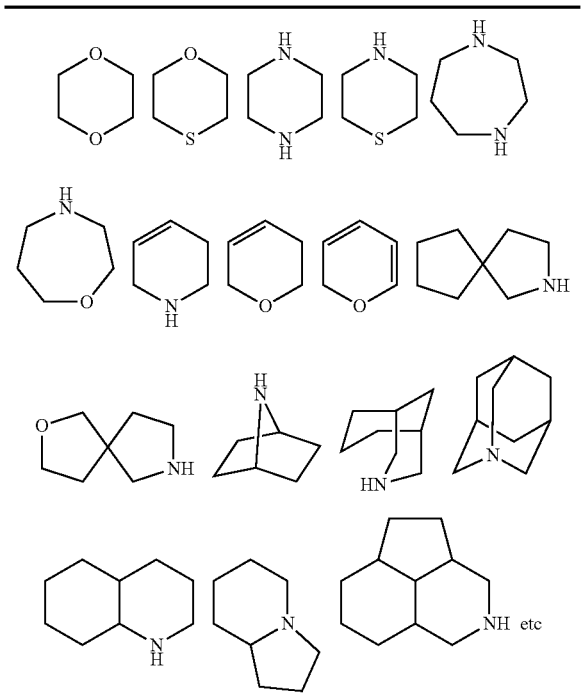

One or all of the hydrogen atoms in the heteroalicyclic group or heteroalicyclic ring can be substituted by the following groups: alkyl, cycloalkyl, aryl, heteroaryl, a heteroalicyclic ring, halogen, amino, hydroxyl, cyano, nitro, carboxyl, sulfhydryl, oxo, alkoxy, aryloxy, alkyl sulfhydryl, aryl sulfhydryl, carbonyl, thiocarbonyl, C-amido, N-amido, O-aminocarbonyloxy, N-aminocarbonyloxy, O-thioaminocarbonyloxy, N-thioaminocarbonyloxy, C-ester group, O-ester group, and —$NR^aR^b$, wherein $R^a$ and $R^b$ are respectively selected from hydrogen, alkyl, cycloalkyl, aryl, acetyl, carbonyl, sulfonyl, trifluoromethanesulfonyl, etc., and $R^a$ and $R^b$ together with a nitrogen atom form a five- or six-membered heteroalicyclic ring.

"Alkenyl" means a straight or branched chain hydrocarbon group having at least two carbon atoms and at least one double bond. For example, $C_{2-12}$ alkenyl indicates a straight or branched chain unsaturated group having least 2 and up to 12 carbon atoms as well as at least one double bond. The alkenyl group described in the present application includes, but is not limited to, vinyl, 2-propenyl, 1-pentenyl, etc.

"Alkynyl" means a straight or branched chain hydrocarbon group having at least two carbon atoms and at least one triple bond. For example, $C_{2-12}$ alkynyl indicates a straight or branched chain unsaturated group having least 2 and up to 12 carbon atoms as well as at least one triple bond. The alkynyl group described in the present application includes, but is not limited to, vinyl, 2-propenyl, 1-pentenyl, etc.

"Halogen" means fluorine, chlorine, bromine or iodine.

"Alkoxy" refers to an alkyl group having a specified number of carbon atoms and an oxygen atom through which the alkyl group is to be bonded to another group. The alkoxy group described in the present application includes, but is not limited to, methoxy, ethoxy, propoxy, butoxy, cyclopentyloxy, cyclohexyloxy, isopropoxy, neopentyloxy, 2-methyl-1-hexyloxy, etc.

"Cycloalkoxy" refers to a cycloalkyl group having a specified number of carbon atoms and an oxygen atom through which the cycloalkyl group is to be bonded to another group. The cycloalkoxy group described in the present application includes, but is not limited to, cyclopropoxy, cyclobutoxy, cyclohexanoxy, and the like.

"Hetero epoxy group" refers to a heteroalicyclic group having an oxygen atom through which the heteroalicyclic group is to be bonded to another group. The heteroaliphatic oxo group described in the present application includes, but is not limited to, piperidin-4-yloxy, oxetan-3-yloxy, etc.

"Aryl" means a monocyclic, bicyclic or polycyclic group having a specified number of carbon atoms, in which at least one ring has a fully conjugated π electron system and conforms to the N+2 rule, i.e., the group has aromaticity, but the entire group does not have to be fully conjugated. For example, $C_6$ aryl refers to phenyl. The aryl group may also be present in the form of an arylene group, i.e., an aryl group has two or more bonding sites bonded to other groups. The aryl group described in the present application includes, but is not limited to, phenyl, naphthyl, indenyl, dihydroindenyl, tetrahydronaphthyl, etc. One or all of the hydrogen atoms in the aryl group can be substituted by the following groups: alkyl, cycloalkyl, heteroaryl, heteroalicyclic group, halogen, amino, hydroxyl, cyano, nitro, carboxyl, sulfhydryl, oxo, alkoxy, aryloxy, alkyl sulfhydryl, aryl sulfhydryl, carbonyl, thiocarbonyl, C-amido, N-amido, O-aminocarbonyloxy, N-aminocarbonyloxy, O-thioaminocarbonyloxy, N-thioaminocarbonyloxy, C-ester group, O-ester group, and —$NR^aR^b$, wherein $R^a$ and $R^b$ are respectively selected from hydrogen, alkyl, cycloalkyl, aryl, acetyl, carbonyl, sulfonyl, trifluoromethanesulfonyl, etc., and $R^a$ and $R^b$ together with a nitrogen atom form a five- or six-membered heteroalicyclic ring.

"Heteroaryl" means a monocyclic, bicyclic or polycyclic group having a specified number of non-hydrogen ring atoms, in which at least one ring atom is a hetero atom selected from O, N, S and P, and the remaining ring atoms are carbon atoms, and in which at least one ring has a fully conjugated n electron system and conforms to the N+2 rule, i.e., the group has aromaticity, but the entire group does not have to be fully conjugated. For example, $C_5$ heteroaryl indicates an aromatic ring group consisting of 5 non-hydrogen ring atoms, in which at least one ring atom is a hetero atom selected from O, N, S and P. The heteroaryl group may also be present in the form of a heteroarylene group, i.e., a heteroaryl group has two or more bonding sites bonded to other groups. The heteroaryl group described in the present application includes, but is not limited to, pyridine, pyridinone, tetrahydropyridinone, pyrimidine, pyrazine, pyridazine, imidazole, thiazole, thiophene, furan, indole, azaindole, benzimidazole, indoline, indolone, quinoline, etc. (examples are shown in Table C):

TABLE C

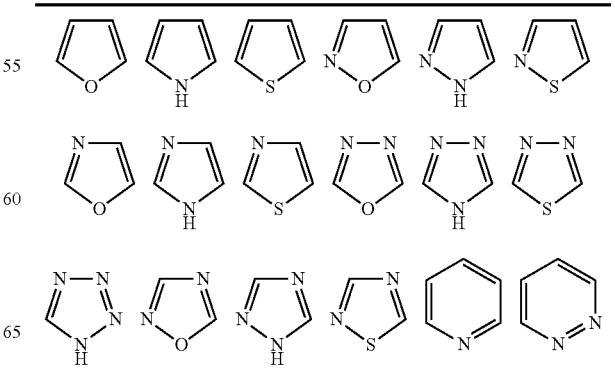

TABLE C-continued

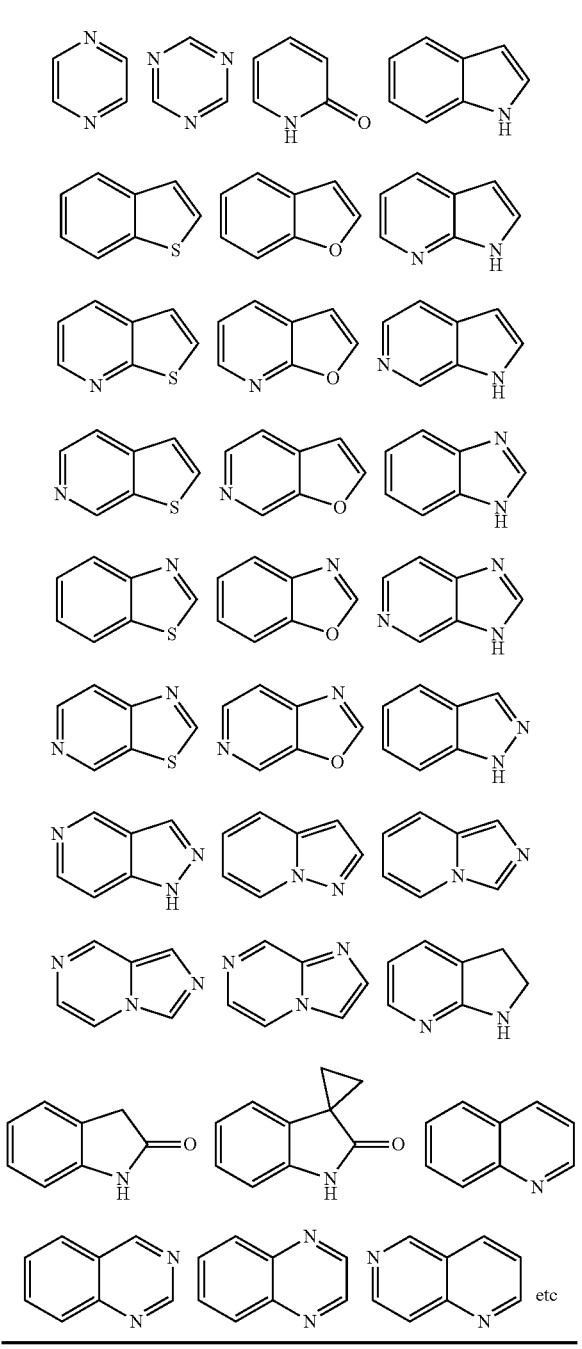

One or all of the hydrogen atoms in the heteroaryl group can be substituted by the following groups: alkyl, cycloalkyl, aryl, heteroaryl, a heteroalicyclic group, halogen, amino, hydroxyl, cyano, nitro, carboxyl, sulfhydryl, oxo, alkoxy, aryloxy, alkyl sulfhydryl, aryl sulfhydryl, carbonyl, thiocarbonyl, C-amido, N-amido, O-aminocarbonyloxy, N-aminocarbonyloxy, O-thioaminocarbonyloxy, N-thioaminocarbonyloxy, C-ester group, O-ester group, and —NR$^a$R$^b$, wherein R$^a$ and R$^b$ are respectively selected from hydrogen, alkyl, cycloalkyl, aryl, acetyl, carbonyl, sulfonyl, trifluoromethanesulfonyl, etc., and R$^a$ and R$^b$ together with a nitrogen atom form a five- or six-membered heteroalicyclic ring.

"Nitrogen atom-containing heteroaryl" refers to a heteroaryl group containing at least one nitrogen atom. The nitrogen atom-containing heteroaryl group described in the present application includes, but is not limited to, pyridyl, quinolyl, pyrazinyl, pyridazinyl, etc.

"Aryloxy" refers to an aryl group having an oxygen atom through which the aryl group is to be bonded to another group. The aryloxy group described in the present application includes, but is not limited to, phenoxy, naphthyloxy, etc.

"Heteroaryloxy" refers to a heteroaryl group having an oxygen atom through which the heteroaryl group is to be bonded to another group. The heteroaryloxy group described in the present application includes, but is not limited to, 4-pyridyloxy, 2-thienyloxy, etc.

"N-oxide" refers to a molecule in which the N atom and the O atom are connected by a double bond to form an N=O or N$^+$—O$^-$ structure.

"Amino" refers to H$_2$N—, R$^a$HN—, or R$^a$R$^b$N—, where hydrogen in H$_2$N— is substituted to form the R$^a$HN— or R$^a$R$^b$N—.

"oxo" refers to =O or —O—, i.e., an oxygen atom is bonded to a carbon or a hetero atom such as N, S, P, etc. via a double bond or a single bond. Examples of compounds substituted with an oxo group include, but are not limited to, those shown in Table D:

TABLE D

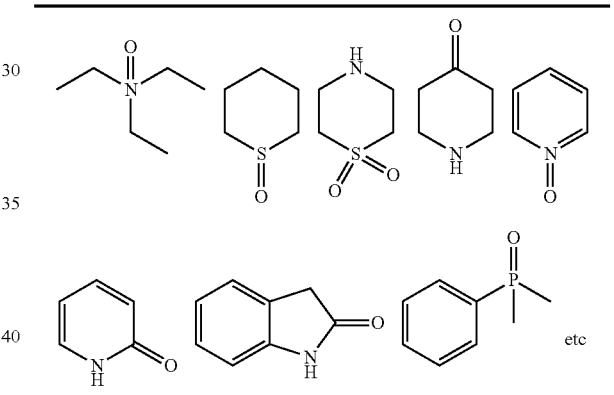

"hydroxy" refers to —OH.
"nitro" refers to —NO$_2$.
"carboxyl" refers to —CO$_2$H.
"sulfhydryl" refers to —SH.
"alkyl sulfhydryl" refers to alkyl-S—.
"aryl sulfhydryl" refers to aryl-S—.
"carbonyl" refers to —C(=O)—.
"thiocarbonyl" refers to —C(=S)—.
"C-amido" refers to —C(=O)NR$^a$R$^b$.
"N-amido" refers to C(=O)NR$^a$—.
"O-aminocarbonyloxy" refers to —O—C(=O)NR$^a$R$^b$.
"N-Aminocarbonyloxy" refers to O—C(=O)NR$^a$—.
"O-thioaminocarbonyloxy" refers to —O—C(=S)NR$^a$R$^b$.
"N-thioaminocarbonyloxy" refers to O—C(=S)NR$^a$—.
"C-ester group" refers to —C(=O)OR$^a$.
"N-ester group" refers to C(=O)O—.
"acetyl" refers to CH$_3$C(=O)—.
"sulfonyl" refers to —SO$_2$R$^a$.
"trifluoromethanesulfonyl" refers to CF$_3$SO$_2$—.

DETAILED DESCRIPTION

The present application is described in detail below in combination with the specific examples, in order to facilitate the understanding of the compounds, the method for preparing the compounds, and the beneficial effects of the present application. However, the contents claimed in the present application are not limited to the specific examples.

The English abbreviations used in the examples and the corresponding meanings are listed below. If an abbreviation unlisted herein appears in the examples, it represents a generally accepted meaning.
HPLC: high performance liquid chromatography
g: gram
mg: milligram
mol: mole
mmol: millimole
nM: nanomole (concentration unit)
μM: micromole (concentration unit)
M: mole (concentration unit)
N: equivalent concentration
L: liter
μL: microliter
[M+H]$^+$: molecular ion peak in mass spectrometry
m/z: mass-to-charge ratio
δ: chemical shift
MeOH: methanol
EtOH: ethanol
DMSO-d$_6$: dimethyl sulfoxide-d$_6$
CDCl$_3$: deuterated chloroform
CD$_3$OD: deuterated methanol
TMS: tetramethylsilane
HCl: hydrogen chloride or hydrochloric acid
LiOH.H$_2$O: lithium hydroxide hydrate
Ca(OH)$_2$: calcium hydroxide
KOH: potassium hydroxide
NaOH: sodium hydroxide
DBU: 1,8-diazabicyclo[5.4.0]undec-7-ene
DABCO: 1,4-diazabicyclo[2.2.2]octane General Experimental Conditions:

Nuclear magnetic resonance hydrogen and carbon spectra were obtained on a Varian 300 or 400 MHz instrument or a Bruker 300 or 400 MHz instrument (using deuterated DMSO, deuterated chloroform, deuterated methanol, etc. as solvent, TMS as internal standard). Mass spectrum was obtained by liquid chromatography-mass spectrometry (using ESI or APCI ion source ZQ4000, Waters, USA). Ultraviolet spectrum was measured by a UV-3010 ultraviolet spectrophotometer (Hitachi, Japan). Infrared spectrum was obtained by using a NICOLET6700 infrared spectrometric analyzer (KBr pellet). High performance liquid chromatography was performed by using a Waters 2695 ZORBAX high performance liquid chromatograph (Bx-C8 5μ, 150×4.6 mm chromatographic column), unless otherwise specified. Melting point was measured by using an Electrothermal digital melting point meter IA9100 and was uncalibrated.

Starting materials, reagents and solvents were purchased from the following suppliers: Beta-Pharma; Shanghai PI Chemicals; AndaChem; Taiyuan; Shanghai FWD Chemicals; Sigma-Aldrich, Milwaukee, Wis., USA; Acros, Morris Plains, N.J., USA; Frontier Scientific, Logan, Utah, USA; Alfa Aesar, Ward Hill, Mass., USA, etc., or synthesized by methods reported in the literatures. Unless otherwise indicated, the solvent from the supplier's is generally used directly without drying or dried through molecular sieves.

Example 1

2-[[4-[2-fluoro-4-[[1-[(4-fluorophenyl)carbamoyl]cyclopropanecarbonyl]amino]phenoxy]-6-methoxy-7-quinolyl]oxy]acetic acid (I-2) is prepared according to the following reaction equation:

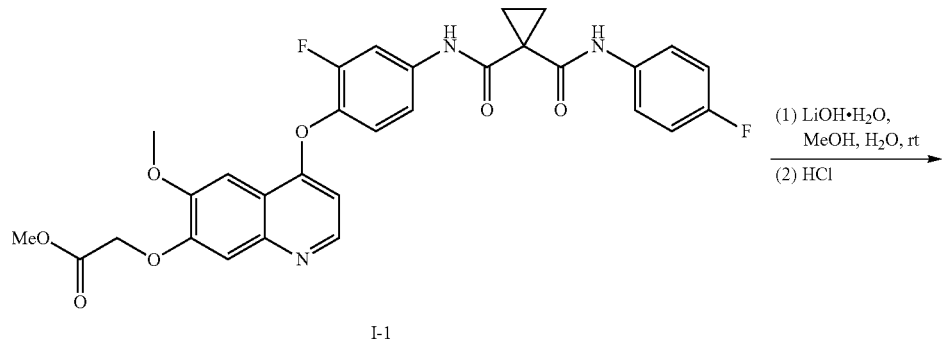

I-1

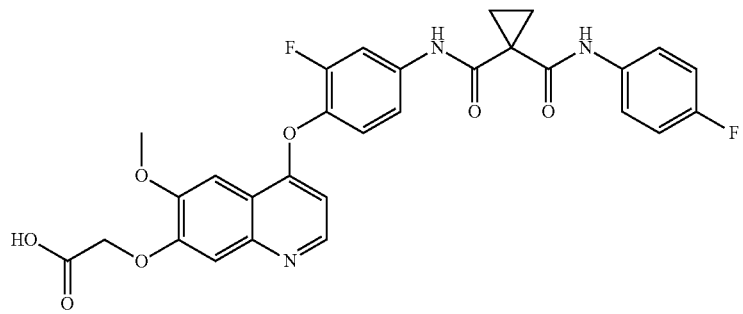

I-2

LiOH.H$_2$O (44 mg, 1.04 mmol) was added into a solution of methyl 2-[[4-[2-fluoro-4-[[1-[(4-fluorophenyl)aminocarbonyl]cyclopropanecarbonyl]amino]phenoxy]-6-methoxy-7-quinolyl]oxy]acetate (I-1, 60 mg, 0.104 mmol, prepared according to the method described in WO2013/040801A1) dissolved in methanol (1.0 mL) and water (0.3 mL). The obtained mixture was stirred at room temperature for 1 h, and the reaction solution was diluted with water and adjusted to pH 4 with HCl (1N). After filtration, the obtained solid product was collected and washed with acetonitrile, so as to obtain 2-[[4-[2-fluoro-4-[[1-[(4-fluorophenyl)carbamoyl]cyclopropanecarbonyl]amino]phenoxy]-6-methoxy-7-quinolyl]oxy]acetic acid (I-2) (26 mg, yield: 44%). Analysis data: $^1$H-NMR (400 MHz, DMSO-d$_6$): δ=13.29 (s, br, 1H), 10.44 (s, 1H), 10.00 (s, 1H), 8.63 (s, 1H), 7.94 (d, J=12.8 Hz, 1H), 7.66-7.46 (m, 5H), 7.37 (s, 1H), 7.18-7.14 (m, 2H), 6.66-6.62 (m, 1H), 4.97 (s, 2H), 4.02 (s, 3H), 1.49 (d, J=6.8 Hz, 4H). Mass spectrum (ESI) m/z: 564.1 [M+H]$^+$.

Example 2

Calcium 2-[[4-[2-fluoro-4-[[1-[(4-fluorophenyl)carbamoyl]cyclopropanecarbonyl]amino]phenoxy]-6-methoxy-7-quinolyl]oxy]acetate (1:1) (I-3) is prepared according to the following reaction equation:

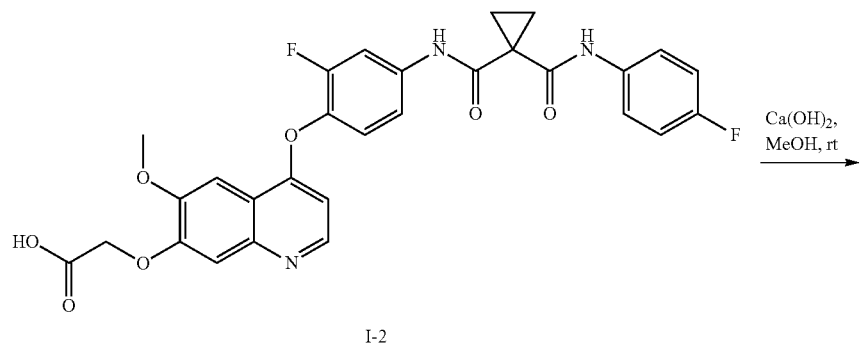

I-2

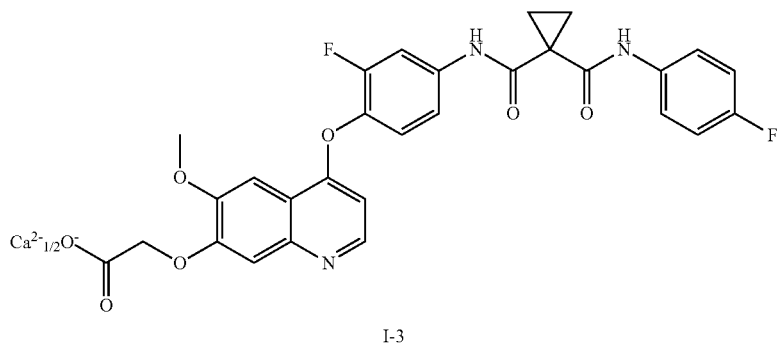

I-3

An aqueous solution of Ca(OH)$_2$ (0.031 N, 1 mL, 0.031 mmol) was added into a solution of 2-[[4-[2-fluoro-4-[[1-[(4-fluorophenyl)carbamoyl]cyclopropanecarbonyl]amino]phenoxy]-6-methoxy-7-quinolyl]oxy]acetic acid (I-2, 35 mg, 0.062 mmol) dissolved in methanol (0.5 mL). The mixture was stirred at room temperature for 16 h, diluted with water, and then freeze-dried to obtain calcium 2-[[4-[2-fluoro-4-[[1-[(4-fluorophenyl)carbamoyl]cyclopropanecarbonyl]amino]phenoxy]-6-methoxy-7-quinolyl]oxy]acetate (1:1) (I-3) (29 mg, yield: 80%). Analysis data: $^1$H-NMR (400 MHz, DMSO-d$_6$): δ=10.49 (s, 1H), 10.11 (s, 1H), 8.42 (d, J=4.5 Hz, 1H), 7.91-7.86 (m, 1H), 7.67-7.62 (m, 2H), 7.49-7.34 (m, 4H), 7.19-7.12 (m, 3H), 6.35 (d, J=5.1 Hz, 1H), 4.40 (s, 2H), 3.94 (s, 3H), 1.46 (s, 4H). Mass spectrum (ESI) m/z: 564.1 [M+H]$^+$.

Example 3

4-[[4-[2-fluoro-4-[[1-[(4-fluorophenyl)carbamoyl]cyclopropanecarbonyl]amino]phenoxy]-6-methoxy-7-quinolyl]oxy]butyric acid (II-2) is prepared according to the following reaction equation:

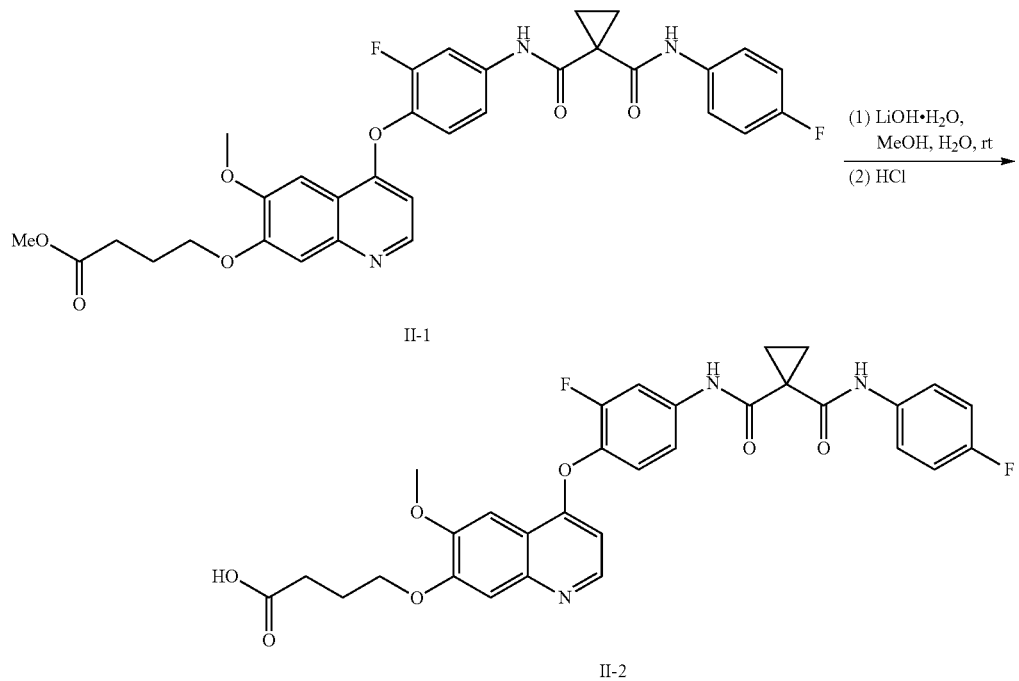

LiOH·H$_2$O (194 mg, 4.628 mmol) was added into a solution of methyl 4-[[4-[2-fluoro-4-[[1-[(4-fluorophenyl)carbamoyl]cyclopropanecarbonyl]amino]phenoxy]-6-methoxy-7-quinolyl]oxy]butyrate (II-1, 280 mg, 0.463 mmol, prepared according to the method described in WO2013/040801A1) dissolved in methanol (3.0 mL) and water (1.0 mL). The obtained mixture was stirred at room temperature for 1 h, and the reaction solution was diluted with water and adjusted to pH 4 with HCl (1N). After filtration, the obtained solid product was collected and washed with acetonitrile, so as to obtain 4-[[4-[2-fluoro-4-[[1-[(4-fluorophenyl)carbamoyl]cyclopropanecarbonyl]amino]phenoxy]-6-methoxy-7-quinolyl]oxy]butyric acid (II-2) (191.3 mg, yield: 70%). Analysis data: $^1$H-NMR (400 MHz, DMSO-d$_6$): δ=12.22 (s, 1H), 10.49 (s, 1H), 10.00 (s, 1H), 8.75 (d, J=6.0 Hz, 1H), 7.97 (d, J=12.8 Hz, 1H), 7.71 (s, 1H), 7.67-7.50 (m, 5H), 7.18-7.14 (m, 2H), 6.83 (d, J=6.4 Hz, 1H), 4.25 (t, J=6.4 Hz, 2H), 4.03 (s, 3H), 2.51-2.45 (m, 2H), 2.12-2.05 (m, 2H), 1.49 (d, J=9.6 Hz, 4H). Mass spectrum (ESI) m/z: 592.1 [M+H]$^+$.

Example 4

Sodium 4-[[4-[2-fluoro-4-[[1-[(4-fluorophenyl)carbamoyl]cyclopropanecarbonyl]amino]phenoxy]-6-methoxy-7-quinolyl]oxy]butyrate (II-3) is prepared according to the following reaction equation:

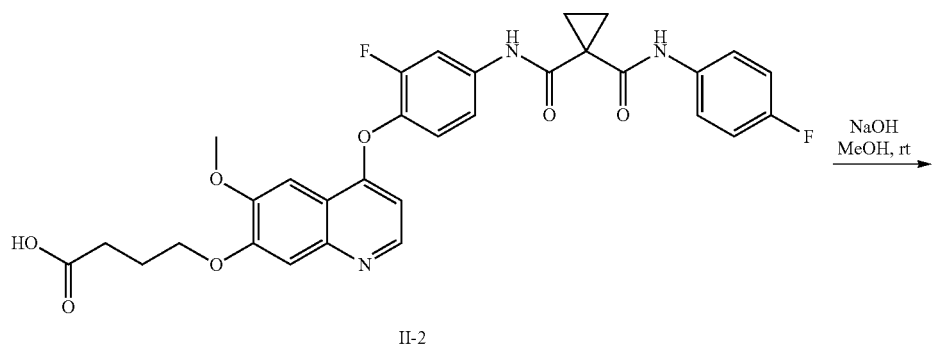

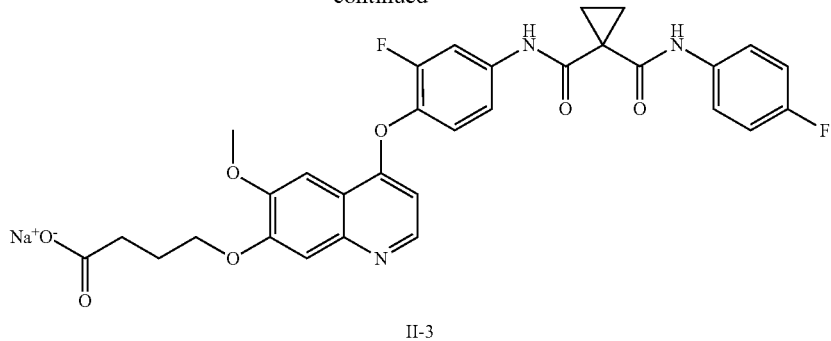

II-3

An aqueous solution of NaOH (0.041 N, 1 mL, 0.041 mmol) was added into a solution of 4-[[4-[2-fluoro-4-[[1-[(4-fluorophenyl)carbamoyl]cyclopropanecarbonyl]amino]phenoxy]-6-methoxy-7-quinolyl]oxy]butyric acid (II-2, 24 mg, 0.041 mmol) dissolved in methanol (0.5 mL). The mixture was stirred at room temperature for 16 h, diluted with water, and then freeze-dried to obtain sodium 4-[[4-[2-fluoro-4-[[1-[(4-fluorophenyl)carbamoyl]cyclopropanecarbonyl]amino]phenoxy]-6-methoxy-7-quinolyl]oxy]butyrate (II-3) (23 mg, yield: 92%). Analysis data: $^1$H-NMR (400 MHz, DMSO-d$_6$): δ=10.45 (s, 1H), 10.10 (s, 1H), 8.47 (d, J=5.4 Hz, 1H), 7.92 (d, J=11.1 Hz, 1H), 7.69-7.40 (m, 6H), 7.20-7.12 (m, 2H), 6.42-6.40 (m, 1H), 4.18 (t, J=6.6 Hz, 2H), 3.96 (s, 3H), 2.37 (d, J=6.9 Hz, 2H), 2.07-1.98 (m, 2H), 1.48 (s, 4H). Mass spectrum (ESI) m/z: 592.1 [M+H]$^+$.

Example 5

1,3-dihydroxy-2-(hydroxymethyl)propan-2-ammonium 4-[[4-[2-fluoro-4-[[1-[(4-fluorophenyl)carbamoyl]cyclopropanecarbonyl]amino]phenoxy]-6-methoxy-7-quinolyl]oxy]butyrate (II-4) is prepared according to the following reaction equation:

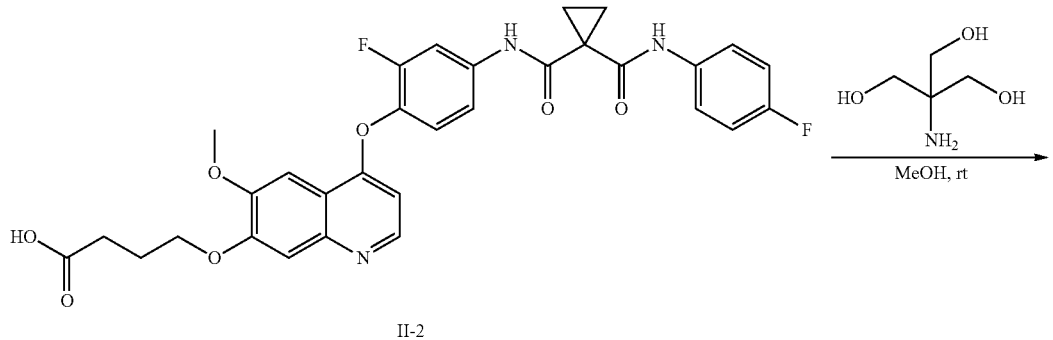

II-2

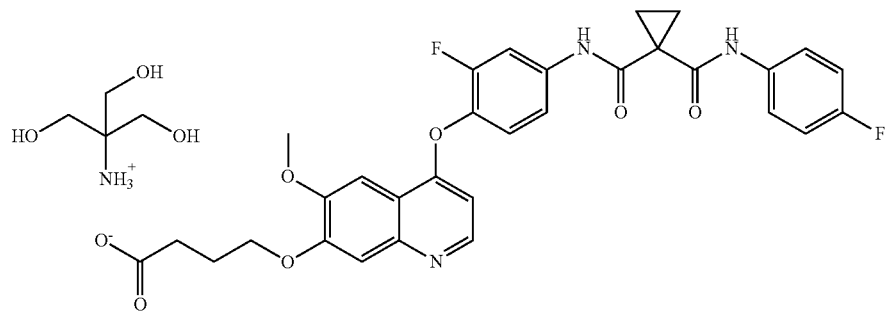

B-4

A methanol solution of 2-amino-2-(hydroxymethyl)propane-1,3-diol (0.041 N, 1 mL, 0.041 mmol) was added into a solution of 4-[[4-[2-fluoro-4-[[1-[(4-fluorophenyl)carbamoyl]cyclopropanecarbonyl]amino]phenoxy]-6-methoxy-7-quinolyl]oxy]butyric acid (II-2, 24 mg, 0.041 mmol) dissolved in methanol (0.5 mL). The obtained mixture was stirred at room temperature for 16 h, diluted with water, and then freeze-dried to obtain 1,3-dihydroxy-2-(hydroxymethyl)propan-2-ammonium 4-[[4-[2-fluoro-4-[[1-[(4-fluorophenyl)carbamoyl]cyclopropanecarbonyl]amino]phenoxy]-6-methoxy-7-quinolyl]oxy]butyrate (II-4) (27 mg, yield: 93%). Analysis data: $^1$H-NMR (400 MHz, DMSO-$d_6$): δ=10.41 (s, 1H), 10.03 (s, 1H), 8.47 (d, J=5.1 Hz, 1H), 7.94-7.87 (m, 1H), 7.68-7.39 (m, 6H), 7.19-7.12 (m, 2H), 6.43-6.41 (m, 1H), 5.12 (br, 2H), 4.18 (t, J=6.3 Hz, 2H), 3.96 (s, 3H), 3.44 (s, 6H), 2.50-2.42 (m, 2H), 2.09-2.00 (m, 2H), 1.48 (s, 4H). Mass spectrum (ESI) m/z: 592.1 [M+H]$^+$.

Example 6

5-[[4-[2-fluoro-4-[[1-[(4-fluorophenyl)carbamoyl]cyclopropanecarbonyl]amino]phenoxy]-6-methoxy-7-quinolyl]oxy]valeric acid (III-2) is prepared according to the following reaction equation:

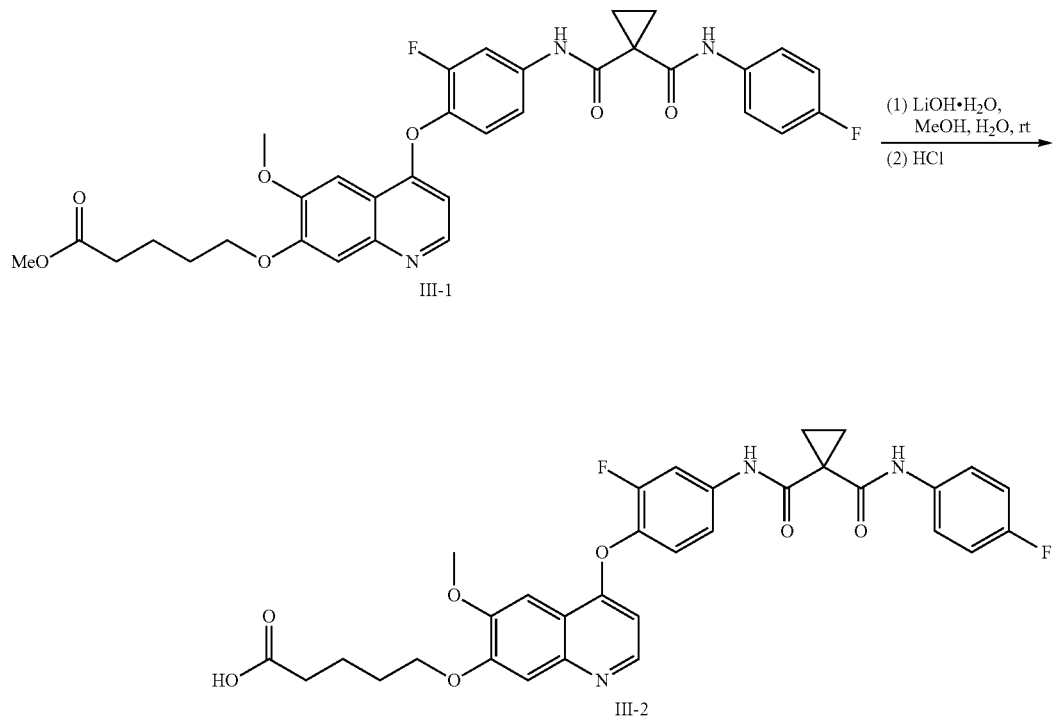

LiOH.H$_2$O (149 mg, 3.54 mmol) was added into a solution of methyl 5-[[4-[2-fluoro-4-[[1-[(4-fluorophenyl)carbamoyl]cyclopropanecarbonyl]amino]phenoxy]-6-methoxy-7-quinolyl]oxy]valerate (III-1, 220 mg, 0.354 mmol, prepared according to the method described in WO2013/040801A1) dissolved in methanol (3.0 mL) and water (1.0 mL). The obtained mixture was stirred at room temperature for 1 h, and the reaction solution was diluted with water and adjusted to pH 4 with HCl (1N). After filtration, the obtained solid product was collected and washed with acetonitrile, so as to obtain 5-[[4-[2-fluoro-4-[[1-[(4-fluorophenyl)carbamoyl]cyclopropanecarbonyl]amino]phenoxy]-6-methoxy-7-quinolyl]oxy]valeric acid (III-2) (184 mg, yield: 85%). Analysis data: $^1$H-NMR (400 MHz, DMSO-$d_6$): δ=12.12 (s, 1H), 10.51 (s, 1H), 10.01 (s, 1H), 8.76 (d, J=6.0 Hz, 1H), 8.00-7.96 (m, 1H), 7.71 (s, 1H), 7.67-7.51 (m, 5H), 7.19-7.15 (m, 2H), 6.83 (d, J=6.4 Hz, 1H), 4.24 (t, J=6.4 Hz, 2H), 4.03 (s, 3H), 2.37-2.33 (m, 2H), 1.90-1.86 (m, 2H), 1.76-1.70 (m, 2H), 1.53-1.47 (m, 4H). Mass spectrum (ESI) m/z: 606.1 [M+H]$^+$.

Example 7

Potassium 5-[[4-[2-fluoro-4-[[1-[(4-fluorophenyl)carbamoyl]cyclopropanecarbonyl]amino]phenoxy]-6-methoxy-7-quinolyl]oxy]valerate (III-3) is prepared according to the following reaction equation:

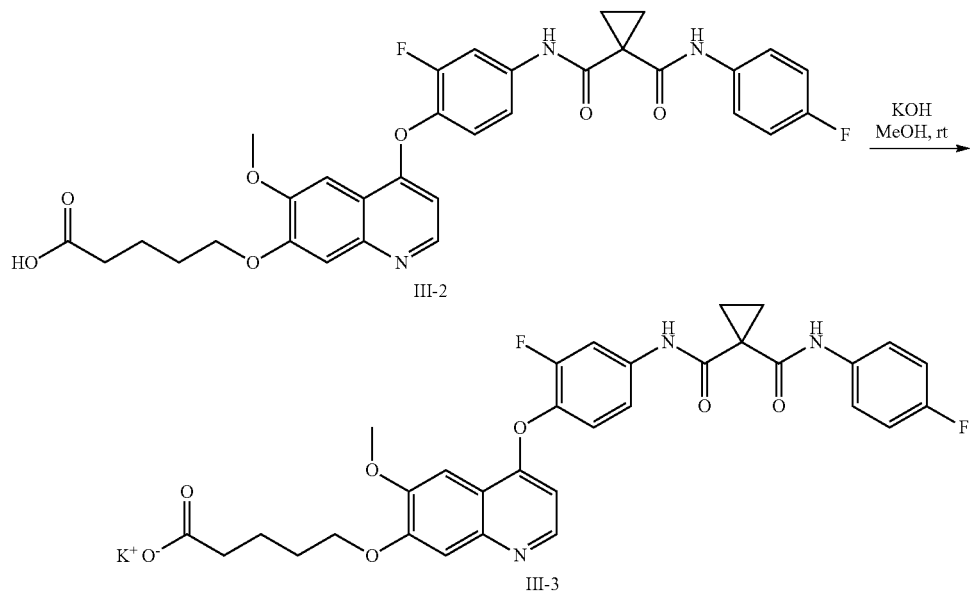

An aqueous solution of KOH (0.040 N, 1 mL, 0.040 mmol) was added into a solution of 5-[[4-[2-fluoro-4-[[1-[(4-fluorophenyl)carbamoyl]cyclopropanecarbonyl]amino]phenoxy]-6-methoxy-7-quinolyl]oxy]valeric acid (III-2, 24 mg, 0.040 mmol) dissolved in methanol (0.5 mL). The obtained mixture was stirred at room temperature for 16 h, diluted with water, and then freeze-dried to obtain potassium 5-[[4-[2-fluoro-4-[[1-[(4-fluorophenyl)carbamoyl]cyclopropanecarbonyl]amino]phenoxy]-6-methoxy-7-quinolyl]oxy]valerate (III-3) (24 mg, yield: 94%). Analysis data: $^1$H-NMR (400 MHz, DMSO-$d_6$): δ=10.35 (s, br, 2H), 8.47 (d, J=5.4 Hz, 1H), 7.94-7.89 (m, 1H), 7.68-7.38 (m, 6H), 7.19-7.13 (m, 2H), 6.42-6.40 (m, 1H), 4.15 (t, J=6.3 Hz, 2H), 3.95 (s, 3H), 2.28-2.21 (m, 2H), 1.87-1.66 (m, 4H), 1.47 (m, 4H). Mass spectrum (ESI) m/z: 606.1 [M+H]$^+$.

Example 8

Triethylammonium 5-[[4-[2-fluoro-4-[[1-[(4-fluorophenyl)carbamoyl]cyclopropanecarbonyl]amino]phenoxy]-6-methoxy-7-quinolyl]oxy]valerate (III-4) is prepared according to the following reaction equation:

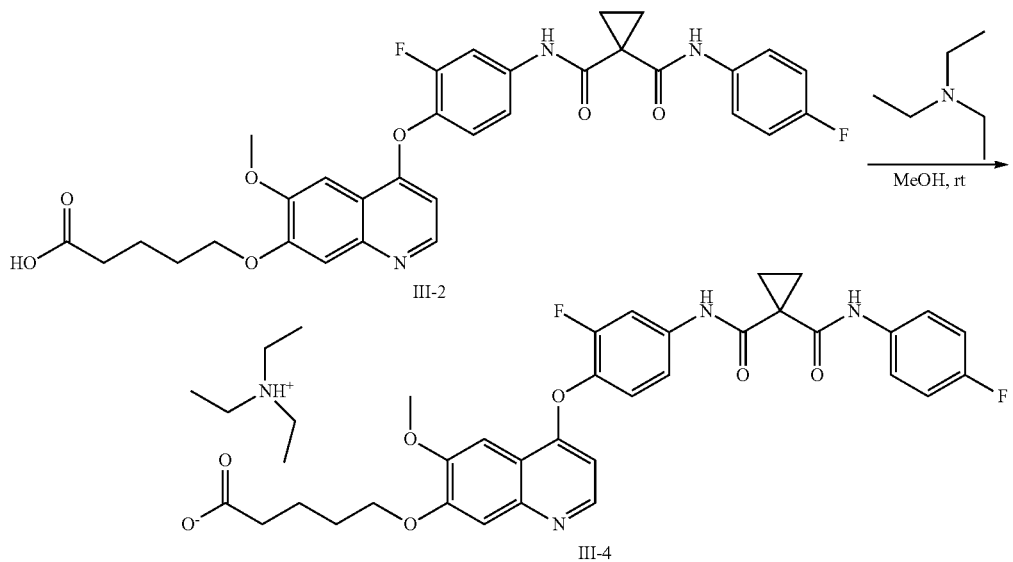

An acetonitrile solution of triethylamine (0.040 N, 1 mL, 0.040 mmol) was added into a solution of 5-[[4-[2-fluoro-4-[[1-[(4-fluorophenyl)carbamoyl]cyclopropanecarbonyl]amino]phenoxy]-6-methoxy-7-quinolyl]oxy]valeric acid (III-2, 24 mg, 0.040 mmol) dissolved in methanol (0.3 mL) and water (0.5 mL). The obtained mixture was stirred at room temperature for 16 h, diluted with water, and then freeze-dried to obtain triethylammonium 5-[[4-[2-fluoro-4-[[1-[(4-fluorophenyl)carbamoyl]cyclopropanecarbonyl]amino]phenoxy]-6-methoxy-7-quinolyl]oxy]valerate (III-4) (24 mg, yield: 86%). Analysis data: $^1$H-NMR (400 MHz, DMSO-$d_6$): δ=12.07 (s, 1H), 10.40 (s, 1H), 10.02 (s, 1H), 8.49 (d, J=5.1 Hz, 1H), 7.94-7.89 (m, 1H), 7.67-7.40 (m, 6H), 7.19-7.13 (m, 2H), 6.44 (d, J=4.5 Hz, 1H), 4.17 (t, J=6.3 Hz, 2H), 3.96 (s, 3H), 3.12-3.06 (m, 2.5 H), 2.34 (d, J=6.9 Hz, 1H), 2.28-2.21 (m, 2H), 1.87-1.68 (m, 4H), 1.48 (m, 4H), 1.19 (t, J=7.2 Hz, 2.5 H). Mass spectrum (ESI) m/z: 606.1 [M+H]$^+$.

Example 9

6-[[4-[2-fluoro-4-[[1-[(4-fluorophenyl)carbamoyl]cyclopropanecarbonyl]amino]phenoxy]-6-methoxy-7-quinolyl]oxy]caproic acid (IV-2) is prepared according to the following reaction equation:

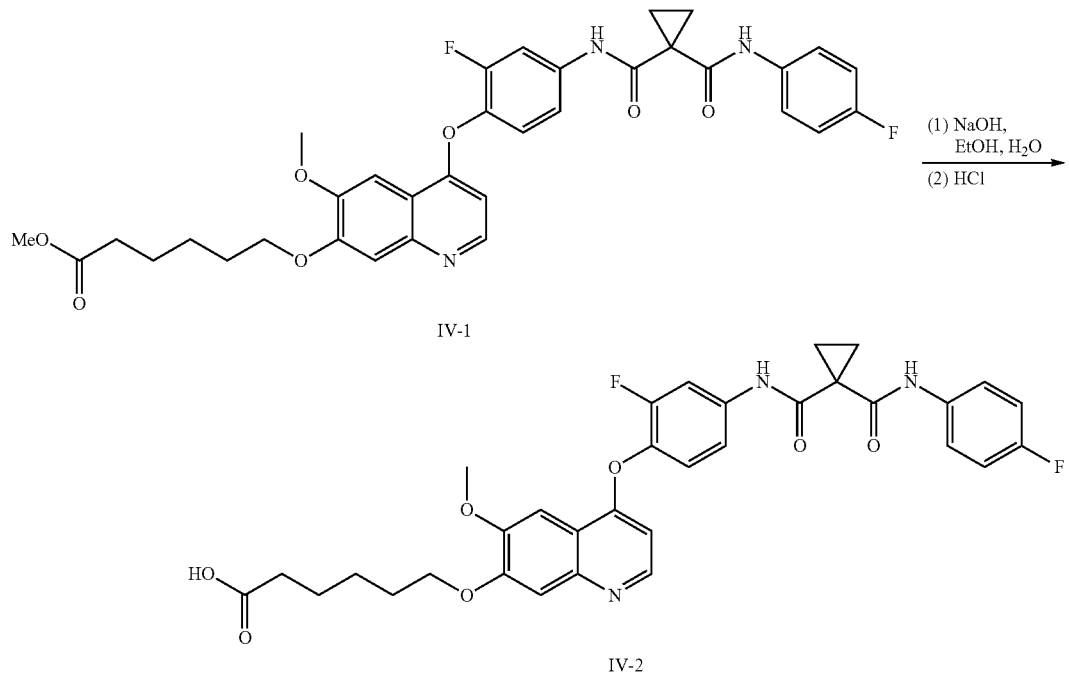 [SMILES: COC(=O)CCCCCOc1cc2nccc(Oc3ccc(NC(=O)C4(C(=O)Nc5ccc(F)cc5)CC4)cc3F)c2cc1OC ; "IV-1" ; COc1cc2c(Oc3ccc(NC(=O)C4(C(=O)Nc5ccc(F)cc5)CC4)cc3F)ccnc2cc1OCCCCCC(=O)O ; "IV-2"]

Under stirring, NaOH (4.4 g, 110 mmol) was added dropwise into a solution of methyl 6-[[4-[2-fluoro-4-[[1-[(4-fluorophenyl)carbamoyl]cyclopropanecarbonyl]amino]phenoxy]-6-methoxy-7-quinolyl]oxy]caproate (IV-1, 35.0 g, 55.2 mmol, prepared according to the method described in WO2013/040801A1) dissolved in ethanol (350 mL). After the dropwise addition was completed, water (50 mL) was added. The obtained mixture was stirred at 20-25° C. for 18 h. The reaction mixture was diluted with water (100 mL), stirred for 20 min, and adjusted to pH 3-4 with HCl (1N). The reaction mixture was concentrated under reduced pressure to distillate ethanol (about 300 mL), and then filtrated to collect the solid product. The obtained crude product (28.4 g) was purified by silica gel column chromatography (eluent: ethyl acetate:methanol=1:1, v/v) to obtain 6-[[4-[2-fluoro-4-[[1-[(4-fluorophenyl)carbamoyl]cyclopropanecarbonyl]amino]phenoxy]-6-methoxy-7-quinolyl]oxy]caproic acid (IV-2) (9.6 g, yield: 28.1%). Analysis data: $^1$H-NMR (400 MHz, DMSO-$d_6$): δ=8.17 (d, J=8.0 Hz, 1H), 7.81 (dd, J=2.8, 13.4 Hz, 1H) 7.62 (m, 2H), 7.51 (m, 4H), 7.39 (t, J=2.4 Hz, 2H), 6.44 (d, J=20.0 Hz, 1H), 4.13 (t, J=8.5 Hz, 2H), 3.85 (s, 3H), 2.27 (t, J=4.0 Hz, 2H), 1.83 (m, 2H), 1.68-1.46 (m, 8H). Mass spectrum (ESI) m/z: 620.2 [M+H]$^+$.

Example 10

Sodium 6-[[4-[2-fluoro-4-[[1-[(4-fluorophenyl)carbamoyl]cyclopropanecarbonyl]amino]phenoxy]-6-methoxy-7-quinolyl]oxy]caproate (IV-3) is prepared according to the following reaction equation:

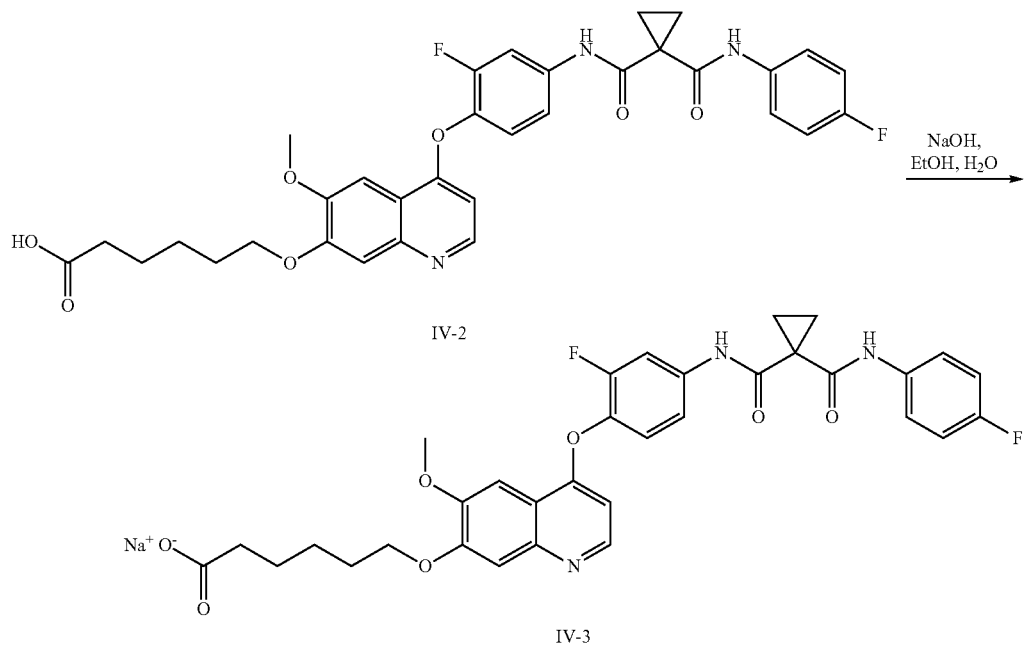

A solution of NaOH (34.29 mg, 0.857 mmol) dissolved in water (5 mL) was added into a solution of 6-[[4-[2-fluoro-4-[[1-[(4-fluorophenyl)carbamoyl]cyclopropanecarbonyl]amino]phenoxy]-6-methoxy-7-quinolyl]oxy]caproic acid (IV-2, 500 mg, 0.807 mmol) dissolved in ethanol (20 mL). The obtained mixture was stirred at room temperature for 30 min, and distillated under reduced pressure (the temperature is controlled at 40° C.), so as to obtain sodium 6-[[4-[2-fluoro-4-[[1-[(4-fluorophenyl)carbamoyl]cyclopropanecarbonyl]amino]phenoxy]-6-methoxy-7-quinolyl]oxy]caproate (IV-3) (617.2 mg, yield: 96%). Mass spectrum (ESI) m/z: 620.2 [M+H]$^+$.

Example 11

Potassium 6-[[4-[2-fluoro-4-[[1-[(4-fluorophenyl)carbamoyl]cyclopropanecarbonyl]amino]phenoxy]-6-methoxy-7-quinolyl]oxy]caproate (IV-4) is prepared according to the following reaction equation:

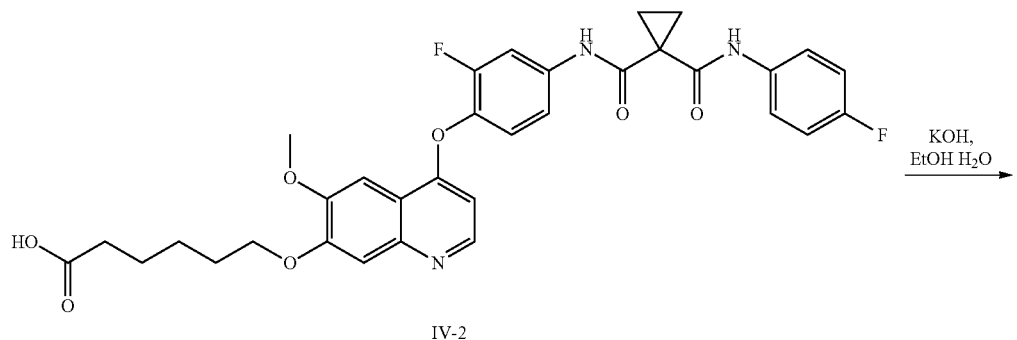

-continued

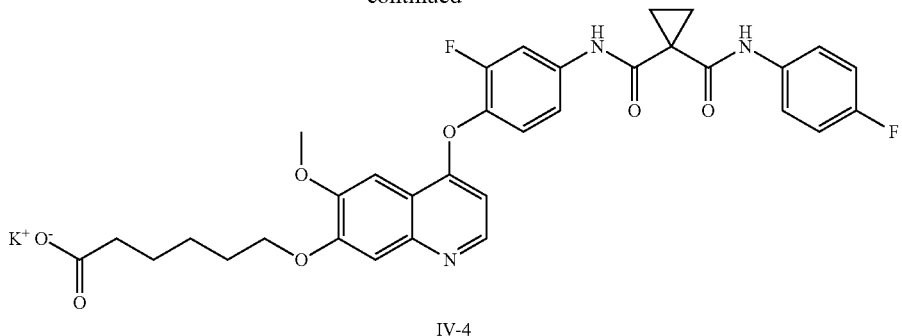

IV-4

A solution of KOH (55.44 mg, 0.988 mmol) dissolved in water (5 mL) was added into a solution of 6-[[4-[2-fluoro-4-[[1-[(4-fluorophenyl)carbamoyl]cyclopropanecarbonyl]amino]phenoxy]-6-methoxy-7-quinolyl]oxy]caproic acid (IV-2, 500 mg, 0.807 mmol) dissolved in ethanol (20 mL). The obtained mixture was stirred at room temperature for 30 min, and distillated under reduced pressure (the temperature is controlled at 40° C.), so as to obtain potassium 6-[[4-[2-fluoro-4-[[1-[(4-fluorophenyl)carbamoyl]cyclopropanecarbonyl]amino]phenoxy]-6-methoxy-7-quinolyl]oxy]caproate (IV-4) (555.46 mg, yield: 100%). Mass spectrum (ESI) m/z: 620.2 $[M+H]^+$.

Example 12

Calcium 6-[[4-[2-fluoro-4-[[1-[(4-fluorophenyl)carbamoyl]cyclopropanecarbonyl]amino]phenoxy]-6-methoxy-7-quinolyl]oxy]caproate (1:1) (IV-5) is prepared according to the following reaction equation:

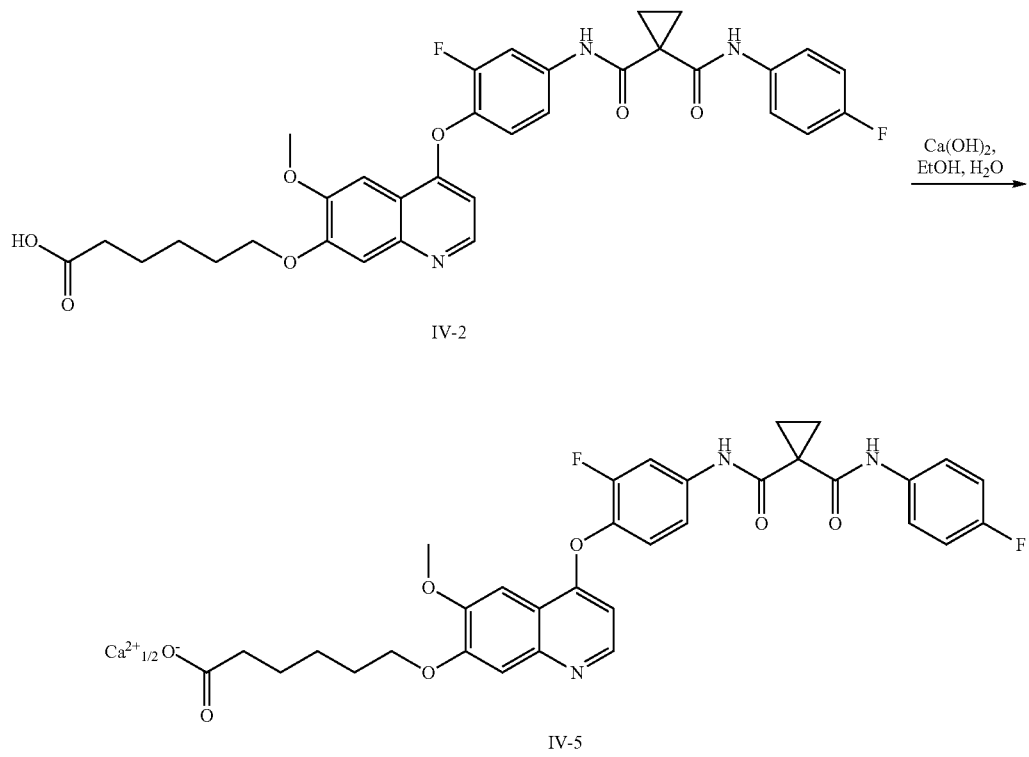

A solution of Ca(OH)₂ (30.245 mg, 0.408 mmol) dissolved in water (5 mL) was added into a solution of 6-[[4-[2-fluoro-4-[[1-[(4-fluorophenyl)carbamoyl]cyclopropanecarbonyl]amino]phenoxy]-6-methoxy-7-quinolyl]oxy]caproic acid (IV-2, 500 mg, 0.807 mmol) dissolved in ethanol (20 mL). The obtained mixture was stirred at room temperature for 30 min, and distilled under reduced pressure (the temperature is controlled at 40° C.), so as to obtain calcium 6-[[4-[2-fluoro-4-[[1-[(4-fluorophenyl)carbamoyl]cyclopropanecarbonyl]amino]phenoxy]-6-methoxy-7-quinolyl]oxy]caproate (1:1) (IV-5) (309.19 mg, yield: 58%). Mass spectrum (ESI) m/z: 620.2 [M+H]⁺.

Example 13

1,3-dihydroxy-2-(hydroxymethyl)propan-2-ammonium 6-[[4-[2-fluoro-4-[[1-[(4-fluorophenyl)carbamoyl]cyclopropanecarbonyl]amino]phenoxy]-6-methoxy-7-quinolyl]oxy]caproate (IV-6) is prepared according to the following reaction equation:

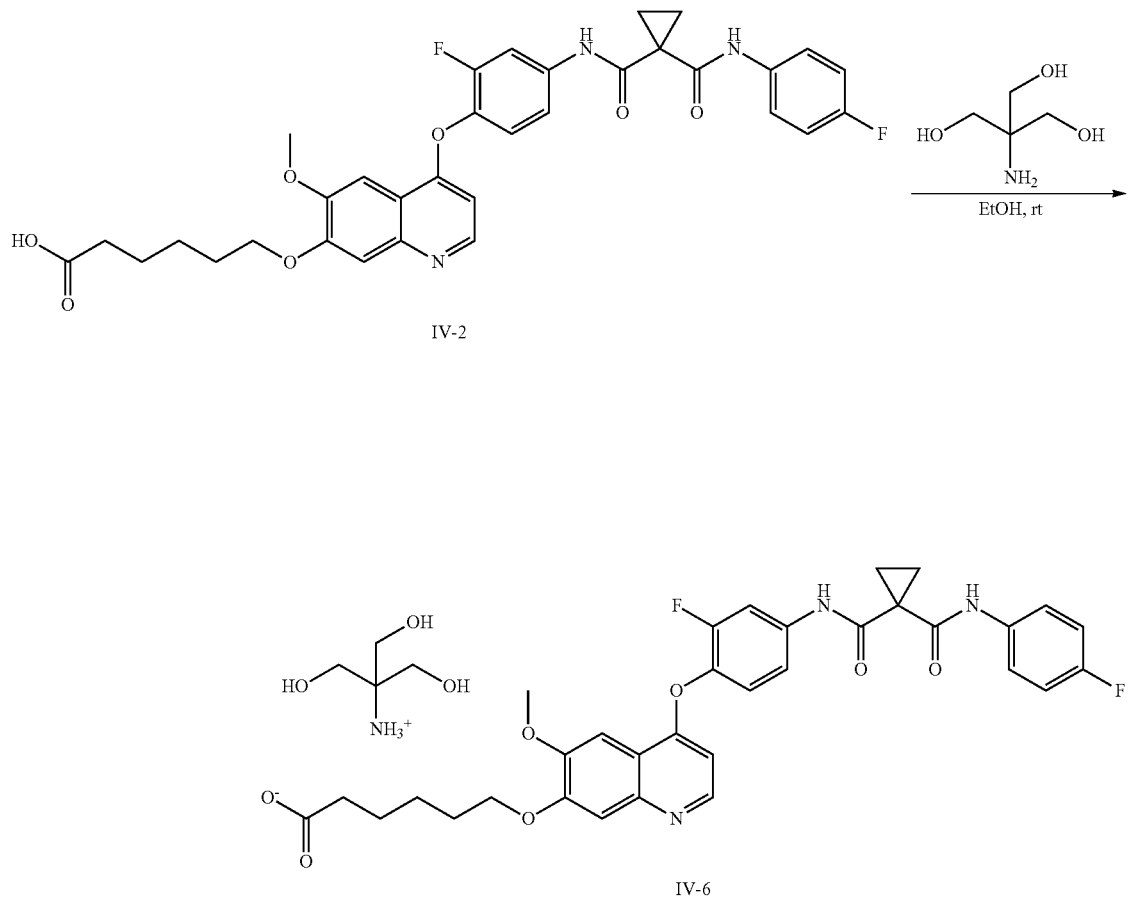

A solution of 2-amino-2-(hydroxymethyl)propane-1,3-diol (102.75 mg, 0.848 mmol) dissolved in water (5 mL) was added into a solution of 6-[[4-[2-fluoro-4-[[1-[(4-fluorophenyl)carbamoyl]cyclopropanecarbonyl]amino]phenoxy]-6-methoxy-7-quinolyl]oxy]caproic acid (IV-2, 500 mg, 0.807 mmol) dissolved in ethanol (20 mL). The obtained mixture was stirred at room temperature for 1 h, and distilled under reduced pressure (the temperature is controlled at 40° C.), so as to obtain a light yellow oil product, which is dried to obtain 1,3-dihydroxy-2-(hydroxymethyl)propan-2-ammonium 6-[[4-[2-fluoro-4-[[1-[(4-fluorophenyl)carbamoyl]cyclopropanecarbonyl]amino]phenoxy]-6-methoxy-7-quinolyl]oxy]caproate (IV-6) (394.11 mg, yield: 66%). Mass spectrum (ESI) m/z: 620.2 [M+H]⁺.

Example 14

7-[[4-[2-fluoro-4-[[1-[(4-fluorophenyl)carbamoyl]cyclopropanecarbonyl]amino]phenoxy]-6-methoxy-7-quinolyl]oxy]heptanoic acid is prepared according to the following reaction equation:

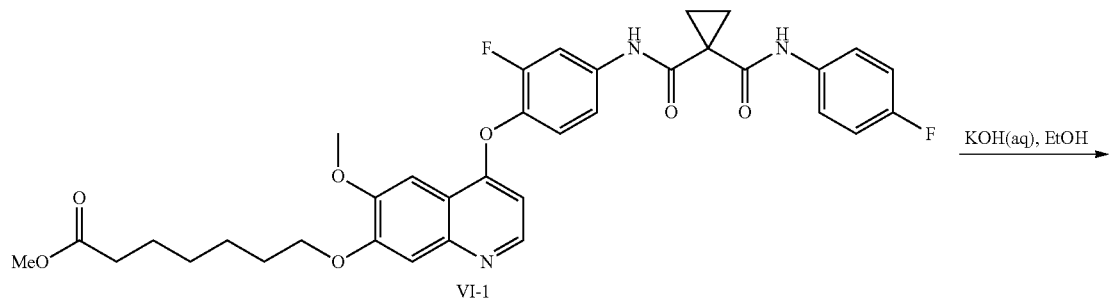

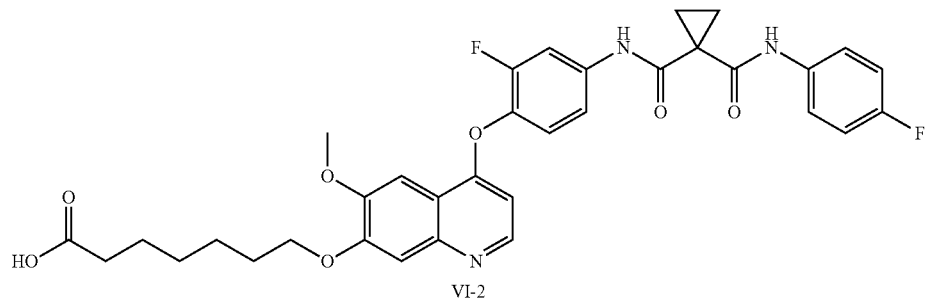

A solution of potassium hydroxide (86.4 mg) dissolved in water (2 mL) was added into a solution of methyl 7-[[4-[2-fluoro-4-[[1-[(4-fluorophenyl)carbamoyl]cyclopropanecarbonyl]amino]phenoxy]-6-methoxy-7-quinolyl]oxy]heptanoate (VI-1, 1.0 g, 1.53 mmol) dissolved in ethanol (10 mL). The obtained mixture was stirred at room temperature for 5 h. Then, the reaction solution was adjusted to about pH 3 and extracted with ethyl acetate. The obtained extract was evaporated to dry under reduced pressure so as to obtain the target product (VI-2) (715 mg, yield: 74%). Mass spectrum (ESI) m/z: 635.4 $[M+H]^+$.

Example 15

7-[[4-[2-fluoro-4-[[1-[(3-chlorophenyl)carbamoyl]cyclopropanecarbonyl]amino]phenoxy]-6-methoxy-7-quinolyl]oxy]heptanoic acid is prepared according to the following reaction equation:

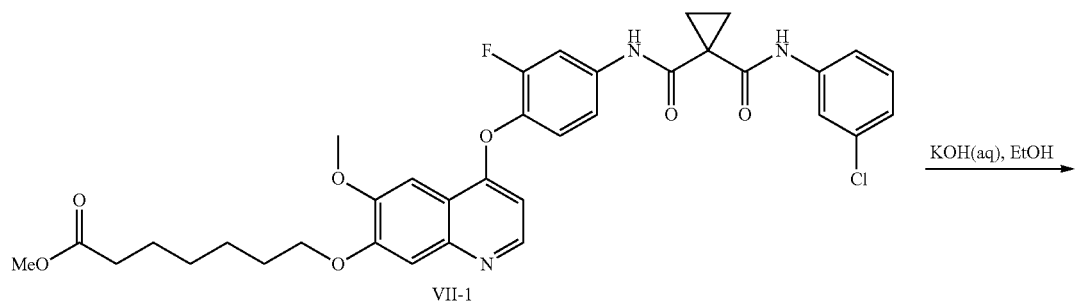

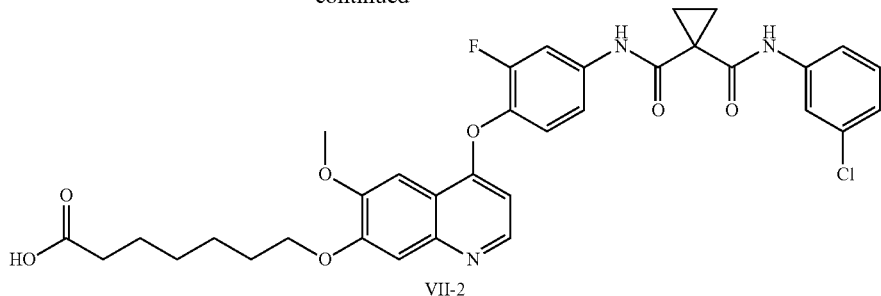

A solution of potassium hydroxide (84.3 mg) dissolved in water (2 mL) was added into a solution of methyl 7-[[4-[2-fluoro-4-[[1-[(3-chlorophenyl)carbamoyl]cyclopropanecarbonyl]amino]phenoxy]-6-methoxy-7-quinolyl]oxy]heptanoate (VII-1, 1.0 g, 1.51 mmol) dissolved in ethanol (10 mL). The obtained mixture was stirred at room temperature for 4.5 h. Then, the reaction solution was adjusted to about pH 3 and extracted with ethyl acetate. The obtained extract was evaporated to be dry under reduced pressure so as to obtain the target product (VII-2) (700 mg, yield: 71%). Mass spectrum (ESI) m/z: 651.1 $[M+H]^+$.

Example 16

Calcium 7-[[4-[2-fluoro-4-[[1-[(3-chlorophenyl)carbamoyl]cyclopropanecarbonyl]amino]phenoxy]-6-methoxy-7-quinolyl]oxy]heptanoate is prepared according to the following reaction equation:

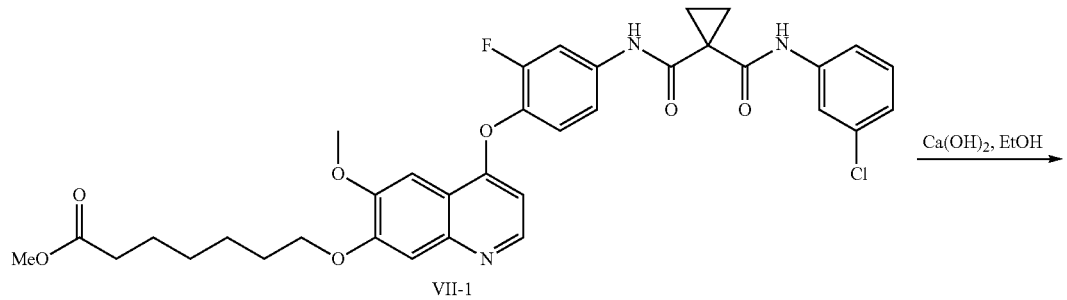

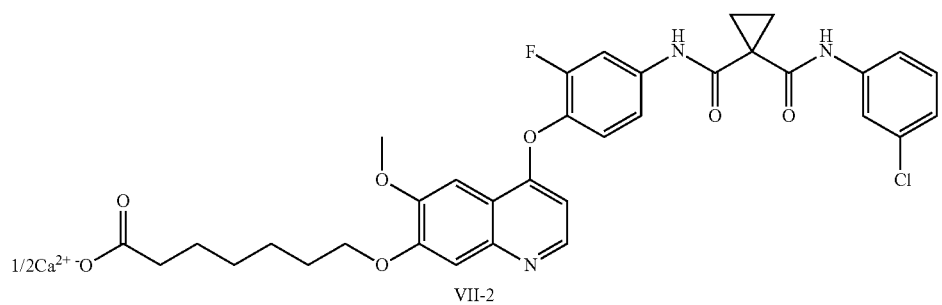

A solution of calcium hydroxide (43.1 mg) dissolved in water (5 mL) was added into a solution of 7-[[4-[2-fluoro-4-[[1-[(3-chlorophenyl)carbamoyl]cyclopropanecarbonyl]amino]phenoxy]-6-methoxy-7-quinolyl]oxy]pentanoic acid (VIII-1, 1.0 g, 1.54 mmol) dissolved in ethanol (10 mL). The obtained mixture was stirred at about 50° C. for 4 h. Then, the reaction solution was evaporated to be dry to obtain the target product (VIII-2) (909 mg, yield: 90%).

Example 17

2-[[4-[2-fluoro-4-[[1-[(4-fluorophenyl)carbamoyl]cyclopropanecarbonyl]amino]phenoxy]-6-isopropoxy-7-quinolyl]oxy]acetic acid is prepared according to the following reaction equation:

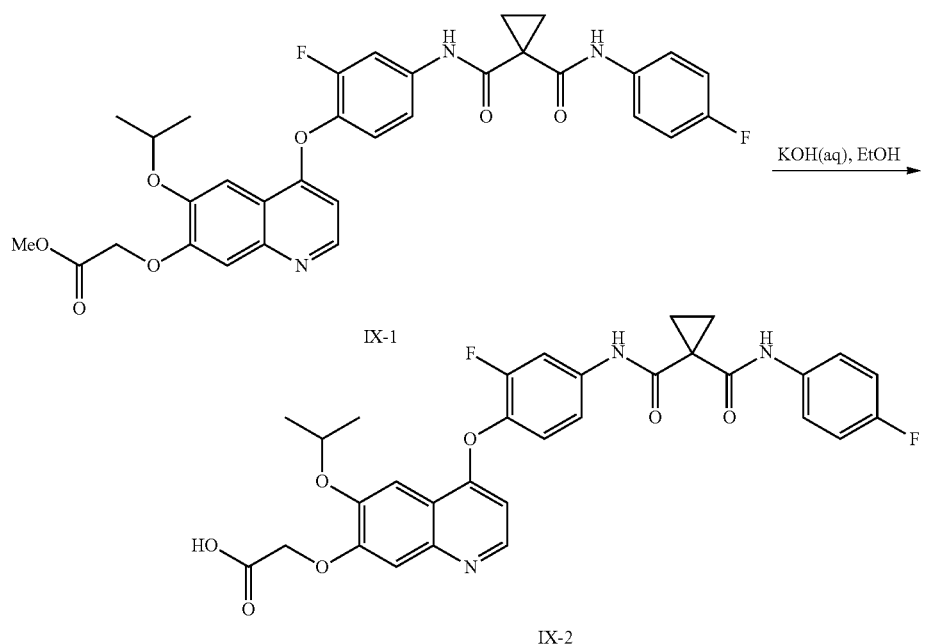

A solution of potassium hydroxide (147.8 mg) dissolved in water (5 mL) was added into a solution of methyl 2[[4-[2-fluoro-4-[[1-[(4-fluorophenyl)carbamoyl]cyclopropanecarbonyl]amino]phenoxy]-6-isopropoxy-7-quinolyl]oxy]acetate (IX-1, 800 mg, 1.32 mmol) dissolved in ethanol (12 mL). The obtained mixture was stirred at room temperature for 4 h. Then, the reaction solution was adjusted to about pH 3 and extracted with ethyl acetate. The obtained extract was evaporated to be dry under reduced pressure so as to obtain the target product (IX-2) (633 mg, yield: 81%). Mass spectrum (ESI) m/z: 593.3 [M+H]$^+$.

Example 18

Potassium 2-[[4-[2-fluoro-4-[[1-[(4-fluorophenyl)carbamoyl]cyclopropanecarbonyl]amino]phenoxy]-6-ethoxy-7-quinolyl]oxy]acetate is prepared according to the following reaction equation:

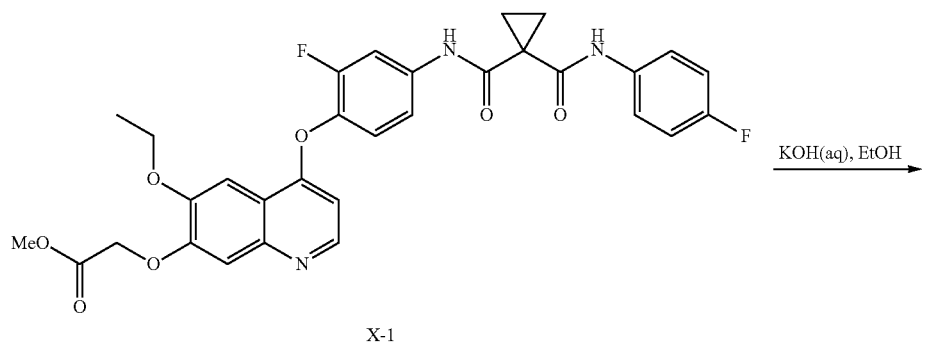

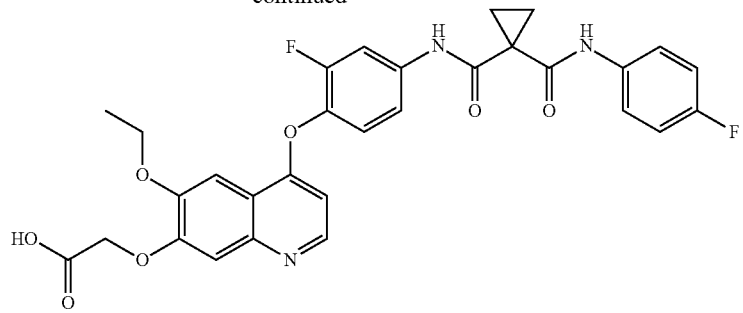

X-2

A solution of potassium hydroxide (57.0 mg) dissolved in water (5 mL) was added into a solution of 2-[[4-[2-fluoro-4-[[1-[(4-fluorophenyl)carbamoyl]cyclopropanecarbonyl]amino]phenoxy]-6-ethoxy-7-quinolyl]oxy]acetatic acid (X-1, 500 mg, 0.865 mmol) dissolved in ethanol (10 mL). The obtained mixture was stirred at room temperature for 4 h. Then, the reaction solution was evaporated to be dry under reduced pressure so as to obtain the target product (X-2) (513 mg, yield: 96%).

Example 19

Ammonium 2-[[4-[2-fluoro-4-[[1-[(4-fluorophenyl)carbamoyl]cyclopropanecarbonyl]amino]phenoxy]-6-ethoxy-7-quinolyl]oxy]acetate is prepared according to the following reaction equation:

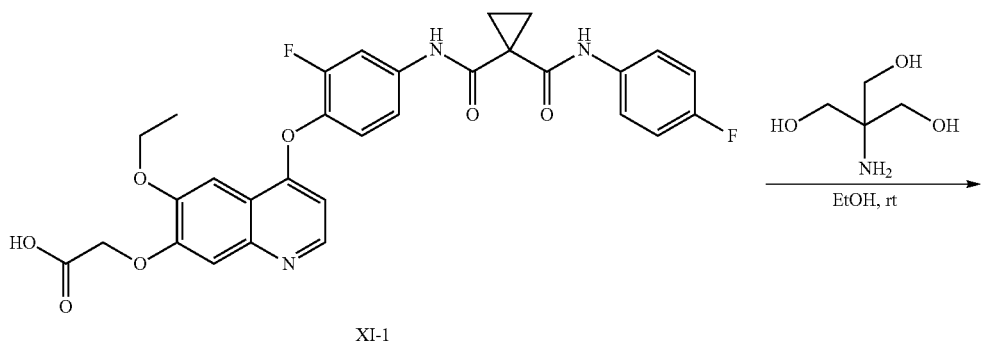

XI-1

XI-2

A solution of 2-amino-2-(hydroxymethyl)propane-1,3-diol (105 mg, 0.865 mmol) dissolved in water (5 mL) was added into a solution of 2-[[4-[2-fluoro-4-[[1-[(4-fluorophenyl)carbamoyl]cyclopropanecarbonyl]amino]phenoxy]-6-ethoxy-7-quinolyl]oxy]acetic acid (XI-1, 500 mg, 0.865 mmol) dissolved in ethanol (15 mL). The obtained mixture was stirred at room temperature for 3 h. Then, the reaction solution was evaporated to be dry under reduced pressure so as to obtain the target product (XI-2) (450 mg, yield: 74%).

Example 20

Biochemical inhibitory activity against AXL and VEGFR2 kinases: the biochemical $IC_{50}$ values of the compound according to the present application for inhibiting AXL and VEGFR2 kinases were measured by ProQinase GmbH Company (Breisacher Str. 117, D-79106 Freiburg, Germany, www.proqinase.com). The specific steps are described as follows:

Firstly, the compound according to the present application was dissolved in dimethyl sulfoxide (DMSO) to prepare a stock solution of $1\times10^{-3}$ M. 10 different concentrations (from $1\times10^5$ M to $3\times10^{-10}$ M) were prepared by the serial semi-logarithmic dilution.

The biochemical activities of AXL and VEGFR2 were determined by the radioactive protein kinase assay (33PanQinase® Activity Assay). The assay was performed using a FlashPlates™ 96-well plate manufactured by Perkin Elmer (Boston, Mass., USA) with a reaction volume of 50 μL. The reaction mixture was added by a dropper in the following four steps:

(1) 20 μL of buffer solution (standard buffer);
(2) 5 μL of an aqueous solution of ATP;
(3) 5 μL of the compound (10% DMSO solution);
(4) 10 μL of a substrate/10 μL of a solution of the kinase.

The solution to be measured contains HEPES-NaOH (70 mM, pH=7.5), $MgCl_2$ (3 mM), $MnCl_2$ (3 mM), Na-orthovanadate (3 μM), DTT (1.2 mM), $PEG_{20000}$ (50 μg/mL), ATP (in a concentration that is same as $K_m$ of the kinase and varies depending on different kinases), [γ-$^{33}$P]-ATP (about $4\times10^5$ cpm/well), kinase and substrate.

The used amounts of kinase and substrate per well are summarized in Table 1:

TABLE 1

Measurement Parameters

| No. | Kinase | Kinase Concentration (ng/50 μL) | Kinase Concentration (nM) | ATP Concentration (μM) | Substrate Name | Substrate (μg/50 μL) |
|---|---|---|---|---|---|---|
| 1 | AXL | 25 | 6.5 | 0.3 | Poly(Glu, Tyr) 4:1 | 0.250 |
| 2 | VEGFR2 | 20 | 4.6 | 1.0 | Poly(Glu, Tyr) 4:1 | 0.125 |

The reaction was carried out at 30° C. for 60 minutes, and 50 μL of 2% (v/v) phosphoric acid was added to terminate the reaction. The reaction mixture in each well was aspirated and washed twice with 200 μL of 0.9% (w/v) NaCl solution. The amount of the incorporation of $^{33}P$ was determined by using a microplate scintillation counter.

The results are summarized in Table 2.

TABLE 2

Biochemical activity of the compounds against two kinases AXL and VEGFR2.

| | Biochemical $IC_{50}$ (nM) | |
|---|---|---|
| Example | AXL | VEGFR2 |
| 1 | 55.3 | 24.5 |
| 3 | 9.86 | 6.56 |
| 4 | 9.05 | 8.03 |
| 6 | 7.49 | 6.60 |
| 8 | 6.08 | 8.66 |
| 9 | 10.2 | 16.0 |
| 10 | 11.9 | 13.9 |
| 11 | 14.9 | 13.6 |
| 12 | 10.7 | 10.4 |
| 13 | 8.63 | 12.6 |
| 14 | 13.7 | 13.6 |
| 16 | 19.8 | 18.9 |
| 18 | 10.7 | 9.86 |

As described previously, the compounds of the present application have strong inhibitory activity against both of the two kinases AXL and VEGFR2, and the $IC_{50}$ values for AXL are in a range of 6.08-55.3 nM, and the IC50 values for VEGFR2 are in a range of 6.56-24.5 nM. Therefore, the compounds in this application can be used to treat diseases caused by abnormal activities of these kinases, for example, tumors, etc.

Example 21: Composition and Preparation of Medicine: Tablets (mg/Tablet)

compound prepared in Example 1:100;
lactose, Ph EUR: 182.75;
sodium carboxymethyl cellulose: 12.0;
corn starch slurry (5 w/v %): 2.25; and
magnesium stearate: 3.0;
suitable human subjects: those having a disease caused by abnormality of AXL protein kinase and/or VEGFR2 protein kinase.

Example 22: Composition and Preparation of Medicine: Tablets (mg/Tablet)

compound prepared in Example 5: 100;
other components and contents thereof are same as in Example 21;
suitable human subjects: those with a disease caused by abnormality of AXL protein kinase and/or VEGFR2 protein kinase.

Example 23: Composition and Preparation of Medicine: Tablets (mg/Tablet)

compound prepared in Example 9: 50;
lactose, PhEUR: 223.75;
sodium carboxymethyl cellulose: 6.0;
corn starch: 15.0;
polyvinylpyrrolidone (5 w/v %): 2.25; and
magnesium stearate: 3.0;
suitable human subjects: those having a disease caused by abnormality of AXL protein kinase and/or VEGFR2 protein kinase.

Example 24: Composition and Preparation of Medicine: Tablets (mg/Tablet)

compound prepared in Example 9: 50;
other components and contents thereof are same as in Example 23;
suitable human subjects: those with a disease caused by abnormality of AXL protein kinase and/or VEGFR2 protein kinase.

Example 25: Composition and Preparation of Medicine: Tablets (mg/Tablet)

compound prepared in Example 13: 1.0;
lactose, PhEUR: 93.25;
sodium carboxymethyl cellulose: 4.0;
corn starch slurry (5 w/v %): 0.75; and
magnesium stearate: 76;
suitable human subjects: those having a disease caused by abnormality of AXL protein kinase and/or VEGFR2 protein kinase.

Example 26: Composition and Preparation of Medicine: Tablets (mg/Tablet)

compound prepared in Example 13: 1.0;
other components and contents thereof are same as in Example 25;
suitable human subjects: those with a disease caused by abnormality of AXL protein kinase and/or VEGFR2 protein kinase.

Example 27: Composition and Preparation of Medicine: Capsules (mg/Capsule)

compound prepared in Example 7: 10.0;
lactose, Ph EUR: 488.5; and
magnesium: 1.5;
suitable human subjects: those having a disease caused by abnormality of AXL protein kinase and/or VEGFR2 protein kinase.

Example 28: Composition and Preparation of Medicine: Capsules (mg/Capsule)

compound prepared in Example 2: 10.0;
other components and contents thereof are same as in Example 27;
suitable human subjects: those having a disease caused by abnormality of AXL protein kinase and/or VEGFR2 protein kinase.

Example 29: Composition and Preparation of Medicine: Injection (50 mg/mL)

compound prepared in Example 6: 5%;
1 M sodium hydroxide solution: 15%;
0.1 M hydrochloric acid solution (adjusting pH=7.6);
polyethylene glycol 400: 5%; and
the remaining of 100%: water for injection;

suitable human subjects: those having a disease caused by abnormality of AXL protein kinase and/or VEGFR2 protein kinase.

Example 30: Composition and Preparation of Medicine: Injection (50 mg/mL)

compound prepared in Example 12: 5%;
other components and contents thereof are same as in Example 29; and
the remaining of 100%: water for injection;
suitable human subjects: those having a disease caused by abnormality of AXL protein kinase and/or VEGFR2 protein kinase.

Example 31: Composition and Preparation of Medicine: Injection (10 mg/mL)

compound prepared in Example 11: 1%;
disodium hydrogen phosphate BP: 3.6%;
0.1 M sodium hydroxide solution: 15%; and
the remaining of 100%: water for injection;
suitable human subjects: those having a disease caused by abnormality of AXL protein kinase and/or VEGFR2 protein kinase.

Example 32: Composition and Preparation of Medicine: Injection (10 mg/mL)

compound prepared in Example 9: 1%;
other components and contents thereof are same as in Example 31; and
the remaining of 100%: water for injection;
suitable human subjects: those having a disease caused by abnormality of AXL protein kinase and/or VEGFR2 protein kinase.

Example 33: Composition and Preparation of Medicine: Injection (1 mg/mL)

compound prepared in Example 6: 0.1%;
disodium hydrogen phosphate BP: 2.26%;
citric acid: 0.38%;
polyethylene glycol 400: 3.5%; and
the remaining of 100%: water for injection;
suitable human subjects: those having a disease caused by abnormality of AXL protein kinase and/or VEGFR2 protein kinase.

Example 34: Composition and Preparation of Medicine: Injection (1 mg/mL) (pH was Adjusted to 6)

compound prepared in Example 10: 0.1%;
other components and contents thereof are same as in Example 33;
the remaining of 100%: water for injection;
suitable human subjects: those having a disease caused by abnormality of AXL protein kinase and/or VEGFR2 protein kinase.

Example 35: Composition and Preparation of Medicine: Aerosol (mg/mL)

compound prepared in Example 1: 10;
sorbitan monooleate: 13.5;
trichlorofluoromethane: 910.0; and
dichlorodifluoromethane: 490.0;
suitable human subjects: those having a disease caused by abnormality of AXL protein kinase and/or VEGFR2 protein kinase.

Example 36: Composition and Preparation of Medicine: Aerosol (mg/mL)

compound prepared in Example 3: 10;
other components and contents thereof are same as in Example 35;
suitable human subjects: those having a disease caused by abnormality of AXL protein kinase and/or VEGFR2 protein kinase.

Example 37: Composition and Preparation of Medicine: Aerosol (mg/mL)

compound prepared in Example 4: 0.2;
sorbitan monooleate: 0.27;
trichlorofluoromethane: 70.0;
dichlorodifluoromethane: 280.0; and
dichlorotetrafluoroethane: 1094.0;
suitable human subjects: those having a disease caused by abnormality of AXL protein kinase and/or VEGFR2 protein kinase.

Example 38: Composition and Preparation of Medicine: Aerosol (mg/mL)

compound prepared in Example 7: 0.2;
other components and contents thereof are same as in Example 37;
suitable human subjects: those having a disease caused by abnormality of AXL protein kinase and/or VEGFR2 protein kinase.

Example 39: Composition and Preparation of Medicine: Aerosol (mg/mL)

compound prepared in Example 8: 2.5;
sorbitan monooleate: 3.38;
trichlorofluoromethane: 67.5;
dichlorodifluoromethane: 1086.0; and
dichlorotetrafluoroethane: 191.60;
suitable human subjects: those having a disease caused by abnormality of AXL protein kinase and/or VEGFR2 protein kinase.

Example 40: Composition and Preparation of Medicine: Aerosol (mg/mL)

compound prepared in Example 11: 2.5;
other components and contents thereof are same as in Example 39;
suitable human subjects: those having a disease caused by abnormality of AXL protein kinase and/or VEGFR2 protein kinase.

Example 41: Composition and Preparation of Medicine: Aerosol (mg/mL)

compound prepared in Example 4: 2.5;
soybean lecithin: 2.7;
trichlorofluoromethane: 67.5;
dichlorodifluoromethane: 1086.0; and
dichlorotetrafluoroethane: 191.60;

suitable human subjects: those having a disease caused by abnormality of AXL protein kinase and/or VEGFR2 protein kinase.

Example 42: Composition and Preparation of Medicine: Aerosol (mg/mL)

compound prepared in Example 13: 2.5;
other components and contents thereof are same as in Example 41;
suitable human subjects: those having a disease caused by abnormality of AXL protein kinase and/or VEGFR2 protein kinase.

Example 43: Composition and Preparation of Medicine: Ointment (/mL)

compound prepared in Example 1: 40 mg;
ethanol: 300 μl;
water: 300 μl;
1-dodecylazacycloheptanone: 50 μl; and
the remaining of 1 mL: propylene glycol;
suitable human subjects: those having a disease caused by abnormality of AXL protein kinase and/or VEGFR2 protein kinase.

Example 44: Composition and Preparation of Medicine: Ointment (/mL)

compound prepared in Example 7: 40 mg;
other components and contents thereof are same as in Example 43;
suitable human subjects: those having a disease caused by abnormality of AXL protein kinase and/or VEGFR2 protein kinase.

The technical solutions of the above-mentioned embodiments can be further combined or substituted. The embodiments described above are merely the preferred embodiment of the present application, but not intended to limit the concept or scope of the present application. Any change and improvement to the technical solutions of the present application, which are made by those skilled in the art without departing from the invention concept of the present application, shall fall within the protection scope of the present application.

What is claimed is:

1. A quinolyl-substituted carboxylic acid compound as shown in formula (I) or a pharmaceutically acceptable salt thereof,

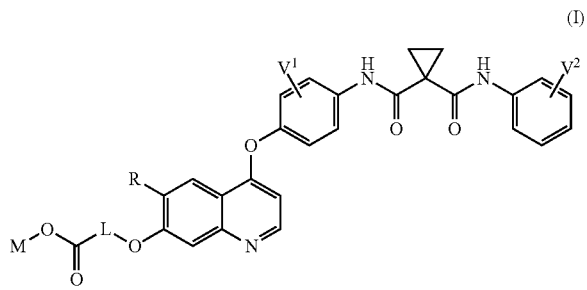

(I)

wherein $V^1$ and $V^2$ are each independently selected from hydrogen, deuterium, halogen, $C_{1-6}$ alkyl and $C_{1-6}$ alkoxy;

R is hydrogen, $C_{1-12}$ alkyl, or $C_{1-12}$ alkoxy, and hydrogen of R is selectively substituted by $G^1$;

L is $C_{1-12}$ alkylene, and hydrogen of L is selectively substituted by $G^2$;

M is selected from:
(a) hydrogen, deuterium, $C_{3-12}$ cycloalkyl, $C_{6-12}$ aryl, $C_{5-12}$ heteroaryl, and $C_{3-12}$ heteroalicyclic group, wherein hydrogen of M is selectively substituted by $G^3$; or
(b) monovalent, divalent, trivalent, and tetravalent metal ions, preferably monovalent and divalent metal ions, and more preferably lithium ion, sodium ion, potassium ion, rubidium ion, cesium ion, magnesium ion, calcium ion, strontium ion, and barium ion; or
(c) ammonium ion and an organic amine being protonated, the organic amine including, but not limited to, aliphatic amines substituted with $C_{1-12}$ alkyl, $C_{3-12}$ cycloalkyl, or $C_{3-12}$ heteroalicyclic group, the aliphatic amines being selectively substituted with one or more halogens or hydroxyls;

wherein $G^1$, $G^2$ and $G^3$ are each independently selected from hydrogen, deuterium, —CN, —CF$_3$, —CO$_2$H, halogen, $C_{1-12}$ alkyl, $C_{3-12}$ cycloalkyl, $C_{2-12}$ alkenyl, $C_{2-12}$ alkynyl, $C_{6-12}$ aryl, $C_{5-12}$ heteroaryl, $C_{3-12}$ heteroalicyclic group, $R^1O$—, $R^1R^2N$—, $R^1S(=O)_m$—, $R^1R^2NS(=O)_m$—, $R^3C(=O)$—, $R^1R^2NC(=O)$—, $R^1OC(=O)$—, $R^3C(=O)O$—, $R^1R^2NC(=O)O$—, $R^3C(=O)NR^1$—, $R^1R^2NC(=O)NR^4$—, $R^1OC(=O)NR^4$—, $R^1S(=O)_mNR^4$—, $R^1R^2NS(=O)_mNR^4$—, $R^1R^2NC(=NR^5)NR^4$—, $R^1R^2NC(=CHNO_2)NR^4$—, $R^1R^2NC(=N-CN)NR^4$—, $R^1R^2NC(=NR^5)$—, $R^1S(=O)(=NR^5)NR^4$—, and $R^1R^2NS(=O)(=NR^5)$—;

$R^1$, $R^2$, $R^3$, $R^4$ and $R^5$ are each independently selected from hydrogen, deuterium, $C_{1-12}$ alkyl, $C_{2-12}$ alkenyl, $C_{2-12}$ alkynyl, $C_{3-12}$ cycloalkyl, $C_{6-12}$ aryl, $C_{5-12}$ heteroaryl, and $C_{3-12}$ heteroalicyclic group; $R^1$ and $R^2$, when being bonded to a same nitrogen atom, form a $C_{3-12}$ heteroalicyclic ring together with the nitrogen atom, wherein the $C_{3-12}$ heteroalicyclic ring selectively contains a hetero atom of O, N, $S(=O)_m$; hydrogen of $R^1$, $R^2$, $R^3$, $R^4$ and $R^5$ is selectively substituted by halogen, CN, $C_{1-12}$ alkyl or $C_{3-12}$ cycloalkyl; and m is from 0 to 2.

2. The quinolyl-substituted carboxylic acid compound or the pharmaceutically acceptable salt thereof according to claim 1, wherein
$V^1$ and $V^2$ are each independently selected from hydrogen, deuterium, halogen, $C_{1-6}$ alkyl and $C_{1-6}$ alkoxy;
R is hydrogen, $C_{1-12}$ alkyl, or $C_{1-12}$ alkoxy;
L is $C_{1-12}$ alkylene;
M is selected from:
(a) hydrogen, and deuterium; or
(b) lithium ion, sodium ion, potassium ion, rubidium ion, cesium ion, magnesium ion, calcium ion, strontium ion, and barium ion; or
(c) ammonium ion and an organic amine being protonated, wherein the organic amine includes aliphatic amines substituted with $C_{1-12}$ alkyl, $C_{3-12}$ cycloalkyl, or $C_{3-12}$ heteroalicyclic group, the aliphatic amines being selectively substituted with one or more halogens or hydroxyls.

3. The quinolyl-substituted carboxylic acid compound or the pharmaceutically acceptable salt thereof according to claim 1, wherein $V^1$ and $V^2$ are each independently selected from hydrogen, deuterium, and halogen;
preferably, $V^1$ and $V^2$ are identical and are hydrogen, deuterium, or halogen, and $V^1$ and $V^2$ are located in the 2-position and the 4-position of the six-membered rings substituted with them, respectively.

4. The quinolyl-substituted carboxylic acid compound or the pharmaceutically acceptable salt thereof according to claim 1, wherein $V^1$ and $V^2$ are each independently selected from hydrogen, deuterium, and halogen, R is $C_{1-12}$ alkoxy, and L is $C_{1-12}$ alkylene.

5. The quinolyl-substituted carboxylic acid compound or the pharmaceutically acceptable salt thereof according to claim 1, wherein $V^1$ and $V^2$ are each independently selected from hydrogen and halogen; R is methoxy, ethoxy, n-propoxy, or isopropoxy; and L is $C_{1-6}$ alkylene.

6. The quinolyl-substituted carboxylic acid compound or the pharmaceutically acceptable salt thereof according to claim 1, wherein M is selected from hydrogen, and deuterium; or M is selected from lithium ion, sodium ion, potassium ion, magnesium ion, and calcium ion; or M is selected from ammonium ion, protonated methylamine, protonated ethylamine, protonated n-propylamine, protonated isopropylamine, protonated n-butylamine, protonated isobutylamine, protonated sec-butylamine, protonated tert-butylamine, protonated dimethylamine, protonated diethylamine, protonated di-n-propylamine, protonated diisopropylamine, protonated di-n-butylamine, protonated diisobutylamine, protonated di-sec-butylamine, protonated di-tert-butylamine, protonated trimethylamine, protonated triethylamine, protonated tri-n-propylamine, protonated tri-isopropylamine, protonated tri-n-butylamine, protonated triisobutylamine, protonated tri-sec-butylamine, protonated tri-tert-butylamine, protonated diisopropylethylamine, and protonated 2-amino-2-(hydroxymethyl)propane-1,3-diol.

7. The quinolyl-substituted carboxylic acid compound or the pharmaceutically acceptable salt thereof according to claim 1, wherein the compound is selected from:

2-[[4-[2-fluoro-4-[[1-[(3-chlorophenyl)carbamoyl]cyclopropanecarbonyl]amino]phenoxy]-6-methoxy-7-quinolyl]oxy]acetic acid;

lithium 2-[[4-[2-fluoro-4-[[1-[(3-chlorophenyl)carbamoyl]cyclopropanecarbonyl]amino]phenoxy]-6-methoxy-7-quinolyl]oxy]acetate;

sodium 2-[[4-[2-fluoro-4-[[1-[(3-chlorophenyl)carbamoyl]cyclopropanecarbonyl]amino]phenoxy]-6-methoxy-7-quinolyl]oxy]acetate;

potassium 2-[[4-[2-fluoro-4-[[1-[(3-chlorophenyl)carbamoyl]cyclopropanecarbonyl]amino]phenoxy]-6-methoxy-7-quinolyl]oxy]acetate;

magnesium 2-[[4-[2-fluoro-4-[[1-[(3-chlorophenyl)carbamoyl]cyclopropanecarbonyl]amino]phenoxy]-6-methoxy-7-quinolyl]oxy]acetate;

calcium 2-[[4-[2-fluoro-4-[[1-[(3-chlorophenyl)carbamoyl]cyclopropanecarbonyl]amino]phenoxy]-6-methoxy-7-quinolyl]oxy]acetate;

ammonium 2-[[4-[2-fluoro-4-[[1-[(3-chlorophenyl)carbamoyl]cyclopropanecarbonyl]amino]phenoxy]-6-methoxy-7-quinolyl]oxy]acetate;

triethylammonium 2-[[4-[2-fluoro-4-[[1-[(3-chlorophenyl)carbamoyl]cyclopropane carbonyl]amino]phenoxy]-6-methoxy-7-quinolyl]oxy]acetate;

1,3-dihydroxy-2-(hydroxymethyl)propan-2-ammonium 2-[[4-[2-fluoro-4-[[1-[(3-chlorophenyl)carbamoyl]cyclopropanecarbonyl]amino]phenoxy]-6-methoxy-7-quinolyl]oxy]acetate;

3-[[4-[2-fluoro-4-[[1-[(3-chlorophenyl)carbamoyl]cyclopropanecarbonyl]amino]phenoxy]-6-methoxy-7-quinolyl]oxy]propionic acid;

lithium 3-[[4-[2-fluoro-4-[[1-[(3-chlorophenyl)carbamoyl]cyclopropanecarbonyl]amino]phenoxy]-6-methoxy-7-quinolyl]oxy]propionate;

sodium 3-[[4-[2-fluoro-4-[[1-[(3-chlorophenyl)carbamoyl]cyclopropanecarbonyl]amino]phenoxy]-6-methoxy-7-quinolyl]oxy]propionate;

potassium 3-[[4-[2-fluoro-4-[[1-[(3-chlorophenyl)carbamoyl]cyclopropanecarbonyl]amino]phenoxy]-6-methoxy-7-quinolyl]oxy]propionate;

magnesium 3-[[4-[2-fluoro-4-[[1-[(3-chlorophenyl)carbamoyl]cyclopropanecarbonyl]amino]phenoxy]-6-methoxy-7-quinolyl]oxy]propionate;

calcium 3-[[4-[2-fluoro-4-[[1-[(3-chlorophenyl)carbamoyl]cyclopropanecarbonyl]amino]phenoxy]-6-methoxy-7-quinolyl]oxy]propionate;

ammonium 3-[[4-[2-fluoro-4-[[1-[(3-chlorophenyl)carbamoyl]cyclopropanecarbonyl]amino]phenoxy]-6-methoxy-7-quinolyl]oxy]propionate;

triethylammonium 3-[[4-[2-fluoro-4-[[1-[(3-chlorophenyl)carbamoyl]cyclopropane carbonyl]amino]phenoxy]-6-methoxy-7-quinolyl]oxy]propionate;

1,3-dihydroxy-2-(hydroxymethyl)propan-2-ammonium 3-[[4-[2-fluoro-4-[[1-[(3-chlorophenyl)carbamoyl]cyclopropanecarbonyl]amino]phenoxy]-6-methoxy-7-quinolyl]oxy]propionate;

4-[[4-[2-fluoro-4-[[1-[(3-chlorophenyl)carbamoyl]cyclopropanecarbonyl]amino]phenoxy]-6-methoxy-7-quinolyl]oxy]butyric acid;

lithium 4-[[4-[2-fluoro-4-[[1-[(3-chlorophenyl)carbamoyl]cyclopropanecarbonyl]amino]phenoxy]-6-methoxy-7-quinolyl]oxy]butyrate;

sodium 4-[[4-[2-fluoro-4-[[1-[(3-chlorophenyl)carbamoyl]cyclopropanecarbonyl]amino]phenoxy]-6-methoxy-7-quinolyl]oxy]butyrate;

potassium 4-[[4-[2-fluoro-4-[[1-[(3-chlorophenyl)carbamoyl]cyclopropanecarbonyl]amino]phenoxy]-6-methoxy-7-quinolyl]oxy]butyrate;

magnesium 4-[[4-[2-fluoro-4-[[1-[(3-chlorophenyl)carbamoyl]cyclopropanecarbonyl]amino]phenoxy]-6-methoxy-7-quinolyl]oxy]butyrate;

calcium 4-[[4-[2-fluoro-4-[[1-[(3-chlorophenyl)carbamoyl]cyclopropanecarbonyl]amino]phenoxy]-6-methoxy-7-quinolyl]oxy]butyrate;

ammonium 4-[[4-[2-fluoro-4-[[1-[(3-chlorophenyl)carbamoyl]cyclopropanecarbonyl]amino]phenoxy]-6-methoxy-7-quinolyl]oxy]butyrate;

triethylammonium 4-[[4-[2-fluoro-4-[[1-[(3-chlorophenyl)carbamoyl]cyclopropane carbonyl]amino]phenoxy]-6-methoxy-7-quinolyl]oxy]butyrate;

1,3-dihydroxy-2-(hydroxymethyl)propan-2-ammonium 4-[[4-[2-fluoro-4-[[1-[(3-chlorophenyl)carbamoyl]cyclopropanecarbonyl]amino]phenoxy]-6-methoxy-7-quinolyl]oxy]butyrate;

5-[[4-[2-fluoro-4-[[1-[(3-chlorophenyl)carbamoyl]cyclopropanecarbonyl]amino]phenoxy]-6-methoxy-7-quinolyl]oxy]valeric acid;

lithium 5-[[4-[2-fluoro-4-[[1-[(3-chlorophenyl)carbamoyl]cyclopropanecarbonyl]amino]phenoxy]-6-methoxy-7-quinolyl]oxy]valerate;

sodium 5-[[4-[2-fluoro-4-[[1-[(3-chlorophenyl)carbamoyl]cyclopropanecarbonyl]amino]phenoxy]-6-methoxy-7-quinolyl]oxy]valerate;

potassium 5-[[4-[2-fluoro-4-[[1-[(3-chlorophenyl)carbamoyl]cyclopropanecarbonyl]amino]phenoxy]-6-methoxy-7-quinolyl]oxy]valerate;

magnesium 5-[[4-[2-fluoro-4-[[1-[(3-chlorophenyl)carbamoyl]cyclopropanecarbonyl]amino]phenoxy]-6-methoxy-7-quinolyl]oxy]valerate;

calcium 5-[[4-[2-fluoro-4-[[1-[(3-chlorophenyl)carbamoyl]cyclopropanecarbonyl]amino]phenoxy]-6-methoxy-7-quinolyl]oxy]valerate;

ammonium 5-[[4-[2-fluoro-4-[[1-[(3-chlorophenyl)carbamoyl]cyclopropanecarbonyl]amino]phenoxy]-6-methoxy-7-quinolyl]oxy]valerate;

triethylammonium 5-[[4-[2-fluoro-4-[[1-[(3-chlorophenyl)carbamoyl]cyclopropane carbonyl]amino]phenoxy]-6-methoxy-7-quinolyl]oxy]valerate;

1,3-dihydroxy-2-(hydroxymethyl)propan-2-ammonium 5-[[4-[2-fluoro-4-[[1-[(3-chlorophenyl)carbamoyl]cyclopropanecarbonyl]amino]phenoxy]-6-methoxy-7-quinolyl]oxy]valerate;

6-[[4-[2-fluoro-4-[[1-[(3-chlorophenyl)carbamoyl]cyclopropanecarbonyl]amino]phenoxy]-6-methoxy-7-quinolyl]oxy]caproic acid;

lithium 6-[[4-[2-fluoro-4-[[1-[(3-chlorophenyl)carbamoyl]cyclopropanecarbonyl]amino]phenoxy]-6-methoxy-7-quinolyl]oxy]caproate;

sodium 6-[[4-[2-fluoro-4-[[1-[(3-chlorophenyl)carbamoyl]cyclopropanecarbonyl]amino]phenoxy]-6-methoxy-7-quinolyl]oxy]caproate;

potassium 6-[[4-[2-fluoro-4-[[1-[(3-chlorophenyl)carbamoyl]cyclopropanecarbonyl]amino]phenoxy]-6-methoxy-7-quinolyl]oxy]caproate;

magnesium 6-[[4-[2-fluoro-4-[[1-[(3-chlorophenyl)carbamoyl]cyclopropanecarbonyl]amino]phenoxy]-6-methoxy-7-quinolyl]oxy]caproate;

calcium 6-[[4-[2-fluoro-4-[[1-[(3-chlorophenyl)carbamoyl]cyclopropanecarbonyl]amino]phenoxy]-6-methoxy-7-quinolyl]oxy]caproate;

ammonium 6-[[4-[2-fluoro-4-[[1-[(3-chlorophenyl)carbamoyl]cyclopropanecarbonyl]amino]phenoxy]-6-methoxy-7-quinolyl]oxy]caproate;

triethylammonium 6-[[4-[2-fluoro-4-[[1-[(3-chlorophenyl)carbamoyl]cyclopropane carbonyl]amino]phenoxy]-6-methoxy-7-quinolyl]oxy]caproate;

1,3-dihydroxy-2-(hydroxymethyl)propan-2-ammonium 6-[[4-[2-fluoro-4-[[1-[(3-chlorophenyl)carbamoyl]cyclopropanecarbonyl]amino]phenoxy]-6-methoxy-7-quinolyl]oxy]caproate;

7-[[4-[2-fluoro-4-[[1-[(3-chlorophenyl)carbamoyl]cyclopropanecarbonyl]amino]phenoxy]-6-methoxy-7-quinolyl]oxy]heptanoic acid;

lithium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

sodium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

potassium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

magnesium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

calcium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

ammonium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

triethylammonium 7-[[4-[2-fluoro-4-[[1-[(3-chlorophenyl)carbamoyl]cyclopropane carbonyl]amino]phenoxy]-6-methoxy-7-quinolyl]oxy]heptanoate;

1,3-dihydroxy-2-(hydroxymethyl)propan-2-ammonium 7-[[4-[2-fluoro-4-[[1-[(3-chlorophenyl)carbamoyl]cyclopropanecarbonyl]amino]phenoxy]-6-methoxy-7-quinolyl]oxy]heptanoate;

2-[[4-[2-fluoro-4-[[1-[(4-fluorophenyl)carbamoyl]cyclopropanecarbonyl]amino]phenoxy]-6-methoxy-7-quinolyl]oxy]acetic acid;

lithium 2-[[4-[2-fluoro-4-[[1-[(4-fluorophenyl)carbamoyl]cyclopropanecarbonyl]amino]phenoxy]-6-methoxy-7-quinolyl]oxy]acetate;

sodium 2-[[4-[2-fluoro-4-[[1-[(4-fluorophenyl)carbamoyl]cyclopropanecarbonyl]amino]phenoxy]-6-methoxy-7-quinolyl]oxy]acetate;

potassium 2-[[4-[2-fluoro-4-[[1-[(4-fluorophenyl)carbamoyl]cyclopropanecarbonyl]amino]phenoxy]-6-methoxy-7-quinolyl]oxy]acetate;

magnesium 2-[[4-[2-fluoro-4-[[1-[(4-fluorophenyl)carbamoyl]cyclopropanecarbonyl]amino]phenoxy]-6-methoxy-7-quinolyl]oxy]acetate;

calcium 2-[[4-[2-fluoro-4-[[1-[(4-fluorophenyl)carbamoyl]cyclopropanecarbonyl]amino]phenoxy]-6-methoxy-7-quinolyl]oxy]acetate;

ammonium 2-[[4-[2-fluoro-4-[[1-[(4-fluorophenyl)carbamoyl]cyclopropanecarbonyl]amino]phenoxy]-6-methoxy-7-quinolyl]oxy]acetate;

triethylammonium 2-[[4-[2-fluoro-4-[[1-[(4-fluorophenyl)carbamoyl]cyclopropane carbonyl]amino]phenoxy]-6-methoxy-7-quinolyl]oxy]acetate;

1,3-dihydroxy-2-(hydroxymethyl)propan-2-ammonium 2-[[4-[2-fluoro-4-[[1-[(4-fluorophenyl)carbamoyl]cyclopropanecarbonyl]amino]phenoxy]-6-methoxy-7-quinolyl]oxy]acetate;

3-[[4-[2-fluoro-4-[[1-[(4-fluorophenyl)carbamoyl]cyclopropanecarbonyl]amino]phenoxy]-6-methoxy-7-quinolyl]oxy]propionic acid;

lithium 3-[[4-[2-fluoro-4-[[1-[(4-fluorophenyl)carbamoyl]cyclopropanecarbonyl]amino]phenoxy]-6-methoxy-7-quinolyl]oxy]propionate;

sodium 3-[[4-[2-fluoro-4-[[1-[(4-fluorophenyl)carbamoyl]cyclopropanecarbonyl]amino]phenoxy]-6-methoxy-7-quinolyl]oxy]propionate;

potassium 3-[[4-[2-fluoro-4-[[1-[(4-fluorophenyl)carbamoyl]cyclopropanecarbonyl]amino]phenoxy]-6-methoxy-7-quinolyl]oxy]propionate;

magnesium 3-[[4-[2-fluoro-4-[[1-[(4-fluorophenyl)carbamoyl]cyclopropanecarbonyl]amino]phenoxy]-6-methoxy-7-quinolyl]oxy]propionate;

calcium 3-[[4-[2-fluoro-4-[[1-[(4-fluorophenyl)carbamoyl]cyclopropanecarbonyl]amino]phenoxy]-6-methoxy-7-quinolyl]oxy]propionate;

ammonium 3-[[4-[2-fluoro-4-[[1-[(4-fluorophenyl)carbamoyl]cyclopropanecarbonyl]amino]phenoxy]-6-methoxy-7-quinolyl]oxy]propionate;

triethylammonium 3-[[4-[2-fluoro-4-[[1-[(4-fluorophenyl)carbamoyl]cyclopropane carbonyl]amino]phenoxy]-6-methoxy-7-quinolyl]oxy]propionate;

1,3-dihydroxy-2-(hydroxymethyl)propan-2-ammonium 3-[[4-[2-fluoro-4-[[1-[(4-fluorophenyl)carbamoyl]cyclopropanecarbonyl]amino]phenoxy]-6-methoxy-7-quinolyl]oxy]propionate;

4-[[4-[2-fluoro-4-[[1-[(4-fluorophenyl)carbamoyl]cyclopropanecarbonyl]amino]phenoxy]-6-methoxy-7-quinolyl]oxy]butyric acid;

lithium 4-[[4-[2-fluoro-4-[[1-[(4-fluorophenyl)carbamoyl]cyclopropanecarbonyl]amino]phenoxy]-6-methoxy-7-quinolyl]oxy]butyrate;

sodium 4-[[4-[2-fluoro-4-[[1-[(4-fluorophenyl)carbamoyl]cyclopropanecarbonyl]amino]phenoxy]-6-methoxy-7-quinolyl]oxy]butyrate;

potassium 4-[[4-[2-fluoro-4-[[1-[(4-fluorophenyl)carbamoyl]cyclopropanecarbonyl]amino]phenoxy]-6-methoxy-7-quinolyl]oxy]butyrate;

magnesium 4-[[4-[2-fluoro-4-[[1-[(4-fluorophenyl)carbamoyl]cyclopropanecarbonyl]amino]phenoxy]-6-methoxy-7-quinolyl]oxy]butyrate;

calcium 4-[[4-[2-fluoro-4-[[1-[(4-fluorophenyl)carbamoyl]cyclopropanecarbonyl]amino]phenoxy]-6-methoxy-7-quinolyl]oxy]butyrate;

ammonium 4-[[4-[2-fluoro-4-[[1-[(4-fluorophenyl)carbamoyl]cyclopropanecarbonyl]amino]phenoxy]-6-methoxy-7-quinolyl]oxy]butyrate;

triethylammonium 4-[[4-[2-fluoro-4-[[1-[(4-fluorophenyl)carbamoyl]cyclopropane carbonyl]amino]phenoxy]-6-methoxy-7-quinolyl]oxy]butyrate;

1,3-dihydroxy-2-(hydroxymethyl)propan-2-ammonium 4-[[4-[2-fluoro-4-[[1-[(4-fluorophenyl)carbamoyl]cyclopropanecarbonyl]amino]phenoxy]-6-methoxy-7-quinolyl]oxy]butyrate;

5-[[4-[2-fluoro-4-[[1-[(4-fluorophenyl)carbamoyl]cyclopropanecarbonyl]amino]phenoxy]-6-methoxy-7-quinolyl]oxy]valeric acid;

lithium 5-[[4-[2-fluoro-4-[[1-[(4-fluorophenyl)carbamoyl]cyclopropanecarbonyl]amino]phenoxy]-6-methoxy-7-quinolyl]oxy]valerate;

sodium 5-[[4-[2-fluoro-4-[[1-[(4-fluorophenyl)carbamoyl]cyclopropanecarbonyl]amino]phenoxy]-6-methoxy-7-quinolyl]oxy]valerate;

potassium 5-[[4-[2-fluoro-4-[[1-[(4-fluorophenyl)carbamoyl]cyclopropanecarbonyl]amino]phenoxy]-6-methoxy-7-quinolyl]oxy]valerate;

magnesium 5-[[4-[2-fluoro-4-[[1-[(4-fluorophenyl)carbamoyl]cyclopropanecarbonyl]amino]phenoxy]-6-methoxy-7-quinolyl]oxy]valerate;

calcium 5-[[4-[2-fluoro-4-[[1-[(4-fluorophenyl)carbamoyl]cyclopropanecarbonyl]amino]phenoxy]-6-methoxy-7-quinolyl]oxy]valerate;

ammonium 5-[[4-[2-fluoro-4-[[1-[(4-fluorophenyl)carbamoyl]cyclopropanecarbonyl]amino]phenoxy]-6-methoxy-7-quinolyl]oxy]valerate;

triethylammonium 5-[[4-[2-fluoro-4-[[1-[(4-fluorophenyl)carbamoyl]cyclopropane carbonyl]amino]phenoxy]-6-methoxy-7-quinolyl]oxy]valerate;

1,3-dihydroxy-2-(hydroxymethyl)propan-2-ammonium 5-[[4-[2-fluoro-4-[[1-[(4-fluorophenyl)carbamoyl]cyclopropanecarbonyl]amino]phenoxy]-6-methoxy-7-quinolyl]oxy]valerate;

6-[[4-[2-fluoro-4-[[1-[(4-fluorophenyl)carbamoyl]cyclopropanecarbonyl]amino]phenoxy]-6-methoxy-7-quinolyl]oxy]caproic acid;

lithium 6-[[4-[2-fluoro-4-[[1-[(4-fluorophenyl)carbamoyl]cyclopropanecarbonyl]amino]phenoxy]-6-methoxy-7-quinolyl]oxy]caproate;

sodium 6-[[4-[2-fluoro-4-[[1-[(4-fluorophenyl)carbamoyl]cyclopropanecarbonyl]amino]phenoxy]-6-methoxy-7-quinolyl]oxy]caproate;

potassium 6-[[4-[2-fluoro-4-[[1-[(4-fluorophenyl)carbamoyl]cyclopropanecarbonyl]amino]phenoxy]-6-methoxy-7-quinolyl]oxy]caproate;

magnesium 6-[[4-[2-fluoro-4-[[1-[(4-fluorophenyl)carbamoyl]cyclopropanecarbonyl]amino]phenoxy]-6-methoxy-7-quinolyl]oxy]caproate;

calcium 6-[[4-[2-fluoro-4-[[1-[(4-fluorophenyl)carbamoyl]cyclopropanecarbonyl]amino]phenoxy]-6-methoxy-7-quinolyl]oxy]caproate;

ammonium 6-[[4-[2-fluoro-4-[[1-[(4-fluorophenyl)carbamoyl]cyclopropanecarbonyl]amino]phenoxy]-6-methoxy-7-quinolyl]oxy]caproate;

triethylammonium 6-[[4-[2-fluoro-4-[[1-[(4-fluorophenyl)carbamoyl]cyclopropane carbonyl]amino]phenoxy]-6-methoxy-7-quinolyl]oxy]caproate;

1,3-dihydroxy-2-(hydroxymethyl)propan-2-ammonium 6-[[4-[2-fluoro-4-[[1-[(4-fluorophenyl)carbamoyl]cyclopropanecarbonyl]amino]phenoxy]-6-methoxy-7-quinolyl]oxy]caproate;

7-[[4-[2-fluoro-4-[[1-[(4-fluorophenyl)carbamoyl]cyclopropanecarbonyl]amino]phenoxy]-6-methoxy-7-quinolyl]oxy]heptanoic acid;

lithium 7-[[4-[2-fluoro-4-[[1-[(4-fluorophenyl)carbamoyl]cyclopropanecarbonyl]amino]phenoxy]-6-methoxy-7-quinolyl]oxy]heptanoate;

sodium 7-[[4-[2-fluoro-4-[[1-[(4-fluorophenyl)carbamoyl]cyclopropanecarbonyl]amino]phenoxy]-6-methoxy-7-quinolyl]oxy]heptanoate;

potassium 7-[[4-[2-fluoro-4-[[1-[(4-fluorophenyl)carbamoyl]cyclopropanecarbonyl]amino]phenoxy]-6-methoxy-7-quinolyl]oxy]heptanoate;

magnesium 7-[[4-[2-fluoro-4-[[1-[(4-fluorophenyl)carbamoyl]cyclopropanecarbonyl]amino]phenoxy]-6-methoxy-7-quinolyl]oxy]heptanoate;

calcium 7-[[4-[2-fluoro-4-[[1-[(4-fluorophenyl)carbamoyl]cyclopropanecarbonyl]amino]phenoxy]-6-methoxy-7-quinolyl]oxy]heptanoate;

ammonium 7-[[4-[2-fluoro-4-[[1-[(4-fluorophenyl)carbamoyl]cyclopropanecarbonyl]amino]phenoxy]-6-methoxy-7-quinolyl]oxy]heptanoate;

triethylammonium 7-[[4-[2-fluoro-4-[[1-[(4-fluorophenyl)carbamoyl]cyclopropane carbonyl]amino]phenoxy]-6-methoxy-7-quinolyl]oxy]heptanoate;

1,3-dihydroxy-2-(hydroxymethyl)propan-2-ammonium 7-[[4-[2-fluoro-4-[[1-[(4-fluorophenyl)carbamoyl]cyclopropanecarbonyl]amino]phenoxy]-6-methoxy-7-quinolyl]oxy]heptanoate;

2-[[4-[2-chloro-[[1-[(4-fluorophenyl)carbamoyl]cyclopropanecarbonyl]amino]phenoxy]-6-methoxy-7-quinolyl]oxy]acetic acid;

lithium 2-[[4-[2-chloro-[[1-[(4-fluorophenyl)carbamoyl]cyclopropanecarbonyl]amino]phenoxy]-6-methoxy-7-quinolyl]oxy]acetate;

sodium 2-[[4-[2-chloro-[[1-[(4-fluorophenyl)carbamoyl]cyclopropanecarbonyl]amino]phenoxy]-6-methoxy-7-quinolyl]oxy]acetate;

potassium 2-[[4-[2-chloro-[[1-[(4-fluorophenyl)carbamoyl]cyclopropanecarbonyl]amino]phenoxy]-6-methoxy-7-quinolyl]oxy]acetate;

magnesium 2-[[4-[2-chloro-[[1-[(4-fluorophenyl)carbamoyl]cyclopropanecarbonyl]amino]phenoxy]-6-methoxy-7-quinolyl]oxy]acetate;

calcium 2-[[4-[2-chloro-[[1-[(4-fluorophenyl)carbamoyl]cyclopropanecarbonyl]amino]phenoxy]-6-methoxy-7-quinolyl]oxy]acetate;

ammonium 2-[[4-[2-chloro-[[1-[(4-fluorophenyl)carbamoyl]cyclopropanecarbonyl]amino]phenoxy]-6-methoxy-7-quinolyl]oxy]acetate;
triethylammonium 2-[[4-[2-chloro-[[1-[(4-fluorophenyl)carbamoyl]cyclopropane carbonyl]amino]phenoxy]-6-methoxy-7-quinolyl]oxy]acetate;
1,3-dihydroxy-2-(hydroxymethyl)propan-2-ammonium 2-[[4-[2-chloro-[[1-[(4-fluorophenyl)carbamoyl]cyclopropanecarbonyl]amino]phenoxy]-6-methoxy-7-quinolyl]oxy]acetate;
3-[[4-[2-chloro-[[1-[(4-fluorophenyl)carbamoyl]cyclopropanecarbonyl]amino]phenoxy]-6-methoxy-7-quinolyl]oxy]propionic acid;
lithium 3-[[4-[2-chloro-[[1-[(4-fluorophenyl)carbamoyl]cyclopropanecarbonyl]amino]phenoxy]-6-methoxy-7-quinolyl]oxy]propionate;
sodium 3-[[4-[2-chloro-[[1-[(4-fluorophenyl)carbamoyl]cyclopropanecarbonyl]amino]phenoxy]-6-methoxy-7-quinolyl]oxy]propionate;
potassium 3-[[4-[2-chloro-[[1-[(4-fluorophenyl)carbamoyl]cyclopropanecarbonyl]amino]phenoxy]-6-methoxy-7-quinolyl]oxy]propionate;
magnesium 3-[[4-[2-chloro-[[1-[(4-fluorophenyl)carbamoyl]cyclopropanecarbonyl]amino]phenoxy]-6-methoxy-7-quinolyl]oxy]propionate;
calcium 3-[[4-[2-chloro-[[1-[(4-fluorophenyl)carbamoyl]cyclopropanecarbonyl]amino]phenoxy]-6-methoxy-7-quinolyl]oxy]propionate;
ammonium 3-[[4-[2-chloro-[[1-[(4-fluorophenyl)carbamoyl]cyclopropanecarbonyl]amino]phenoxy]-6-methoxy-7-quinolyl]oxy]propionate;
triethylammonium 3-[[4-[2-chloro-[[1-[(4-fluorophenyl)carbamoyl]cyclopropane carbonyl]amino]phenoxy]-6-methoxy-7-quinolyl]oxy]propionate;
1,3-dihydroxy-2-(hydroxymethyl)propan-2-ammonium 3-[[4-[2-chloro-[[1-[(4-fluorophenyl)carbamoyl]cyclopropanecarbonyl]amino]phenoxy]-6-methoxy-7-quinolyl]oxy]propionate;
4-[[4-[2-chloro-[[1-[(4-fluorophenyl)carbamoyl]cyclopropanecarbonyl]amino]phenoxy]-6-methoxy-7-quinolyl]oxy]butyric acid;
lithium 4-[[4-[2-chloro-[[1-[(4-fluorophenyl)carbamoyl]cyclopropanecarbonyl]amino]phenoxy]-6-methoxy-7-quinolyl]oxy]butyrate;
sodium 4-[[4-[2-chloro-[[1-[(4-fluorophenyl)carbamoyl]cyclopropanecarbonyl]amino]phenoxy]-6-methoxy-7-quinolyl]oxy]butyrate;
potassium 4-[[4-[2-chloro-[[1-[(4-fluorophenyl)carbamoyl]cyclopropanecarbonyl]amino]phenoxy]-6-methoxy-7-quinolyl]oxy]butyrate;
magnesium 4-[[4-[2-chloro-[[1-[(4-fluorophenyl)carbamoyl]cyclopropanecarbonyl]amino]phenoxy]-6-methoxy-7-quinolyl]oxy]butyrate;
calcium 4-[[4-[2-chloro-[[1-[(4-fluorophenyl)carbamoyl]cyclopropanecarbonyl]amino]phenoxy]-6-methoxy-7-quinolyl]oxy]butyrate;
ammonium 4-[[4-[2-chloro-[[1-[(4-fluorophenyl)carbamoyl]cyclopropanecarbonyl]amino]phenoxy]-6-methoxy-7-quinolyl]oxy]butyrate;
triethylammonium 4-[[4-[2-chloro-[[1-[(4-fluorophenyl)carbamoyl]cyclopropane carbonyl]amino]phenoxy]-6-methoxy-7-quinolyl]oxy]butyrate;
1,3-dihydroxy-2-(hydroxymethyl)propan-2-ammonium 4-[[4-[2-chloro-[[1-[(4-fluorophenyl)carbamoyl]cyclopropanecarbonyl]amino]phenoxy]-6-methoxy-7-quinolyl]oxy]butyrate;
5-[[4-[2-chloro-[[1-[(4-fluorophenyl)carbamoyl]cyclopropanecarbonyl]amino]phenoxy]-6-methoxy-7-quinolyl]oxy]valeric acid;
lithium 5-[[4-[2-chloro-[[1-[(4-fluorophenyl)carbamoyl]cyclopropanecarbonyl]amino]phenoxy]-6-methoxy-7-quinolyl]oxy]valerate;
sodium 5-[[4-[2-chloro-[[1-[(4-fluorophenyl)carbamoyl]cyclopropanecarbonyl]amino]phenoxy]-6-methoxy-7-quinolyl]oxy]valerate;
potassium 5-[[4-[2-chloro-[[1-[(4-fluorophenyl)carbamoyl]cyclopropanecarbonyl]amino]phenoxy]-6-methoxy-7-quinolyl]oxy]valerate;
magnesium 5-[[4-[2-chloro-[[1-[(4-fluorophenyl)carbamoyl]cyclopropanecarbonyl]amino]phenoxy]-6-methoxy-7-quinolyl]oxy]valerate;
calcium 5-[[4-[2-chloro-[[1-[(4-fluorophenyl)carbamoyl]cyclopropanecarbonyl]amino]phenoxy]-6-methoxy-7-quinolyl]oxy]valerate;
ammonium 5-[[4-[2-chloro-[[1-[(4-fluorophenyl)carbamoyl]cyclopropanecarbonyl]amino]phenoxy]-6-methoxy-7-quinolyl]oxy]valerate;
triethylammonium 5-[[4-[2-chloro-[[1-[(4-fluorophenyl)carbamoyl]cyclopropane carbonyl]amino]phenoxy]-6-methoxy-7-quinolyl]oxy]valerate;
1,3-dihydroxy-2-(hydroxymethyl)propan-2-ammonium 5-[[4-[2-chloro-[[1-[(4-fluorophenyl)carbamoyl]cyclopropanecarbonyl]amino]phenoxy]-6-methoxy-7-quinolyl]oxy]valerate;
6-[[4-[2-chloro-[[1-[(4-fluorophenyl)carbamoyl]cyclopropanecarbonyl]amino]phenoxy]-6-methoxy-7-quinolyl]oxy]caproic acid;
lithium 6-[[4-[2-chloro-[[1-[(4-fluorophenyl)carbamoyl]cyclopropanecarbonyl]amino]phenoxy]-6-methoxy-7-quinolyl]oxy]caproate;
sodium 6-[[4-[2-chloro-[[1-[(4-fluorophenyl)carbamoyl]cyclopropanecarbonyl]amino]phenoxy]-6-methoxy-7-quinolyl]oxy]caproate;
potassium 6-[[4-[2-chloro-[[1-[(4-fluorophenyl)carbamoyl]cyclopropanecarbonyl]amino]phenoxy]-6-methoxy-7-quinolyl]oxy]caproate;
magnesium 6-[[4-[2-chloro-[[1-[(4-fluorophenyl)carbamoyl]cyclopropanecarbonyl]amino]phenoxy]-6-methoxy-7-quinolyl]oxy]caproate;
calcium 6-[[4-[2-chloro-[[1-[(4-fluorophenyl)carbamoyl]cyclopropanecarbonyl]amino]phenoxy]-6-methoxy-7-quinolyl]oxy]caproate;
ammonium 6-[[4-[2-chloro-[[1-[(4-fluorophenyl)carbamoyl]cyclopropanecarbonyl]amino]phenoxy]-6-methoxy-7-quinolyl]oxy]caproate;
triethylammonium 6-[[4-[2-chloro-[[1-[(4-fluorophenyl)carbamoyl]cyclopropane carbonyl]amino]phenoxy]-6-methoxy-7-quinolyl]oxy]caproate;
1,3-dihydroxy-2-(hydroxymethyl)propan-2-ammonium 6-[[4-[2-chloro-[[1-[(4-fluorophenyl)carbamoyl]cyclopropanecarbonyl]amino]phenoxy]-6-methoxy-7-quinolyl]oxy]caproate;
7-[[4-[2-chloro-[[1-[(4-fluorophenyl)carbamoyl]cyclopropanecarbonyl]amino]phenoxy]-6-methoxy-7-quinolyl]oxy]heptanoic acid;
lithium 7-[[4-[2-chloro-[[1-[(4-fluorophenyl)carbamoyl]cyclopropanecarbonyl]amino]phenoxy]-6-methoxy-7-quinolyl]oxy]heptanoate;
sodium 7-[[4-[2-chloro-[[1-[(4-fluorophenyl)carbamoyl]cyclopropanecarbonyl]amino]phenoxy]-6-methoxy-7-quinolyl]oxy]heptanoate;

potassium 7-[[4-[2-chloro-[[1-[(4-fluorophenyl)carbamoyl]cyclopropanecarbonyl]amino]phenoxy]-6-methoxy-7-quinolyl]oxy]heptanoate;

magnesium 7-[[4-[2-chloro-[[1-[(4-fluorophenyl)carbamoyl]cyclopropanecarbonyl]amino]phenoxy]-6-methoxy-7-quinolyl]oxy]heptanoate;

calcium 7-[[4-[2-chloro-[[1-[(4-fluorophenyl)carbamoyl]cyclopropanecarbonyl]amino]phenoxy]-6-methoxy-7-quinolyl]oxy]heptanoate;

ammonium 7-[[4-[2-chloro-[[1-[(4-fluorophenyl)carbamoyl]cyclopropanecarbonyl]amino]phenoxy]-6-methoxy-7-quinolyl]oxy]heptanoate;

triethylammonium 7-[[4-[2-chloro-[[1-[(4-fluorophenyl)carbamoyl]cyclopropane carbonyl]amino]phenoxy]-6-methoxy-7-quinolyl]oxy]heptanoate;

1,3-dihydroxy-2-(hydroxymethyl)propan-2-ammonium 7-[[4-[2-chloro-[[1-[(4-fluorophenyl)carbamoyl]cyclopropanecarbonyl]amino]phenoxy]-6-methoxy-7-quinolyl]oxy]heptanoate;

2-[[4-[2-fluoro-4-[[1-[(4-fluorophenyl)carbamoyl]cyclopropanecarbonyl]amino]phenoxy]-6-ethoxy-7-quinolyl]oxy]acetic acid;

lithium 2-[[4-[2-fluoro-4-[[1-[(4-fluorophenyl)carbamoyl]cyclopropanecarbonyl]amino]phenoxy]-6-ethoxy-7-quinolyl]oxy]acetate;

sodium 2-[[4-[2-fluoro-4-[[1-[(4-fluorophenyl)carbamoyl]cyclopropanecarbonyl]amino]phenoxy]-6-ethoxy-7-quinolyl]oxy]acetate;

potassium 2-[[4-[2-fluoro-4-[[1-[(4-fluorophenyl)carbamoyl]cyclopropanecarbonyl]amino]phenoxy]-6-ethoxy-7-quinolyl]oxy]acetate;

magnesium 2-[[4-[2-fluoro-4-[[1-[(4-fluorophenyl)carbamoyl]cyclopropanecarbonyl]amino]phenoxy]-6-ethoxy-7-quinolyl]oxy]acetate;

calcium 2-[[4-[2-fluoro-4-[[1-[(4-fluorophenyl)carbamoyl]cyclopropanecarbonyl]amino]phenoxy]-6-ethoxy-7-quinolyl]oxy]acetate;

ammonium 2-[[4-[2-fluoro-4-[[1-[(4-fluorophenyl)carbamoyl]cyclopropanecarbonyl]amino]phenoxy]-6-ethoxy-7-quinolyl]oxy]acetate;

triethylammonium 2-[[4-[2-fluoro-4-[[1-[(4-fluorophenyl)carbamoyl]cyclopropane carbonyl]amino]phenoxy]-6-ethoxy-7-quinolyl]oxy]acetate;

1,3-dihydroxy-2-(hydroxymethyl)propan-2-ammonium 2-[[4-[2-fluoro-4-[[1-[(4-fluorophenyl)carbamoyl]cyclopropanecarbonyl]amino]phenoxy]-6-ethoxy-7-quinolyl]oxy]acetate;

3-[[4-[2-fluoro-4-[[1-[(4-fluorophenyl)carbamoyl]cyclopropanecarbonyl]amino]phenoxy]-6-ethoxy-7-quinolyl]oxy]propionic acid;

lithium 3-[[4-[2-fluoro-4-[[1-[(4-fluorophenyl)carbamoyl]cyclopropanecarbonyl]amino]phenoxy]-6-ethoxy-7-quinolyl]oxy]propionate;

sodium 3-[[4-[2-fluoro-4-[[1-[(4-fluorophenyl)carbamoyl]cyclopropanecarbonyl]amino]phenoxy]-6-ethoxy-7-quinolyl]oxy]propionate;

potassium 3-[[4-[2-fluoro-4-[[1-[(4-fluorophenyl)carbamoyl]cyclopropanecarbonyl]amino]phenoxy]-6-ethoxy-7-quinolyl]oxy]propionate;

magnesium 3-[[4-[2-fluoro-4-[[1-[(4-fluorophenyl)carbamoyl]cyclopropanecarbonyl]amino]phenoxy]-6-ethoxy-7-quinolyl]oxy]propionate;

calcium 3-[[4-[2-fluoro-4-[[1-[(4-fluorophenyl)carbamoyl]cyclopropanecarbonyl]amino]phenoxy]-6-ethoxy-7-quinolyl]oxy]propionate;

ammonium 3-[[4-[2-fluoro-4-[[1-[(4-fluorophenyl)carbamoyl]cyclopropanecarbonyl]amino]phenoxy]-6-ethoxy-7-quinolyl]oxy]propionate;

triethylammonium 3-[[4-[2-fluoro-4-[[1-[(4-fluorophenyl)carbamoyl]cyclopropane carbonyl]amino]phenoxy]-6-ethoxy-7-quinolyl]oxy]propionate;

1,3-dihydroxy-2-(hydroxymethyl)propan-2-ammonium 3-[[4-[2-fluoro-4-[[1-[(4-fluorophenyl)carbamoyl]cyclopropanecarbonyl]amino]phenoxy]-6-ethoxy-7-quinolyl]oxy]propionate;

4-[[4-[2-fluoro-4-[[1-[(4-fluorophenyl)carbamoyl]cyclopropanecarbonyl]amino]phenoxy]-6-ethoxy-7-quinolyl]oxy]butyric acid;

lithium 4-[[4-[2-fluoro-4-[[1-[(4-fluorophenyl)carbamoyl]cyclopropanecarbonyl]amino]phenoxy]-6-ethoxy-7-quinolyl]oxy]butyrate;

sodium 4-[[4-[2-fluoro-4-[[1-[(4-fluorophenyl)carbamoyl]cyclopropanecarbonyl]amino]phenoxy]-6-ethoxy-7-quinolyl]oxy]butyrate;

potassium 4-[[4-[2-fluoro-4-[[1-[(4-fluorophenyl)carbamoyl]cyclopropanecarbonyl]amino]phenoxy]-6-ethoxy-7-quinolyl]oxy]butyrate;

magnesium 4-[[4-[2-fluoro-4-[[1-[(4-fluorophenyl)carbamoyl]cyclopropanecarbonyl]amino]phenoxy]-6-ethoxy-7-quinolyl]oxy]butyrate;

calcium 4-[[4-[2-fluoro-4-[[1-[(4-fluorophenyl)carbamoyl]cyclopropanecarbonyl]amino]phenoxy]-6-ethoxy-7-quinolyl]oxy]butyrate;

ammonium 4-[[4-[2-fluoro-4-[[1-[(4-fluorophenyl)carbamoyl]cyclopropanecarbonyl]amino]phenoxy]-6-ethoxy-7-quinolyl]oxy]butyrate;

triethylammonium 4-[[4-[2-fluoro-4-[[1-[(4-fluorophenyl)carbamoyl]cyclopropane carbonyl]amino]phenoxy]-6-ethoxy-7-quinolyl]oxy]butyrate;

1,3-dihydroxy-2-(hydroxymethyl)propan-2-ammonium 4-[[4-[2-fluoro-4-[[1-[(4-fluorophenyl)carbamoyl]cyclopropanecarbonyl]amino]phenoxy]-6-ethoxy-7-quinolyl]oxy]butyrate;

5-[[4-[2-fluoro-4-[[1-[(4-fluorophenyl)carbamoyl]cyclopropanecarbonyl]amino]phenoxy]-6-ethoxy-7-quinolyl]oxy]valeric acid;

lithium 5-[[4-[2-fluoro-4-[[1-[(4-fluorophenyl)carbamoyl]cyclopropanecarbonyl]amino]phenoxy]-6-ethoxy-7-quinolyl]oxy]valerate;

sodium 5-[[4-[2-fluoro-4-[[1-[(4-fluorophenyl)carbamoyl]cyclopropanecarbonyl]amino]phenoxy]-6-ethoxy-7-quinolyl]oxy]valerate;

potassium 5-[[4-[2-fluoro-4-[[1-[(4-fluorophenyl)carbamoyl]cyclopropanecarbonyl]amino]phenoxy]-6-ethoxy-7-quinolyl]oxy]valerate;

magnesium 5-[[4-[2-fluoro-4-[[1-[(4-fluorophenyl)carbamoyl]cyclopropanecarbonyl]amino]phenoxy]-6-ethoxy-7-quinolyl]oxy]valerate;

calcium 5-[[4-[2-fluoro-4-[[1-[(4-fluorophenyl)carbamoyl]cyclopropanecarbonyl]amino]phenoxy]-6-ethoxy-7-quinolyl]oxy]valerate;

ammonium 5-[[4-[2-fluoro-4-[[1-[(4-fluorophenyl)carbamoyl]cyclopropanecarbonyl]amino]phenoxy]-6-ethoxy-7-quinolyl]oxy]valerate;

triethylammonium 5-[[4-[2-fluoro-4-[[1-[(4-fluorophenyl)carbamoyl]cyclopropane carbonyl]amino]phenoxy]-6-ethoxy-7-quinolyl]oxy]valerate;

1,3-dihydroxy-2-(hydroxymethyl)propan-2-ammonium 5-[[4-[2-fluoro-4-[[1-[(4-fluorophenyl)carbamoyl]cyclopropanecarbonyl]amino]phenoxy]-6-ethoxy-7-quinolyl]oxy]valerate;

6-[[4-[2-fluoro-4-[[1-[(4-fluorophenyl)carbamoyl]cyclopropanecarbonyl]amino]phenoxy]-6-ethoxy-7-quinolyl]oxy]caproic acid;
lithium 6-[[4-[2-fluoro-4-[[1-[(4-fluorophenyl)carbamoyl]cyclopropanecarbonyl]amino]phenoxy]-6-ethoxy-7-quinolyl]oxy]caproate;
sodium 6-[[4-[2-fluoro-4-[[1-[(4-fluorophenyl)carbamoyl]cyclopropanecarbonyl]amino]phenoxy]-6-ethoxy-7-quinolyl]oxy]caproate;
potassium 6-[[4-[2-fluoro-4-[[1-[(4-fluorophenyl)carbamoyl]cyclopropanecarbonyl]amino]phenoxy]-6-ethoxy-7-quinolyl]oxy]caproate;
magnesium 6-[[4-[2-fluoro-4-[[1-[(4-fluorophenyl)carbamoyl]cyclopropanecarbonyl]amino]phenoxy]-6-ethoxy-7-quinolyl]oxy]caproate;
calcium 6-[[4-[2-fluoro-4-[[1-[(4-fluorophenyl)carbamoyl]cyclopropanecarbonyl]amino]phenoxy]-6-ethoxy-7-quinolyl]oxy]caproate;
ammonium 6-[[4-[2-fluoro-4-[[1-[(4-fluorophenyl)carbamoyl]cyclopropanecarbonyl]amino]phenoxy]-6-ethoxy-7-quinolyl]oxy]caproate;
triethylammonium 6-[[4-[2-fluoro-4-[[1-[(4-fluorophenyl)carbamoyl]cyclopropane carbonyl]amino]phenoxy]-6-ethoxy-7-quinolyl]oxy]caproate;
1,3-dihydroxy-2-(hydroxymethyl)propan-2-ammonium 6-[[4-[2-fluoro-4-[[1-[(4-fluorophenyl)carbamoyl]cyclopropanecarbonyl]amino]phenoxy]-6-ethoxy-7-quinolyl]oxy]caproate;
7-[[4-[2-fluoro-4-[[1-[(4-fluorophenyl)carbamoyl]cyclopropanecarbonyl]amino]phenoxy]-6-ethoxy-7-quinolyl]oxy]heptanoic acid;
lithium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
sodium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
potassium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
magnesium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
calcium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
ammonium 7-[[4-[2-fluoro-4-[[1-[(4-fluorophenyl)carbamoyl]cyclopropanecarbonyl]amino]phenoxy]-6-ethoxy-7-quinolyl]oxy]heptanoate;
triethylammonium 7-[[4-[2-fluoro-4-[[1-[(4-fluorophenyl)carbamoyl]cyclopropane carbonyl]amino]phenoxy]-6-ethoxy-7-quinolyl]oxy]heptanoate; and
1,3-dihydroxy-2-(hydroxymethyl)propan-2-ammonium 7-[[4-[2-fluoro-4-[[1-[(4-fluorophenyl)carbamoyl]cyclopropanecarbonyl]amino]phenoxy]-6-ethoxy-7-quinolyl]oxy]heptanoate.

8. A preparation method of the quinolyl-substituted carboxylic acid compound or the pharmaceutically acceptable salt thereof according to claim 1, comprising, but not limited to, the following steps:

Scheme 1

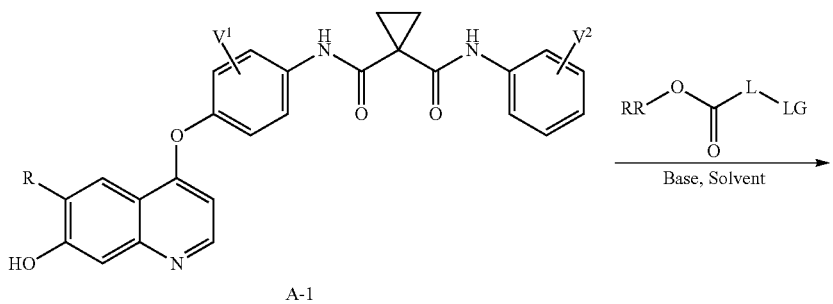

A-1

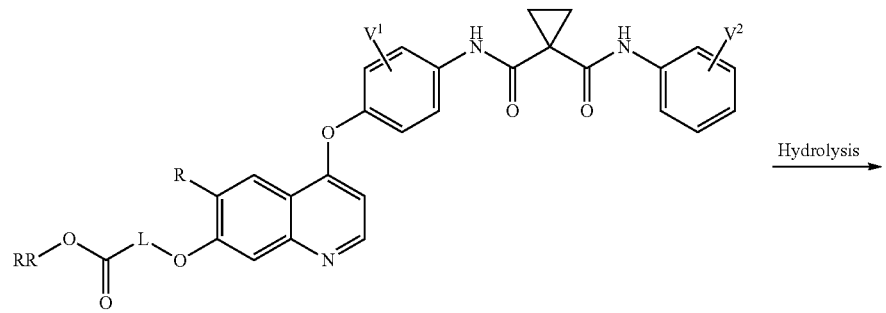

A-2

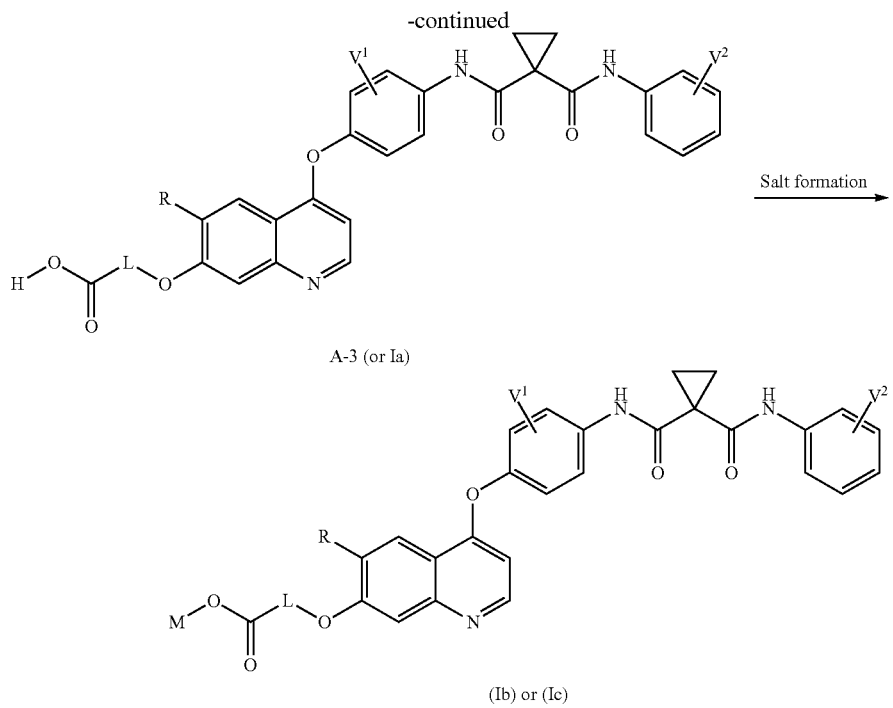

wherein $V^1$, $V^2$, R, L and M are as defined in claim 1;
LG is F, Cl, Br, I, $CH_3SO_3$, $CH_3CH_2SO_3$, $CH_3(CH_2)_2SO_3$, $(CH_3)_2CHSO_3$, tert-BuSO$_3$, PhSO$_3$, o-CH$_3$PhSO$_3$, m-CH$_3$PhSO$_3$, p-CH$_3$PhSO$_3$, o-O$_2$NPhSO$_3$, m-O$_2$NPhSO$_3$, p-O$_2$NPhSO$_3$, or CF$_3$SO$_3$; and RR is hydrogen, $C_{1-12}$ alkyl, $C_{3-12}$ cycloalkyl, $C_{6-12}$ aryl, $C_{5-12}$ heteroaryl or $C_{3-12}$ heteroalicyclic group, and hydrogen of RR is selectively substituted by $G^4$;

wherein $G^4$ is selected from hydrogen, deuterium, —CN, —CF$_3$, —CO$_2$H, halogen, $C_{1-12}$ alkyl, $C_{3-12}$ cycloalkyl, $C_{2-12}$ alkenyl, $C_{2-12}$ alkynyl, $C_{6-12}$ aryl, $C_{5-12}$ heteroaryl, $C_{3-12}$ heteroalicyclic group $R^1O—$, $R^1R^2N—$, $R^1S(=O)_m—$, $R^1R^2NS(=O)_m—$, $R^3C(=O)—$, $R^1R^2NC(=O)—$, $R^1OC(=O)—$, $R^3C(=O)O—$, $R^1R^2NC(=O)O—$, $R^3C(=O)NR^1—$, $R^1R^2NC(=O)NR^4—$, $R^1OC(=O)NR^4—$, $R^1S(=O)_mNR^4—$, $R^1R^2NS(=O)_mNR^4—$, $R^1R^2NC(=NR^5)NR^4—$, $R^1R^2NC(=CHNO_2)NR^4—$, $R^1R^2NC(=N—CN)NR^4—$, $R^1R^2NC(=NR^5)—$, $R^1S(=O)(=NR^5)NR^4—$, and $R^1R^2NS(=O)(=NR^5)—$;

$R^1$, $R^2$, $R^3$, $R^4$ and $R^5$ are each independently selected from hydrogen, deuterium, $C_{1-12}$ alkyl, $C_{2-12}$ alkenyl, $C_{2-12}$ alkynyl, $C_{3-12}$ cycloalkyl, $C_{6-12}$ aryl, $C_{5-12}$ heteroaryl, and $C_{3-12}$ heteroalicyclic group; $R^1$ and $R^2$, when being bonded to a same nitrogen atom, form a $C_{3-12}$ heteroalicyclic ring together with the nitrogen atom, wherein the $C_{3-12}$ heteroalicyclic ring selectively contains a hetero atom of O, N, and $S(=O)_m$; and hydrogen of $R^1$, $R^2$, $R^3$, $R^4$ and $R^5$ is selectively substituted by halogen, CN, $C_{1-12}$ alkyl or $C_{3-12}$ cycloalkyl; and m is 0 to 2.

* * * * *